(12) United States Patent
White et al.

(10) Patent No.: US 12,731,680 B2
(45) Date of Patent: Sep. 8, 2026

(54) SYSTEMS AND METHODS OF PRODUCING PATIENT ENCOUNTER RECORDS

(71) Applicant: ZOLL Medical Corporation, Chelmsford, MA (US)

(72) Inventors: Elijah A. White, Wellesley, MA (US); Adam T. Dawson, Burlington (CA); David A. Jaros, Brooklyn Park, MN (US); Gary A. Freeman, Waltham, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

(21) Appl. No.: 19/095,885

(22) Filed: Mar. 31, 2025

(65) Prior Publication Data

US 2025/0232869 A1 Jul. 17, 2025

Related U.S. Application Data

(63) Continuation of application No. 17/217,164, filed on Mar. 30, 2021, now abandoned.

(Continued)

(51) Int. Cl.
*G16H 40/20* (2018.01)
*G06F 16/242* (2019.01)
(Continued)

(52) U.S. Cl.
CPC ........... *G16H 40/20* (2018.01); *G06F 16/242* (2019.01); *G06K 7/1413* (2013.01);
(Continued)

(58) Field of Classification Search
CPC ........ G16H 10/60; G16H 40/67; G16H 40/20; A61N 1/3925; A61N 1/3993; A61N 1/39; A61N 1/3904
(Continued)

(56) References Cited

U.S. PATENT DOCUMENTS 5,267,155 A 11/1993 Buchanan et al.
6,083,248 A 7/2000 Thompson
(Continued)

FOREIGN PATENT DOCUMENTS

CN 101589393 A 11/2009
CN 102982226 A 3/2013
(Continued)

OTHER PUBLICATIONS

Alejandro Plaza Roncero, Gonçalo Marques, Beatriz Sainz-De-Abajo, Francisco Martín-Rodríguez, Carlos del Pozo Vegas, Begonya Garcia-Zapirain, Isabel de la Torre-Díez1; Mobile Health Apps for Emergencies: Systematic Review Dec. 11, 2020, vol. 8, No. 12, pp. 1-5 (Year: 2020).*

(Continued)

*Primary Examiner* — Alaaeldin M. Elshaer
*Assistant Examiner* — Teresa S Williams
(74) *Attorney, Agent, or Firm* — Secant IP, P.L.L.C.

(57) ABSTRACT

A system for consolidating medical data from multiple devices involved in a patient encounter is provided. The system includes a mobile computing device that acquires, via a medical device interface, identifiers of each medical device, generates association information including the one or more identifiers, and transmits the association information to a server. The server receives and stores one or more medical device case files from the medical devices, receives the association information from the mobile computing device, associates the one or more medical device case files with one another, and produces an integrated data source encounter structure including case data from the one or more medical device case files for subsequent processing.

27 Claims, 30 Drawing Sheets

Related U.S. Application Data

(60) Provisional application No. 63/111,234, filed on Nov. 9, 2020, provisional application No. 63/002,678, filed on Mar. 31, 2020.

(51) Int. Cl.
*G06K 7/14* (2006.01)
*G16H 10/60* (2018.01)
*G16H 40/67* (2018.01)
*A61N 1/39* (2006.01)

(52) U.S. Cl.
CPC ........... *G06K 7/1417* (2013.01); *G16H 10/60* (2018.01); *G16H 40/67* (2018.01); *A61N 1/3925* (2013.01)

(58) Field of Classification Search
USPC ............................................................ 705/3
See application file for complete search history.

(56) References Cited

U.S. PATENT DOCUMENTS 6,088,616 A 7/2000 Olson et al.
6,106,459 A 8/2000 Clawson
6,117,073 A 9/2000 Jones et al.
6,282,531 B1 8/2001 Haughton et al.
6,363,282 B1 3/2002 Nichols et al.
6,370,428 B1 4/2002 Snyder et al.
6,397,104 B1 5/2002 Miller et al.
6,607,481 B1 8/2003 Clawson
6,610,010 B2 8/2003 Sjoqvist
6,684,276 B2 1/2004 Walker et al.
6,735,272 B1 5/2004 Sorenson
6,747,556 B2 6/2004 Medema et al.
6,754,526 B2 6/2004 Daynes et al.
6,813,517 B2 11/2004 Daynes et al.
6,937,150 B2 8/2005 Medema et al.
7,039,628 B2 5/2006 Logan, Jr.
7,044,742 B2 5/2006 Sumiya et al.
7,412,395 B2 8/2008 Rowlandson
7,490,085 B2 2/2009 Walker et al.
7,650,181 B2 1/2010 Freeman et al.
7,668,820 B2 2/2010 Zuleba
7,672,720 B2 3/2010 Heath
7,769,465 B2 8/2010 Matos
7,805,190 B2 9/2010 Chapman et al.
7,937,146 B2 5/2011 Banville et al.
7,979,378 B2 7/2011 West et al.
8,081,071 B1 12/2011 Vaisnys et al.
8,712,793 B2 4/2014 Jones et al.
8,738,129 B2 5/2014 Packer et al.
8,781,577 B2 7/2014 Freeman
8,818,522 B2 8/2014 Mass et al.
8,880,166 B2 11/2014 Tan et al.
9,119,971 B2 9/2015 Elghazzawi
9,220,912 B2 12/2015 Elghazzawi
9,658,756 B2 5/2017 Freeman et al.
10,137,265 B2 11/2018 Freeman et al.
10,692,591 B2 6/2020 Huang et al.
10,713,377 B2 7/2020 Joscelyne et al.
11,031,139 B2 * 6/2021 Barkol ................ G10L 15/1815
11,177,026 B2 * 11/2021 Heavelyn ............... G16H 40/67
11,342,075 B2 5/2022 Podobas et al.
2001/0016696 A1 8/2001 Bystrom et al.
2002/0004729 A1 1/2002 Zak et al.
2002/0073099 A1 6/2002 Gilbert et al.
2003/0014222 A1 1/2003 Klass et al.
2003/0025602 A1 2/2003 Medema et al.
2003/0028219 A1 2/2003 Powers et al.
2003/0105649 A1 6/2003 Sheiner et al.
2003/0212311 A1 11/2003 Nova et al.
2003/0212438 A1 11/2003 Nova et al.
2003/0212575 A1 11/2003 Saalsaa
2004/0049233 A1 3/2004 Edwards
2004/0064342 A1 4/2004 Browne et al.
2004/0088317 A1 5/2004 Fabrick et al.
2004/0214148 A1 10/2004 Salvino et al.
2005/0015115 A1 1/2005 Sullivan et al.
2005/0149363 A1 7/2005 Loiterman et al.
2005/0256740 A1 11/2005 Kohan et al.
2006/0015254 A1 1/2006 Smith
2006/0030891 A1 2/2006 Saltzstein et al.
2006/0084043 A1 4/2006 Weaver et al.
2006/0149321 A1 7/2006 Merry et al.
2007/0032830 A1 2/2007 Bowers
2007/0185545 A1 8/2007 Duke
2007/0203742 A1 8/2007 Jones et al.
2008/0097909 A1 4/2008 Dicks et al.
2008/0138778 A1 6/2008 Eggert et al.
2008/0243549 A1 10/2008 Woronka et al.
2008/0244717 A1 10/2008 Jelatis et al.
2009/0222539 A1 9/2009 Lewis et al.
2010/0250643 A1 9/2010 Savage et al.
2011/0060378 A1 3/2011 Tuysserkani
2011/0284004 A1 11/2011 Silver et al.
2011/0295078 A1 12/2011 Reid et al.
2012/0081230 A1 4/2012 Sullivan et al.
2012/0191476 A1 7/2012 Reid et al.
2012/0226771 A1 9/2012 Harrington et al.
2012/0253842 A1 10/2012 Curran et al.
2012/0304054 A1 11/2012 Orf et al.
2013/0096649 A1 4/2013 Martin et al.
2013/0132465 A1 5/2013 Brown
2013/0159021 A1 6/2013 Felsher
2013/0191161 A1 7/2013 Churchwell et al.
2013/0275151 A1 10/2013 Moore et al.
2014/0019159 A1 1/2014 Singh et al.
2014/0222805 A1 8/2014 Huang et al.
2014/0249854 A1 9/2014 Moore et al.
2014/0337047 A1 11/2014 Mears et al.
2014/0365175 A1 12/2014 Packer et al.
2015/0154367 A1 6/2015 Shetty et al.
2016/0026762 A1 1/2016 Radhakrishnan et al.
2016/0085914 A1 3/2016 Douglass et al.
2016/0256622 A1 9/2016 Day et al.
2016/0337829 A1 11/2016 Fletcher et al.
2017/0109502 A1 4/2017 Labkoff et al.
2017/0150939 A1 6/2017 Shah
2017/0169166 A1 6/2017 Colley et al.
2017/0323055 A1 11/2017 Gaffield
2017/0337338 A1 11/2017 Dunn et al.
2018/0114288 A1 4/2018 Aldaz et al.
2019/0076024 A1 3/2019 Gosink et al.
2021/0304860 A1 9/2021 Hart et al.
2022/0310219 A1 9/2022 Sanchez, Jr. et al.

FOREIGN PATENT DOCUMENTS

WO WO-2005043306 A2 * 5/2005 ............. G16H 40/67
WO 2005109291 11/2005
WO 2007058835 5/2007
WO 2007089225 8/2007
WO 2009136259 11/2009
WO 2011/127459 10/2011
WO 2012100219 7/2012
WO 2014/105592 7/2014
WO 2018013411 A1 1/2018
WO 2018218162 A1 11/2018
WO 2021202490 A1 10/2021

OTHER PUBLICATIONS

International Search Report and Written Opinion received for PCT/US2021/024799; dated Jul. 14, 2021. 21 pages.
Wu et al., “Synchronizing Device Clocks Using IEEE 1588 and Blackfin Embedded Processors”, Analog Dialogue 43-11 (Nov. 2009).
Mozer R. et al., “Matching with Text Data: An Experimental Evaluation of Methods for Matching Documents and of Measuring Match Quality”, arXiv:1801.00644v7, Mar. 13, 2019, 71 pages.
Jones, Mike, “Get in Sync!: IEEE 1588v2 Transparent Clock Benefits for Industrial Control Distributed Networks,” Micrel, Inc.,

(56) References Cited

OTHER PUBLICATIONS retrieved from http://ww1.microchip.com/downloads/en/AppNotes/Get%20in%20Sync.pdf on May 3, 2021.
"IEEE Standard for a Precision Clock Synchronization Protocol for Networked Measurement and Control Systems", IEEE Instrumentation and Measurement Society, IEEE Std 1588™-2008 (Jul. 24, 2008).
Invitation to pay additional fees received for PCT/US2021/024833, dated Jul. 16, 2021. 13 pages.
Peng, et al., "A literature review of current technologies on health data integration for patient-centered health management," Health Informatics Journal, Dec. 30, 2019. 26 pages.
European Communication Pursuant to Article 94(3) EPC issued in 21721254.7 dated Dec. 9, 2025.

* cited by examiner

| Encounter ID | Medical Device $ID_1$ | $Timestamp_1$ | Medical Device $ID_2$ | $Timestamp_2$ |
|---|---|---|---|---|
| 128b2830-5014-11ea-b77f-2e728ce88125 | 839402938 | 2019-05-01 11:20:34 | 839402967 | 2019-05-01 11:22:15 |

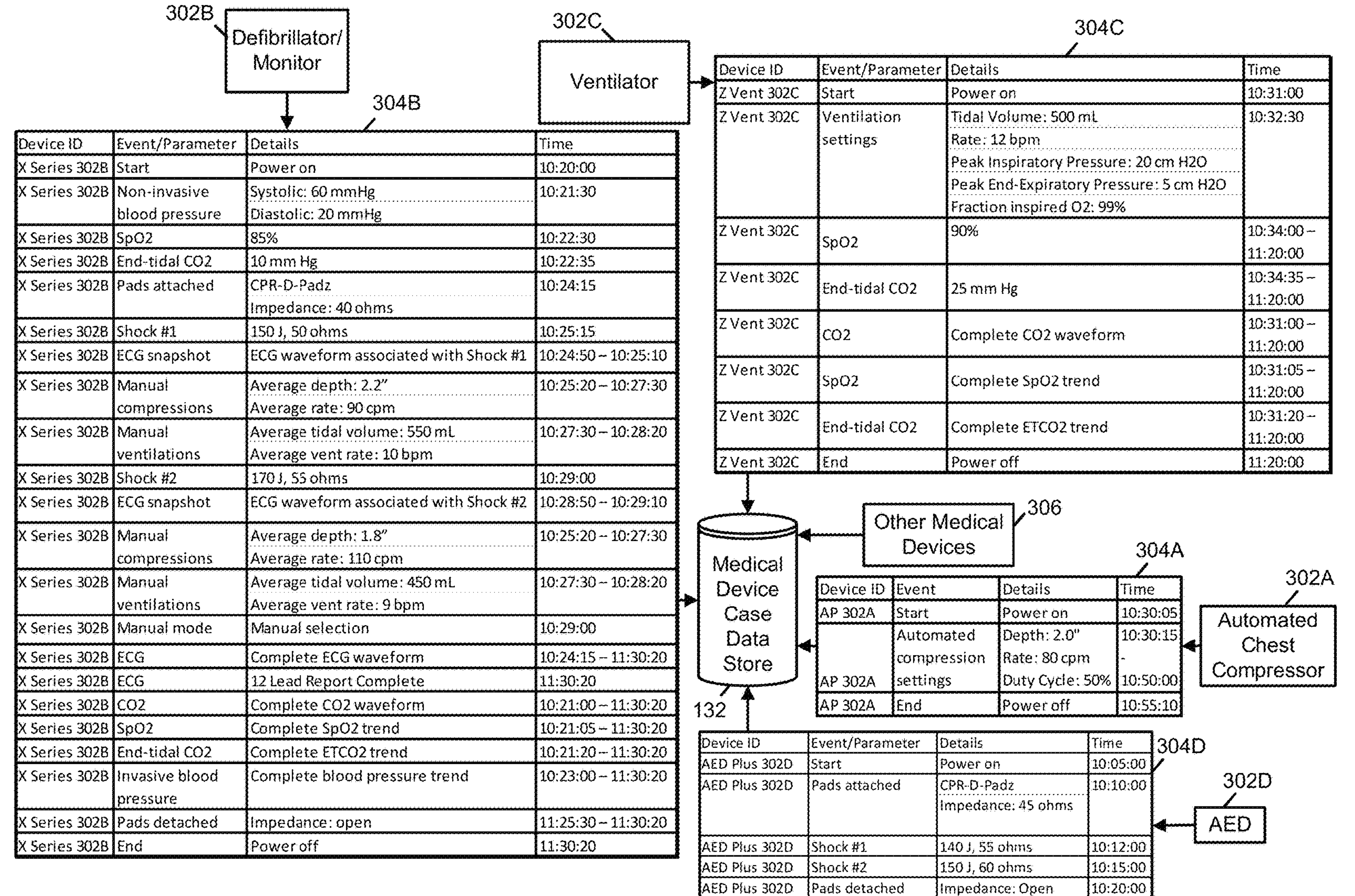

| Device ID | Event/Parameter | Details | Time |
|---|---|---|---|
| X Series 302B | Start | Power on | 10:20:00 |
| X Series 302B | Non-invasive blood pressure | Systolic: 60 mmHg<br>Diastolic: 20 mmHg | 10:21:30 |
| X Series 302B | SpO2 | 85% | 10:22:30 |
| X Series 302B | End-tidal CO2 | 10 mm Hg | 10:22:35 |
| X Series 302B | Pads attached | CPR-D-Padz<br>Impedance: 40 ohms | 10:24:15 |
| X Series 302B | Shock #1 | 150 J, 50 ohms | 10:25:15 |
| X Series 302B | ECG snapshot | ECG waveform associated with Shock #1 | 10:24:50 – 10:25:10 |
| X Series 302B | Manual compressions | Average depth: 2.2"<br>Average rate: 90 cpm | 10:25:20 – 10:27:30 |
| X Series 302B | Manual ventilations | Average tidal volume: 550 mL<br>Average vent rate: 10 bpm | 10:27:30 – 10:28:20 |
| X Series 302B | Shock #2 | 170 J, 55 ohms | 10:29:00 |
| X Series 302B | ECG snapshot | ECG waveform associated with Shock #2 | 10:28:50 – 10:29:10 |
| X Series 302B | Manual compressions | Average depth: 1.8"<br>Average rate: 110 cpm | 10:25:20 – 10:27:30 |
| X Series 302B | Manual ventilations | Average tidal volume: 450 mL<br>Average vent rate: 9 bpm | 10:27:30 – 10:28:20 |
| X Series 302B | Manual mode | Manual selection | 10:29:00 |
| X Series 302B | ECG | Complete ECG waveform | 10:24:15 – 11:30:20 |
| X Series 302B | ECG | 12 Lead Report Complete | 11:30:20 |
| X Series 302B | CO2 | Complete CO2 waveform | 10:21:00 – 11:30:20 |
| X Series 302B | SpO2 | Complete SpO2 trend | 10:21:05 – 11:30:20 |
| X Series 302B | End-tidal CO2 | Complete ETCO2 trend | 10:21:20 – 11:30:20 |
| X Series 302B | Invasive blood pressure | Complete blood pressure trend | 10:23:00 – 11:30:20 |
| X Series 302B | Pads detached | Impedance: open | 11:25:30 – 11:30:20 |
| X Series 302B | End | Power off | 11:30:20 |

| Device ID | Event/Parameter | Details | Time |
|---|---|---|---|
| Z Vent 302C | Start | Power on | 10:31:00 |
| Z Vent 302C | Ventilation settings | Tidal Volume: 500 mL<br>Rate: 12 bpm<br>Peak Inspiratory Pressure: 20 cm H2O<br>Peak End-Expiratory Pressure: 5 cm H2O<br>Fraction inspired O2: 99% | 10:32:30 |
| Z Vent 302C | SpO2 | 90% | 10:34:00 – 11:20:00 |
| Z Vent 302C | End-tidal CO2 | 25 mm Hg | 10:34:35 – 11:20:00 |
| Z Vent 302C | CO2 | Complete CO2 waveform | 10:31:00 – 11:20:00 |
| Z Vent 302C | SpO2 | Complete SpO2 trend | 10:31:05 – 11:20:00 |
| Z Vent 302C | End-tidal CO2 | Complete ETCO2 trend | 10:31:20 – 11:20:00 |
| Z Vent 302C | End | Power off | 11:20:00 |

| Device ID | Event | Details | Time |
|---|---|---|---|
| AP 302A | Start | Power on | 10:30:05 |
| AP 302A | Automated compression settings | Depth: 2.0"<br>Rate: 80 cpm<br>Duty Cycle: 50% | 10:30:15 - 10:50:00 |
| AP 302A | End | Power off | 10:55:10 |

| Device ID | Event/Parameter | Details | Time |
|---|---|---|---|
| AED Plus 302D | Start | Power on | 10:05:00 |
| AED Plus 302D | Pads attached | CPR-D-Padz<br>Impedance: 45 ohms | 10:10:00 |
| AED Plus 302D | Shock #1 | 140 J, 55 ohms | 10:12:00 |
| AED Plus 302D | Shock #2 | 150 J, 60 ohms | 10:15:00 |
| AED Plus 302D | Pads detached | Impedance: Open | 10:20:00 |
| AED Plus 302D | End | Power off | 10:25:00 |

SYSTEMS AND METHODS OF PRODUCING PATIENT ENCOUNTER RECORDS

CROSS-REFERENCE TO RELATED APPLICATIONS

This application is a continuation of U.S. patent application Ser. No. 17/217,164 (filed Mar. 30, 2021), which claims the benefit of U.S. Provisional Patent Application 63/002,678 (filed 31 Mar. 2020) and the benefit of U.S. Provisional Patent Application 63/111,234 (filed 9 Nov. 2020). The entire disclosure of each of these related applications is hereby incorporated herein by reference in its entirety.

BACKGROUND

Emergency care providers utilize a variety of specialized medical devices to treat the patients they encounter. These specialized medical devices can include defibrillators, ventilators, and automated resuscitation devices, among others. Defibrillators can be used to treat patients who suffer from a shockable cardiac arrhythmia, such as ventricular fibrillation or pulseless ventricular tachycardia. Ventilators can be used to supply oxygen to patients who have difficulty or are unable to breathe unassisted. Some automated resuscitation devices can perform cardiopulmonary resuscitation (CPR) chest compressions on patients who suffer sudden cardiac arrest, especially where such patients need to be moved to other locations for continued treatment.

Medical device case files arise as a byproduct of treating patients with computerized medical devices, such as those described above. Medical device case files can document medical device operation during a patient encounter, treatments delivered during the patient encounter, and values of patient parameters measured by the medical device during the patient encounter. Medical device case files may be reviewed by healthcare providers during or after patient encounters to gain insight into patient ailments and ultimately improve patient outcomes.

SUMMARY

In at least one example, a system for consolidating medical data from multiple devices involved in an encounter between a patient and an emergency healthcare provider is provided. The system includes a plurality of medical devices each having one or more identifiers. Each of the plurality of medical devices is configured to obtain case data related to the encounter between the patient and the emergency healthcare provider and transmit the obtained case data to a server as one or more medical device case files. The system further includes a mobile computing device having a medical device interface and a user interface. The mobile computing device is configured to acquire, via the medical device interface, one or more representations of the one or more identifiers of each medical device of the plurality of medical devices, generate association information including the one or more identifiers, and transmit the association information to the server. The server includes at least one processor and memory to execute instructions for associating the one or more medical device case files. The server is configured to be communicatively coupled with the plurality of medical devices and the mobile computing device. The server is further configured to receive and store the one or more medical device case files from the plurality of medical devices, receive the association information from the mobile computing device, generate at least one search criterion based at least in part on the association information to relate the one or more medical device case files to one another, identify the related one or more medical device case files based on the generated at least one search criterion, consolidate the one or more medical device case files to produce an integrated data source encounter structure including case data from the related one or more medical device case files, and transmit the integrated data source encounter structure for review of the encounter between the patient and the emergency healthcare provider to a receiving computing device.

In the system, the receiving computing device can include the mobile computing device. The mobile computing device can be further configured to render at least a portion of the integrated data source encounter structure via the user interface. The integrated data source encounter structure can include information other than patient information.

In the system, the receiving computing device can include at least one medical device of the plurality of medical devices. The receiving computing device can include a computing device within an emergency response center. The association information can include a token to access the integrated data source encounter structure. The server can be further configured to receive the token from the computing device within the emergency response center. In the system, to transmit can include to automatically transmit the integrated data source encounter structure to the computing device in response to reception of the token. The mobile computing device can be configured to transmit the token to the computing device within the emergency response center.

In the system, to transmit the one or more medical device case files can include to transmit one or more streams of the obtained case data to the one or more medical device case files. The integrated data source encounter structure can include the one or more streams of the obtained case data from the one or more medical device case files.

The system can further include a computing device including at least one user interface. The computing device can be configured to receive the integrated data source encounter structure; and render, subsequent to the encounter, at least a portion of the integrated data source encounter structure via the at least one user interface. In the system, the plurality of medical devices can include one or more of: a defibrillator, a patient monitor, an automated external defibrillator, a ventilator, an automated chest compression device, and a wearable defibrillator.

In the system, the association information can include patient information. The patient information can include one or more of patient name, patient identifier, age, gender, weight, height, and past medical history. The association information can include timestamp information indicating when at least a portion of the one or more medical device case files was created. The association information can include timestamp information indicating when the one or more representations of the one or more identifiers of each medical device were acquired. The association information can include geolocation information indicating where the mobile computing device was located when the one or more representations of the one or more identifiers of each medical device were acquired. The association information can include geolocation information indicating where the mobile computing device was located when the one or more representations of the one or more identifiers of each medical device were acquired. The association information can include geolocation information indicating where the mobile computing device was located during the encounter.

In the system, the medical device interface can include at least one of: a camera, a near-field communication sensor, a radio frequency identification sensor, a universal serial bus connector, an infrared sensor, a personal area network sensor, a proximity detector, a geolocation detector, and a wireless network connector. The medical device interface can include a camera, and the one or more identifiers can include one or more of a quick response code, a bar code, and a device identifier.

In the system, the one or more identifiers of each medical device correspond to one or more unique device identifiers. The mobile computing device can be further configured to generate one or more log entries of the encounter. The mobile computing device can be configured to transmit the one or more log entries to the server for inclusion in the integrated data source encounter structure. The server can be remote from the mobile computing device.

In the system, the obtained case data can include physiological data including one or more of: ECG data such as 12-lead ECG data, oxygen saturation data, capnographic data, and blood pressure data. The obtained case data can include treatment data including one or more of: defibrillation data, drug infusion data, chest compression data, and ventilation data. The obtained case data can include performance data including one or more of: chest compression performance data and ventilation performance data. The obtained case data can include protected health information.

In at least one example, an associating server for consolidating medical data from an encounter between a patient and an emergency healthcare provider is provided. The server includes a memory, a networking interface, and at least one processor communicatively coupled with the memory and the network interface. The memory stores at least one database configured to store case data from a plurality of medical device case files recorded during the encounter between the patient and the emergency healthcare provider. The at least one processor is configured to receive, via the network interface, the plurality of medical device case files from a plurality of medical devices used to treat the patient during the encounter, store the case data from the plurality of medical device case files in the at least one database, receive, via the network interface, association information from a mobile computing device, the association information including at least one identifier of each medical device of the plurality of medical devices, generate at least one search criterion based at least in part on the association information to relate the plurality of medical device case files to one another, identify the related plurality of medical device case files based on the generated at least one search criterion, consolidate the related plurality of medical device case files to produce an integrated data source encounter structure including at least a portion of the case data from the plurality of medical device case files from the at least one database, and transmit the integrated data source encounter structure for review of the encounter between the patient and the emergency healthcare provider to a receiving computing device.

In the associating server, to transmit the integrated data source encounter structure can include to transmit the integrated data source encounter structure to the mobile computing device. The integrated data source encounter structure can include information other than patient information. To transmit the integrated data source encounter structure can include to transmit the integrated data source encounter structure to at least one medical device of the plurality of medical devices. To transmit the integrated data source encounter structure can include to transmit the integrated data source encounter structure to a computing device within an emergency response center.

In the associating server, the association information can include a token to access the integrated data source encounter structure and the at least one processor can be further configured to receive the token from the computing device within the emergency response center. To transmit can include to automatically transmit the integrated data source encounter structure to the computing device in response to reception of the token. To receive the plurality of medical device case files can include to receive a plurality of streams of case data from the plurality of medical devices. The integrated data source encounter structure can include the plurality of streams of case data from the plurality of medical devices.

In the associating server, the association information can include patient information. The patient information can include one or more of: patient name, patient identifier, age, gender, weight, height, and past medical history. The association information can include timestamp information indicating when at least a portion of the plurality of medical device case files was recorded. The association information can include timestamp information indicating when one or more representations of the at least one identifier of each medical device were acquired. The association information can include geolocation information indicating where the mobile computing device was located when the one or more representations of the at least one identifier of each medical device were acquired. The association information can include geolocation information indicating where the mobile computing device was located when one or more representations of the at least one identifier of each medical device were acquired. The association information can include geolocation information indicating where the mobile computing device was located during the encounter. The one or more identifiers of each medical device can correspond to one or more unique device identifiers.

The associating server can be remote from the mobile computing device. In the associating server, the case data can include physiological data include one or more of: ECG data, oxygen saturation data, capnographic data, and blood pressure data. The case data can include treatment data including one or more of: defibrillation data, drug infusion data, chest compression data, and ventilation data. The case data can include performance data including one or more of: chest compression performance data and ventilation performance data. The case data can include protected health information.

In at least one example, a mobile computing device for consolidating case data from an encounter between a patient and an emergency healthcare provider is provided. The mobile computing device includes a memory, a user interface configured to receive user input concerning the encounter, a medical device interface configured to acquire a representation of an identifier of a medical device, a network interface, and at least one processor communicatively coupled with the user interface, the medical device interface, the network interface, and the memory. The at least one processor is configured to receive, via the user interface, input to acquire a plurality of representations of a plurality of identifiers of a plurality of medical devices involved in the encounter, store the acquired plurality of representations of the plurality of identifiers in the memory, generate association information including the plurality of identifiers, and transmit the association information to a server for associating and consolidating the case data from at least one medical device case file generated by the plurality of medical devices during the encounter.

In the mobile computing device, the at least one processor can be further configured to receive, via the network interface, an integrated data source encounter structure including at least a portion of the case data from the at least one medical device case file; and render, via the user interface, at least a portion of the integrated data source encounter structure. The integrated data source encounter structure can include information other than patient information. The portion of the case data can include physiological data including one or more of: ECG data such as 12-lead ECG data, oxygen saturation data, capnographic data, and blood pressure data. The portion of the case data can include treatment data including one or more of: defibrillation data, drug infusion data, chest compression data, and ventilation data. The portion of the case data can include performance data including one or more of: chest compression performance data and ventilation performance data. The portion of the case data can include protected health information.

In the mobile computing device, the association information can include patient information. The patient information can include one or more of: patient name, patient identifier, age, gender, weight, height, and past medical history. The association information can include timestamp information indicating when at least a portion of the at least one medical device case file was generated. The association information can include timestamp information indicating when the plurality of representations of the plurality of identifiers of the plurality of medical devices were acquired. The association information can include geolocation information indicating where the mobile computing device was located when the plurality of representations of the plurality of identifiers of the plurality of medical devices were acquired. The association information can include geolocation information indicating where the mobile computing device was located when the plurality of representations of the plurality of identifiers of the plurality of medical devices were acquired. The association information can include geolocation information indicating where the mobile computing device was located during the encounter. The association information can include a token to access an integrated data source encounter structure include at least a portion of the case data from the at least one medical device case file and the at least one processor can be configured to transmit the token to a computing device within an emergency response center.

In the mobile computing device, the medical device interface can include at least one of: a camera, a near-field communication sensor, a radio frequency identification sensor, a universal serial bus connector, an infrared sensor, a personal area network sensor, a proximity detector, a geolocation detector, and a wireless network connector. The medical device interface can include a camera, and the plurality of identifiers can include one or more of: a quick response code, a bar code, and a device identifier. The plurality of identifiers of the plurality of medical devices can correspond to one or more unique device identifiers. The at least one processor can be further configured to generate one or more log entries of the encounter. The at least one processor can be configured to transmit the one or more log entries to the server for inclusion in an integrated data source encounter structure including at least a portion of the case data from the at least one medical device case file. The mobile computing device can be remote from the server.

In at least one example, a computer implemented process for consolidating case data from an encounter between a patient and an emergency healthcare provider is provided. The computer implemented process includes receiving, via a user interface, input to acquire a plurality of representations of a plurality of identifiers of a plurality of medical devices involved in the encounter, storing the acquired plurality of representations of the plurality of identifiers in a memory of the computer, generating association information comprising the plurality of identifiers, and transmitting, via a network interface of the computer, the association information to a server for associating and consolidating the case data from at least one medical device case file generated by the plurality of medical devices during the encounter.

The computer implemented process can further include receiving, via the network interface, an integrated data source encounter structure including at least a portion of the case data from the at least one medical device case file; and rendering, via the user interface, at least a portion of the integrated data source encounter structure. In the computer implemented process, receiving the integrated data source encounter structure can include receiving information other than patient information. The computer implemented process can further include receiving, via the network interface, an integrated data source encounter structure comprising at least a portion of the case data from the at least one medical device case file and rendering, via the user interface, at least a portion of the integrated data source encounter structure.

In the computer implemented process, receiving the integrated data source encounter structure can include receiving information other than patient information. Rendering the at least a portion of the case data can include rendering physiological data comprising one or more of: ECG data such as 12-lead ECG data, oxygen saturation data, capnographic data, and blood pressure data. Rendering the at least a portion of the case data can include rendering treatment data comprising one or more of: defibrillation data, drug infusion data, chest compression data, and ventilation data. Rendering the at least a portion of the case data can include rendering performance data comprising one or more of: chest compression performance data and ventilation performance data. Rendering the at least a portion of the case data can include rendering protected health information.

In the computer implemented process, transmitting the association information can include transmitting patient information. Transmitting the patient information can include transmitting one or more of: patient name, patient identifier, age, gender, weight, height, and past medical history. Transmitting the association information can include transmitting timestamp information indicating when at least a portion of the at least one medical device case file was generated. Transmitting the association information can include transmitting timestamp information indicating when the plurality of representations of the plurality of identifiers of the plurality of medical devices were acquired. Transmitting the association information can include transmitting geolocation information indicating where the mobile computing device was located when the plurality of representations of the plurality of identifiers of the plurality of medical devices were acquired. Transmitting the association information can include transmitting geolocation information indicating where the mobile computing device was located when the plurality of representations of the plurality of identifiers of the plurality of medical devices were acquired. Transmitting the association information can include transmitting geolocation information indicating where the mobile computing device was located during the encounter. Transmitting the association information can include transmitting a token to access an integrated data source encounter structure including at least a portion of the case data from the at least one medical device case file and the computer implemented process further comprises transmitting, via the network interface, the token to a computing device within an emergency response center.

In the computer implemented process, receiving input to acquire the plurality of representations can include receiving input via at least one of: a camera, a near-field communication sensor, a radio frequency identification sensor, a universal serial bus connector, an infrared sensor, a personal area network sensor, a proximity detector, a geolocation detector, and a wireless network connector. Receiving input to acquire the plurality of representations can include receiving input via a camera, and the plurality of identifiers comprises one or more of: a quick response code, a bar code, and a device identifier. Receiving input to acquire the plurality of representations of the plurality of identifiers can include receiving input to acquire a plurality of representations of a plurality of unique medical device identifiers.

The computer implemented process can further include generating one or more log entries of the encounter. The computer implemented process can further include transmitting the one or more log entries to the server for inclusion in an integrated data source encounter structure including at least a portion of the case data from the at least one medical device case file.

In at least one example, a non-transitory computer-readable storage medium is provided. The non-transitory computer-readable storage medium stores instructions configured to execute the computer implemented process described above. In some examples, the non-transitory computer-readable storage medium is incorporated into a mobile computing device remote from the server referenced in the computer implemented process.

BRIEF DESCRIPTION OF THE DRAWINGS

Various aspects of the disclosure are discussed below with reference to the accompanying figures, which are not intended to be drawn to scale. The figures are included to provide an illustration and a further understanding of various examples and are incorporated in and constitute a part of this specification but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure. A quantity of each component in a particular figure is an example only and other quantities of each, or any, component could be used.

FIG. 3C is a data flow diagram illustrating the flow of medical device case files and data from a plurality of medical devices to a medical device case file data store.

FIG. 12 is a flow diagram of a case file data source integration process executed by a patient encounter data source integration service in accordance with at least one example disclosed herein.

DETAILED DESCRIPTION

Figure 1:
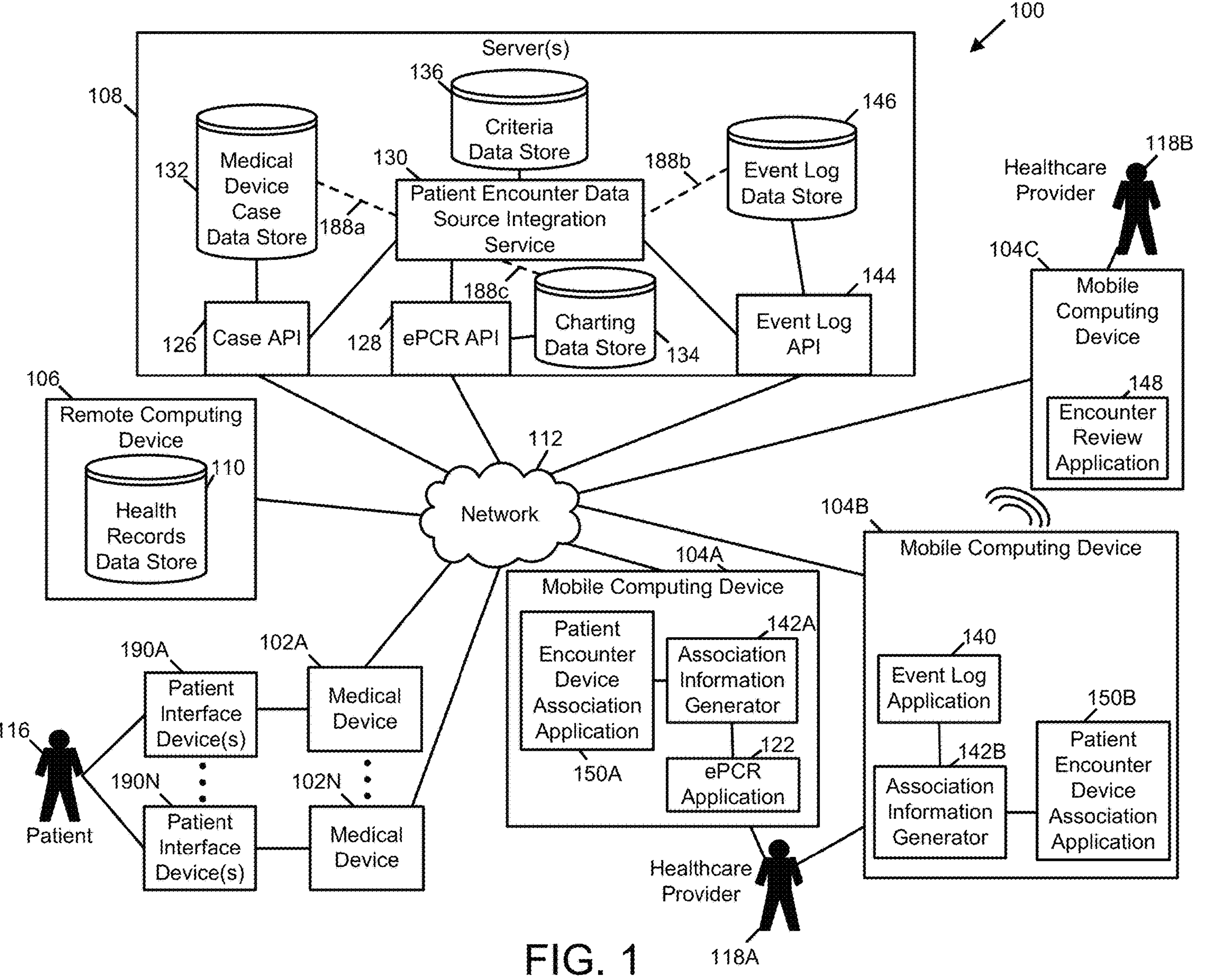
FIG. 1 is a schematic block diagram of a medical records system in accordance with at least one example disclosed herein.

Medical device case files generated during the course of a medical emergency encounter come in a variety of forms generated from different sources and include a wealth of medical data that can inform patient treatment and improve patient outcomes by providing healthcare providers with a more complete perspective regarding any given patient encounter. However, practical limitations to the convenience, accessibility and ultimate use of medical device case files exist, especially within the field of emergency medical services. In accordance with embodiments of the present disclosure, a healthcare provider may be able to gain access to an integrated data structure that incorporates the medical data (or other relevant data) sourced from multiple devices (e.g., defibrillator/monitor, ventilator, documenting device, etc.) associated with the same patient encounter, while the patient encounter is happening and/or after the encounter has finished. This real-time consolidation of data into an integrated data structure of the encounter may be particularly advantageous for the healthcare provider(s) to assess the overall state of care for the patient and make appropriate adjustments. In various embodiments, more specifically, a healthcare provider may use a mobile computing device to effectively associate together multiple devices used at the scene of a patient encounter. These associations may be sent to a server executing a data source integration service, which is also receiving medical data from the multiple devices, to use the device associations and produce an integrated data structure that consolidates together the received medical data from the multiple device sources. The integrated data structure may be continuously updated over time as the case encounter progresses, and further transmitted to the mobile computing device(s) of the healthcare provider(s) and/or another remote computing device (e.g., for telemedicine, telehealth purposes).

For example, consider an illustrative scenario of a crew of emergency medical services (EMS) healthcare providers in an ambulance being called upon to treat a patient suffering from an emergency medical condition (e.g., cardiac arrest, trauma, respiratory distress, drug overdose, etc.) and to transport the patient to a hospital. During the course of this emergency encounter, the treatment provided by healthcare providers is sometimes administered via one or more computerized medical devices. These medical devices can record and locally store case files as open data structures that include case data (e.g., streaming in real-time and/or for post-case review) that documents significant events within, and other relevant information regarding, the encounter. This case data for real-time streaming and/or post-case review can include physiological parameters of the patient acquired by sensors accessible by the medical devices during the encounter, data regarding treatment administered to patients via therapeutic devices controllable by the medical devices during the encounter, data regarding performance of the EMS healthcare providers, protected health information (PHI), and data regarding important milestones (e.g., code/event markers) within the encounter. Examples of physiological parameters stored within case data for real-time streaming and/or post-case review include heart rate, electrocardiogram (ECG) traces, blood pressure data, capnographic data, temperature, blood-oxygen data, and the like. Examples of treatment data stored within case data for real-time streaming and/or post-case review include defibrillation data, drug infusion data, chest compression data, and ventilation data. Examples of performance data stored within case data include chest compression performance data, ventilation performance data, and timely drug infusion information, amongst others. As this illustrative scenario makes clear, a wide variety of valuable case data can be generated by a variety of medical devices involved in a patient encounter. However, accessing this case data, particularly in real-time as the patient encounter unfolds, can be impractical for EMS and other healthcare providers because the medical device case files containing the medical data are scattered across multiple devices and lack organization for immediate access by the relevant healthcare providers.

While some medical devices are capable of transmitting the medical device case files (e.g., data structures in a real-time streaming format) they generate to a centralized storage location (e.g., a server), establishing a linkage between medical device case files documenting a particular patient encounter can be troublesome, particularly while the encounter is happening or immediately after the encounter. There are a wide variety of computerized medical devices in use with varying degrees of openness and interoperability. Moreover, for some EMS agencies the number of medical device case files, which are continuously being updated, may be large even within a relatively short time window. For example, an EMS agency in a major metropolitan area may have on the order of 100 defibrillators deployed with 10-20 or more concurrent patient encounters.

Given the life or death importance and level of stress associated with some patient encounters, establishing an immediate, real-time link between medical device case files (which may include continuously streaming data structures for mid-case review during the patient encounter) can be a powerful way to enhance the overall experience of the healthcare provider particularly during the case encounter, and ultimately the quality of patient care. Thus, at least some of the examples disclosed herein enable a healthcare provider to use a mobile computing device configured with a patient encounter device association application to locally associate together each of a plurality of medical devices used to provide treatment to the same patient, and as a result, upon communicating with a server based patient encounter data source integration service, produce an integrated data source encounter structure that includes all or at least a portion of the medical data relevant to the particular patient that is generated from each of the plurality of medical devices. As discussed herein for various embodiments, the integrated data source encounter structure may include a consolidated data structure that integrates medical data generated from different device sources at the same time, all corresponding to the same patient encounter. This allows a healthcare provider to view relevant data arising from multiple devices associated with the patient encounter in a real-time streaming context and/or during post-case review.

As described in further detail below, a healthcare provider located at an emergency scene may use a mobile computing device to effectively associate data generated from multiple medical devices, which associated data can subsequently be integrated into a single integrated data source encounter structure upon transmission to a server executing a service configured to generate encounter structures. Thus, an integrated patient encounter structure consolidating data from the multiple medical devices can be made available for the healthcare provider located at the scene and/or healthcare providers located remotely, over the course of the emergency event and/or for post-case review. As an example, the healthcare provider may use his/her mobile computing device to acquire an identifier, or a representation thereof, of each of a plurality of medical devices used/located at the scene. The mobile device executing a patient encounter device association application may then associate each of the plurality of medical devices together using the identifying information, and transmit association information to a server system executing an encounter data source integration service, which can be one or more computing devices located at a remote location. This association information can include a variety of informational elements, such as a token that uniquely identifies the patent encounter, the identifiers of the medical devices, timestamp information associated with the patient encounter, geolocation information that identifies a geographical location of the patient encounter, and potentially other information associated with the patient encounter. The server system may separately receive medical device case files (which may be continuously updated in real-time) from each of the medical devices located at the emergency scene and which are associated with the patient encounter. The server system may also happen to receive other medical device case files generated from other sources that are not associated with the patient encounter. Based on a generated search criterion that links the association information uploaded by the encounter device association application of the mobile computing device, the server system may search amongst the repository of medical case files/information and identify the related medical device case files associated with the particular patient encounter. From the identified related medical device case files, the server may produce a single integrated data source encounter structure for immediate review of the relevant data/events, for example, by the healthcare provider located at the emergency scene and/or another relevant healthcare provider (e.g., clinician available via telemedicine). As such, the integrated data source encounter structure may be reviewable via, for example, a user interface of the mobile computing device, a user interface of one of the medical devices, or a user interface of a computing device remote from the scene. Accordingly, the healthcare provider does not have to request or otherwise find the medical data associated with the patient encounter either at the server or at each of the plurality of medical devices. Rather, the relevant medical data may be made immediately available to the healthcare provider upon using his/her mobile device to effectively link the appropriate medical devices and their relevant case file data together.

FIG. 1 illustrates a medical records system 100 that includes and implements a patient encounter data source integration service 130 and device association generators 142A and 142B as part of respective patient encounter device association application(s) 150A and 150B of the mobile computing devices 104 in accordance with some examples. The system 100, according to examples of the present disclosure, can associate case files from multiple, different medical devices 102A-102N to one another to generate integrated data source structures of patient encounters. These consolidated medical records not only document patient encounters but also provide healthcare providers with information needed to improve patient outcomes. As shown in FIG. 1, the medical records system 100 includes one or more medical device(s) 102A-102N, one or more mobile computing devices 104A-104C, a remote computing device 106, and one or more server(s) 108 coupled to one another via a network 112. Each of the medical device(s) 102A-102N is configured to couple to one or more patient interface device(s) 190A-190N that are, in turn, configured to couple to a patient 116 during a patient encounter. For ease of reference, each of the medical device(s) 102A-102N, the mobile computing device(s) 104A-104C, the patient encounter device association application(s) 150A-150B, and the patient interface device(s) 190A-190N may be referred to herein collectively as the medical devices 102, the mobile computing devices 104, and the patient interface devices 190. Individual members of these collectives may be referred to generically as a medical device 102, a mobile computing device 104, a patient encounter device association application 150, and patient interface devices 190.

The system 100 further includes server(s) 108, which may be located remotely from the mobile computing devices 104 and the medical devices 102. For instance, the server(s) 108 may be housed in a datacenter that provides power and network connectivity to the server(s) 108. As shown in FIG. 1, the server(s) 108 can be configured to host one or more of: a medical device case application programming interface (API) 126, an ePCR API 128, a patient encounter data source integration service 130, a medical device case data store 132, a patient charting data store 134, a criteria data store 136, an event log API 144 and an event log data store 146. The remote computing device 106 can be configured to host a health records data store 110, which can receive and store medical data for a patient's medical record. In at least one example, an associating server of the server(s) 108 hosts the patient encounter data source integration service 130.

At least some of the system 100 advantageously leverage aspects of association information to identify case data. In embodiments of the present disclosure, a mobile computing device 104 may include a patient encounter device association application 150 that includes association generator(s) to generate the association information. As such, to aid the reader's understanding, a description of association information and the parts of the medical records system 100 that originate association information is provided prior to a description of the data source integration processes executed by the patient encounter data source integration service 130 and other parts of the system 100.

In some examples, association information includes any element of data useful to determine whether two or more medical device case files were generated within a particular patient encounter. As such, a wide variety of data can be characterized as association information, in various examples. For instance, in some examples, association information can include one or more identifiers of a medical device 102 that generated a case file, information regarding a patient treated during a patient encounter (e.g., patient name or other identifier of a patient, age, gender, weight, height, and/or past medical history), timestamp information recorded during the patient encounter (e.g., a timestamp indicating when at least a portion of a medical device case file was created and/or a timestamp indicating when the one or more identifiers of the medical device 102 were acquired), geolocation information recorded during the patient encounter (e.g., a geotag identifying a geographic location where the mobile computing device 104 acquired the one or more identifier of the medical device 102, and/or a token by the patient encounter device association application 150 of the mobile computing device 104 during the patient encounter (e.g., a universally unique identifier (UUID) or data that uniquely identifies the patient encounter). Association information can also include portions of event log data and/or charting data, which are discussed in further detail below.

Association information can originate from a wide variety of sources. For instance, in some examples, the association generators 142A and 142B of the respective encounter device association applications 150 are configured to generate association information upon request. In some examples, the requests can be embedded within system messages received from other processes hosted by the system 100 (e.g., the ePCR application 122 and/or the event log application 140). In these examples, the association generators 142A and 142B are configured to generate requested element(s) of association information (e.g., a token identifying a particular patient encounter) and return the requested element(s) of association information to the requesting process. In some examples, requests for association information can also be input received from a user interface of a mobile computing device 104. In these examples, the association generators 142A and 142B are configured to generate the requested association information and store the association information locally for subsequent processing. Alternatively or additionally, in some examples, the ePCR application 122 and/or the event log application 140 are configured to generate association information via execution of their encounter documentation processes. Examples of association information generated by the ePCR application 122 and/or the event log application 140 can include patient demographic and/or physiologic information, among other types of information collected by the ePCR application 122 and/or the event log application 140 as discussed herein.

Figure 2:
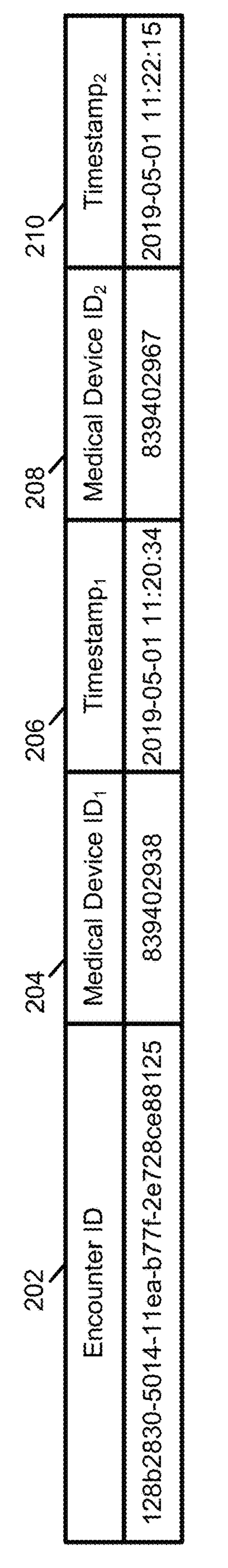
FIG. 2 is a record layout diagram of one example of association information in accordance with at least one example disclosed herein.

FIG. 2 illustrates one example of a record of association information that the association generators 142A and 142B are configured to generate individually, or in collaboration with the ePCR application 122 and/or the event log application 140. As shown in FIG. 2, the association information record includes an encounter ID field 202, a first medical device ID field 204, a first timestamp field 206, a second medical device ID field 208, and a second timestamp field 210. In this example, the encounter ID field 202 is configured to store a token (here a UUID), the first and second medical device ID fields 204 and 208 are configured to store medical device serial numbers, and the first and second timestamp fields 206 and 210 are configured to store timestamps that may be used to associate case files relevant to the same patient encounter together. As will be understood in view of FIG. 2, the association information record 200 relates the first and second medical devices and their respective timestamps with the patient encounter uniquely identified by the encounter ID 202. Further, as will be explained in detail below, each <medical device ID, timestamp> value pair within the association information record 200 provides the patient encounter data source integration service 130 with the information needed to identify, with high confidence, the medical device case files generated during the patient encounter identified by the encounter ID 202.

Returning to FIG. 1, in some examples, the patient encounter data source integration service 130 is configured to monitor for and receive association information. For instance, in some examples, the patient encounter data source integration service 130 is configured to monitor the charting data store 134 and/or the event log data store 146 for inbound association information received via the network 112. Alternatively or additionally, the patient encounter data source integration service 130 can be configured to receive messages from the ePCR API 128 and/or the event log API 144 comprising association information received via the network 112. Regardless, the inbound association information can be, for example, sourced from one or more new or modified ePCRs or event logs generated and transmitted by a mobile computing device 104. Alternatively or additionally, the inbound association information can be sourced from discrete messages transmitted, for example, by one of the association generators 142A and/or 142B. The operation of these programs within the context of a realistic usage scenario is described in more detail below.

To handle the inbound association information, the patient encounter data source integration service 130 is configured to execute one or more processes that attempt to identify case data within the case data store 132 that originated from one or more case files generated during a patient encounter associated with the inbound association information. Examples of these processes are described in detail below with reference to FIGS. 4-17. The patient encounter data source integration service 130 can be configured to take one or more of several actions in response to identifying case data that was generated during the patient encounter associated with the inbound association information. These actions may include producing consolidated medical data including the case data and/or combining the case data with charting data and/or event log data, storing the consolidated medical data (e.g., in the charting data store 134 and/or the event log data store), transmitting messages including the consolidated medical data in the form of an integrated data source encounter structure or portions thereof, and/or transmitting messages including the case data or identifiers of the case data. These messages can be transmitted to a mobile computing device 104, a medical device 102, and/or the remote computing device 106 (e.g., for storage in the health records data store 110) via the network 112 and one or more of the ePCR API 128, the event log API 144, and the case API 126. These and other actions that the patient encounter data source integration service 130 may be configured to take in response to identifying corresponding case data are also described in detail below with reference to FIGS. 4-17.

EMS Example

In some examples, the healthcare provider 118A, who for example may be an EMS technician, can attach the patient interface device(s) 190A-190N (e.g., physiological sensors, ECG sensors, SpO2 sensors, capnography sensors, blood pressure sensors, etc.) coupled to one or more of the medical devices 102 to the patient 116 to monitor and/or treat the patient 116. This treatment may involve the medical devices 102 and certain aspects such as events and other information may be documented by the healthcare provider 118A via the ePCR application 122 and/or the event log application 140 of one of the mobile computing devices 104.

Figure 3A:
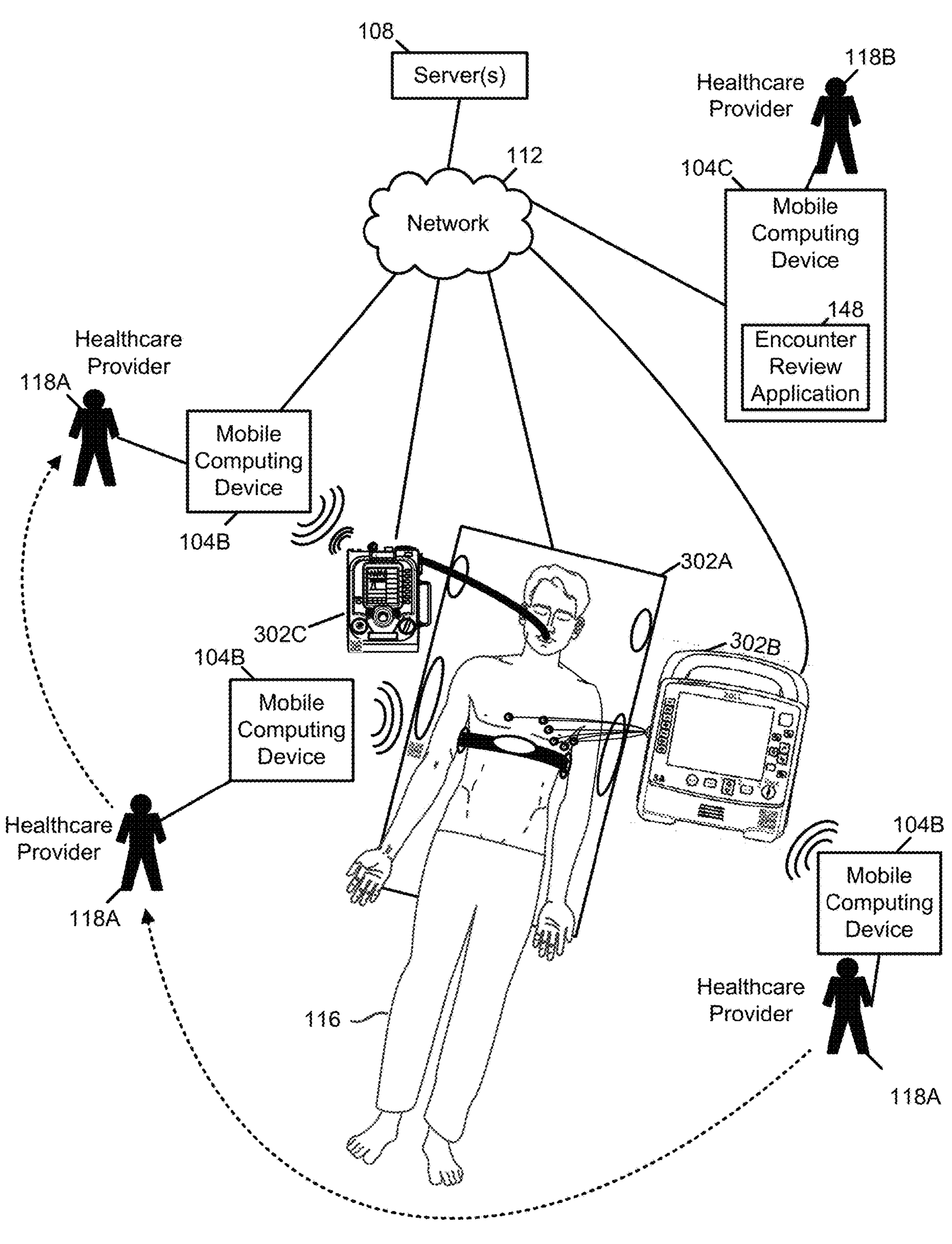
FIGS. 3A and 3B are diagrams illustrating emergency medical scenes in which a healthcare provider acquires of representations of medical device identifiers from various medical devices in accordance with at least one example disclosed herein.
Figure 3B:
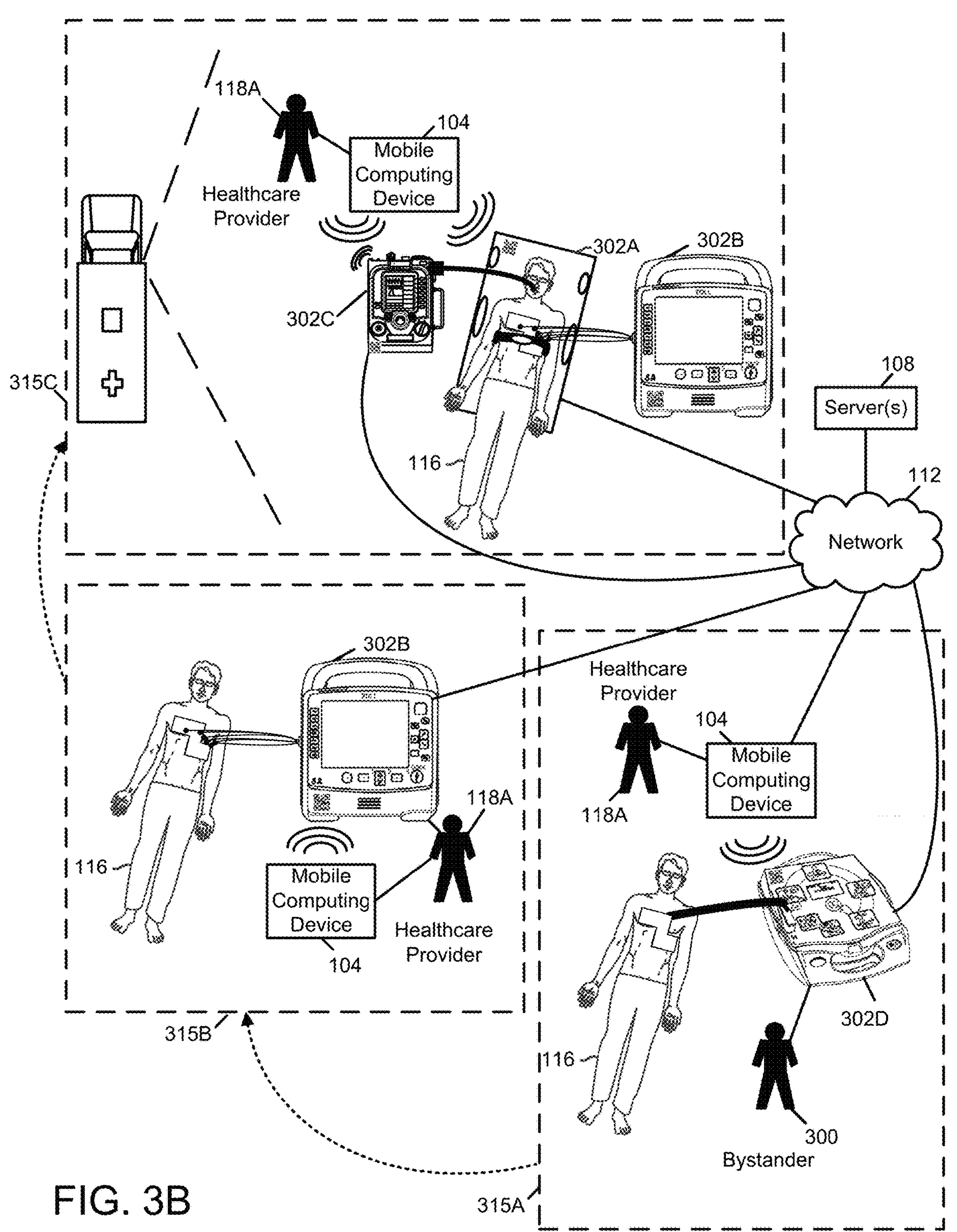

As discussed herein, a number of different types of medical devices 102 may be employed, such as those more specifically illustrated in FIGS. 3A-3C. For example, as discussed herein, a defibrillator/monitor 302B may collect a variety of different types of data including patient information (e.g., name, gender, size, weight, age, height, medical history, etc.), physiological information (e.g., ECG waveform, ECG snapshots before and/or after certain notable events that are marked/annotated for review, heart rate, oxygen saturation data, CO2 data, blood pressure data, amongst others), treatment information (e.g., drug infusions, electrotherapy events, start of chest compressions, start of ventilations), and healthcare provider performance information (e.g., average chest compression depth, average chest compression rate, percentage of chest compressions in target for depth/rate, average release velocity, pre-shock CPR pause, post-shock CPR pause, ventilation tidal volume data, ventilation minute volume data, ventilation rate data, drug infusion timing, etc.), to name a few. The ECG waveform and/or ECG snapshots may be captured using 10 or more electrodes coupled to the patient's body to generate a standard 12 lead report. A portion or all of the information collected by the defibrillator/monitor 302B may be uploaded as it is acquired to one or more server(s) via a network (e.g., the server(s) 108 and network 112 of FIG. 1, continuously, regularly, and/or post-case), as medical device case files, which may be updated at periodic intervals. Each medical device case file can have identifying information, for example, an identifier of the device from which the case file originated, timestamp data relevant to the start, end, length of time of the patient encounter, and/or geolocation information of the device during the patient encounter. An example of an appropriate defibrillator/monitor is the X Series® defibrillator/monitor, provided by ZOLL Medical Corporation, although other suitable defibrillator/monitor devices may be used in accordance with the present disclosure.

As illustrated in FIG. 3A, other medical devices located at a scene sending continuous real-time data to the server(s) 108 for consolidation with other case files relevant to the patient encounter may include, for example, a ventilator 302C, an automated chest compressor 302A, and/or other medical devices. For instance, the ventilator 302C may collect and send to the server(s) 108 (continuously, regularly, and/or post-case) various types of data as it is acquired including patient information (e.g., name, gender, size, weight, age, height, medical history, etc.), physiological information (e.g., heart rate, oxygen saturation data, CO2 data, amongst others), treatment information (e.g., fraction of inspired oxygen, peak inspiratory pressure settings, tidal volume, minute volume, ventilation rate), and/or other relevant information. In various examples, the ventilator 302C may have functionality similar to that of the Z Vent® Ventilator, provided by ZOLL Medical Corporation, but other ventilators may be employed. The automated chest compressor 302A may also transmit (continuously, regularly, and/or post-case) certain types of data as it is acquired including patient information, physiological information, treatment information such as chest compression settings (e.g., depth, rate, duty cycle, etc.), and/or other relevant information. In certain examples, the automated chest compressor 302A may have functionality similar to that of the AutoPulse® chest compression device, provided by ZOLL Medical Corporation, but other suitable chest compression devices may be used. Similar to the defibrillator/monitor 302B, such devices may transmit a portion or all of the information collected to the server(s) 108 as medical device case files, each with their own identifying information. As a result, the information pertinent to the particular medical emergency may be grouped and consolidated together, with the original healthcare provider that started to the association having real-time access to the information, along with other appropriate personnel either located at or remote from the scene.

As shown in FIG. 3A, during an emergency medical event, the healthcare provider 118A employs the automated chest compressor 302A, the defibrillator/monitor 302B, and the ventilator 302C on a single patient (e.g., the patient 116 of FIG. 1). As discussed herein, the automated chest compressor 302A may be used to administer chest compressions to the patient according to specified compression depth and rate parameters, without requiring the healthcare provider to provide manual compressions. The defibrillator/monitor 302B may be connected to the patient via defibrillation electrodes and/or other patient sensors for collecting physiological information and to monitor the patient, for example, in assessing whether the patient is suffering from a life-threatening cardiac arrhythmia. The ventilator 302C may provide oxygen to the patient through an intubation tube or mask. Each of these medical devices 302A, 302B, 302C is configured to collect data relevant to the patient encounter and may upload this data, for further processing, to a large central repository of case files stored on the server(s) 108.

The healthcare providers 118A located at the scene of the patient encounter may further be using their respective mobile computing devices to generate other information, such as creating log entries of notable events through a documentation tool and/or entering in patient information via a charting tool for ePCR. Such records may also be uploaded along with the other medical device case files to the central repository of the server(s) 108. Normally, another user would have to sift through this repository of case files and match information from the various files with one another for further viewing, however, examples of the present disclosure allow for the case files pertinent to the particular patient encounter to be associated or otherwise linked together and consolidated into a single record, for viewing real-time, during and/or after the patient encounter.

For instance, as illustrated in FIG. 3A, the healthcare provider 118A located on scene uses the mobile computing device 104B executing an encounter device association application (e.g., a patient encounter device association application 150 of FIG. 1) to generate association information that may be used by the server(s) 108 to piece together the case files of the patient encounter. For example, the healthcare provider 118A can, before, during, or after the patient encounter, move from medical device to medical device to acquire representations of each medical device using a medical device interface included with the mobile computing device 104B. For instance, the healthcare provider 118A can scan (e.g., acquire an image of) a first quick response (QR) code affixed to the defibrillator/monitor 302B using a camera that is part of the mobile computing device 104B running the encounter device association application. Or, the healthcare provider 118A can position a near-field communication (NFC) reader included in the mobile computing device 104B executing the encounter device association application proximal to an NFC tag affixed to or housed within the defibrillator/monitor 302B to acquire a magnetic signature that identifies the defibrillator/monitor 302B. Next, the healthcare provider 118A can move to the automated chest compressor 302A and interact with the mobile computing device 104B executing the encounter device association application to scan a quick response (QR) code affixed to the automated chest compressor 302A. Or, the healthcare provider 118A can position the NFC reader included in the mobile computing device 104B executing the encounter device association application proximal to an NFC tag affixed to or housed within the automated chest compressor 302A to acquire a magnetic signature that identifies the automated chest compressor 302A. Lastly, as shown in FIG. 3A, the healthcare provider 118A can move to the ventilator 302C and position the NFC reader included in the mobile computing device 104B executing the encounter device association application proximal to an NFC tag affixed to or housed within the ventilator 302C to acquire a magnetic signature that identifies the ventilator 302C. Alternative to the NFC tag, the healthcare provider 118A can use the mobile computing device 104B executing the encounter device association application to scan a quick response (QR) code affixed to the ventilator 302C. It should be noted that the image and magnetic signature acquisition described above is quick and lightweight by design, as time is of the essence in some emergency patient encounters. In these situations, the healthcare provider 118A may not be able or willing to establish a robust, bi-directional, and fully authenticated network communication session with each medical device involved in a patient encounter. In addition, these lightweight communication mechanisms provide additional security to the medical devices, in that they cannot be utilized to hack the medical device due to the unidirectional communication and limited functionality they provide.

Alternatively or additionally, in some examples illustrated by FIG. 3A with combined reference to FIG. 1, the healthcare provider 118A can use the mobile computing device 104B executing the encounter device association application to acquire the representations of the identifiers of the medical devices by supplying appropriate input to a user interface provided by any of the event log application 140, the ePCR application 122, or either of the association generators 142A and 142B. In various examples, each of these programs is configured to receive input indicating a request to acquire a representation of an identifier of a medical device and to respond to such a request by controlling the medical device interface to scan for or otherwise obtain representations of identifiers. The QR codes scanned (or relevant identifying tags obtained) in this manner can be stored in association information along with a token identifying this particular patient encounter and timestamps that indicate the time at which the representations were acquired. Other information that can be stored in the association information includes a geotag indicating the geolocation of the mobile computing device 104B at the time of acquisition of each representation. After the association information is complete, the program responsible for its creation can store the association information locally (e.g., within local event log data, charting data, or as distinct association information) and/or transmit the association information to the server(s) 108 via an appropriate interface (e.g., the ePCR API 128 and/or the event log API 144) as distinct association information or in association with and/or embedded in charting data and/or event log data. It should be noted that the representations of the medical devices can be acquired at any time during a patient encounter or, in some case, even before or after the patient encounter. In some examples, the user provides a confirmation to the mobile computing device 104B to generate and transmit the association information to the appropriate server(s), for associating case files relevant to the particular patient encounter.

In some examples, after acquiring representations, converting them to data that identifies the medical devices 302A-302C, and receiving user confirmation, the mobile device 104B executing the encounter device association application generates association information (e.g., as illustrated in FIG. 2) and transmits the association information to the server(s) 108 via the network 112. In some examples, the mobile computing device 104B can receive from the server(s) 108 via the network 112, in real-time, an integrated data source encounter structure that includes information from medical device case files generated by the medical devices 302A-302C during their treatment of the patient 116. In these examples, the server(s) 108 providing the encounter data source integration service are configured to generate and transmit the integrated data source encounter structure automatically in response to reception of the association information.

In addition, as shown in FIG. 3A, the server(s) 108 can be configured to transmit the integrated data source encounter structure to the mobile computing device 104C to enable the healthcare provider 118B to provide support to the healthcare provider 118A, to prepare to receive the patient 116, and/or for telemedicine purposes. In some examples, the encounter review application 148 is configured to receive the integrated data source encounter structure from the server(s) 108 and provide the healthcare provider 118B with the integrated data source encounter structure via a user interface of the mobile computing device 104C. In at least some examples, the encounter review application 148 can include RescueNet® Code Review provided by ZOLL Medical Corporation. In some embodiments, the encounter review application 148 may be coincident with the encounter device association application, in that the same software application may be used to both generate association information and to review consolidated data of the integrated data source encounter structure.

In addition, examples of the present disclosure may allow for data generated from medical devices that are applied to the patient at different times during the emergency to be consolidated. FIG. 3B illustrates an example in which the emergency encounter is segmented into three distinct phases 315A, 315B, and 315C. In phase 315A, a patient (e.g., the patient 116), who is not currently in the hospital, suffers from a medical emergency, such as sudden cardiac arrest. In such a situation, it is rarely the case that a large swath of appropriate medical devices is immediately present. In fact, it is more likely that only a bystander 300 with very little medical experience is available to help. The bystander 300 may have the presence of mind to find a public access automated external defibrillator (AED) 302D, for example, stored in a nearby wall cabinet and to call emergency medical services (EMS). The bystander 300 may then apply defibrillation electrode pads to the victim and administer CPR, according to step-by-step instructions provided by the AED, examples of which may include the AED Plus® or ZOLL AED 3® public access AEDs, provided by ZOLL Medical Corporation. In some examples, the AED 302D may collect data such as ECG waveforms of the victim, number of defibrillation shocks provided, ECG snapshots associated with the defibrillation shocks, and chest compression performance information, and may upload such information to the server(s) 108 with associating capabilities, as further described herein.

Once EMS arrives in phase 315B, the healthcare provider 118A can use the mobile computing device 104 executing a patient encounter device association application to quickly acquire a representation of an identifier of the AED 302D (e.g., scan QR code identifier, obtain NFC or radio frequency identification (RFID) tag identifier) seeking to access the case data stored therein via the mobile computing device 104 according to the examples described herein. In addition, the healthcare provider 118A, who has more medical training, may employ a professional grade defibrillator/monitor 302B and attach ECG electrodes (e.g., 12-lead, 3-lead), along with other sensors such as blood pressure and SpO2 sensors, for more advanced care and physiological monitoring. Upon arrival, the more advanced defibrillator/monitor 302B may also collect data such as, for example, heart rate, ECG waveforms of the victim, number of defibrillation shocks provided, ECG snapshots associated with the defibrillation shocks, blood pressure readings/trends, oxygen saturation readings/trends, drug infusions, chest compression and ventilation performance information, amongst others. Such information may be uploaded to the appropriate server(s) 108 with associating capability on a continuous and/or regular basis as data is updated over time during the patient encounter. In accordance with aspects of the present disclosure, the healthcare provider 118A may use a mobile computing device 104 executing the encounter device association application to obtain identifiers (e.g., scanned QR/bar codes, acquisition via NFC connection or RFID) of the AED 302D and the defibrillator/monitor 302B, for the encounter data source integration service to associate the two devices and the corresponding case files/data containing the relevant patient and treatment information with the specific emergency event.

Figure 3D:
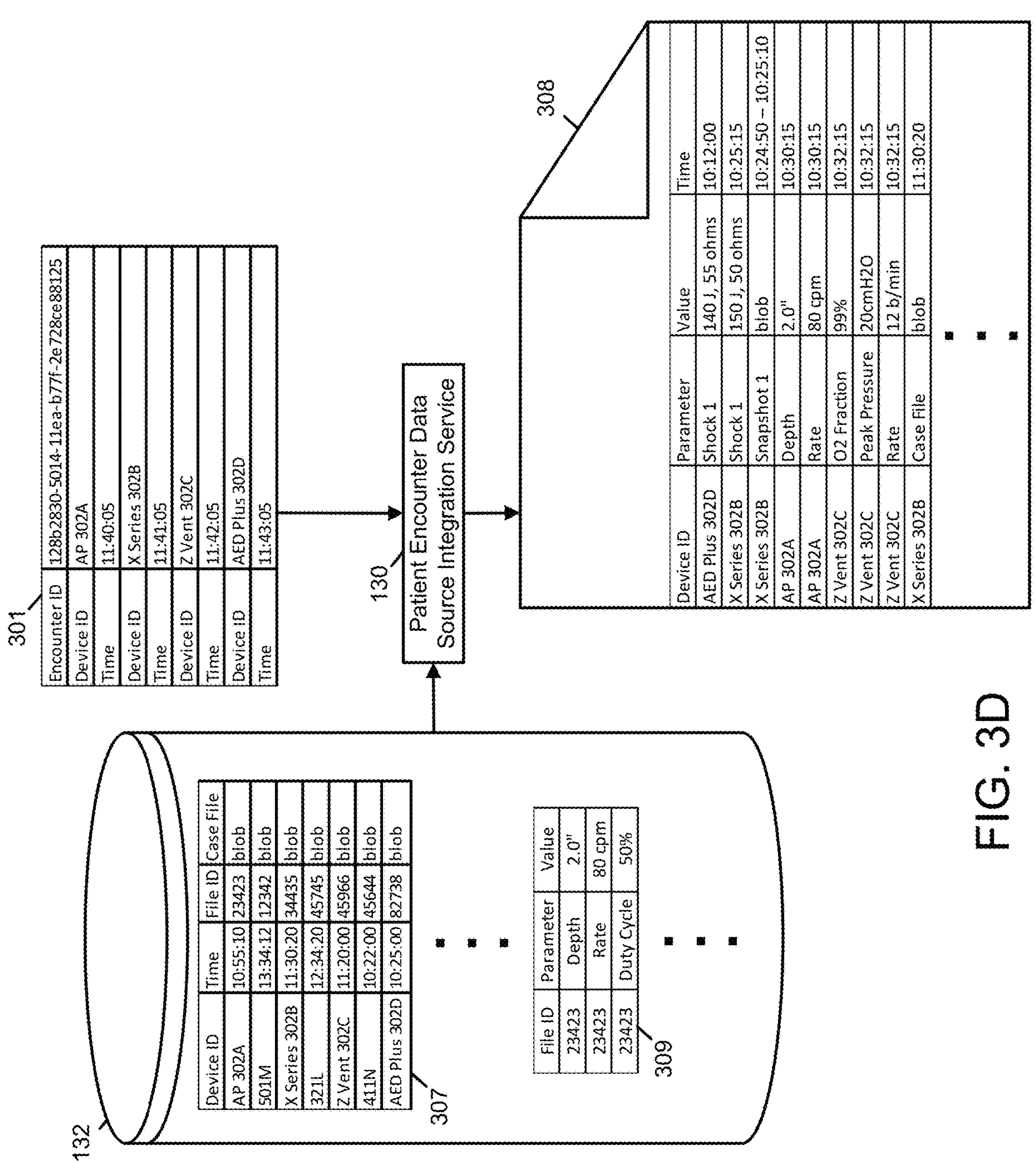
FIG. 3D is a data flow diagram illustrating the processing and flow of case data from the medical device case file data store of FIG. 3C to an integrated data source encounter structure.

In phase 315C, EMS may decide that the victim requires immediate hospital care, and thus may begin transport via an ambulance that is further equipped with the automated chest compressor 302A and the ventilator unit 302C for care en route to the hospital. As discussed herein, in various examples, the automated chest compressor 302A may provide chest compressions according to pre-specified parameters, and the ventilator unit 302C may monitor oxygen saturation and heart rate levels of the victim and administer automated ventilations, for example, with user assistance. The healthcare provider 118A may further use the mobile computing device 104A executing the encounter device association application to obtain identifiers (e.g., scanned QR/bar codes, acquisition via NFC connections) of the automated chest compressor 302A and the ventilator 302C, so that the encounter data source integration service is able to associate an additional two devices and the respective case files containing patient and treatment information with this particular emergency event. The healthcare provider 118A may further request using the mobile device 104 for the encounter data source integration service to associate together the information generated by the four separate devices for the particular emergency victim/event, where the server(s) 108 with associating ability can consolidate the medical data provided from the uploaded case files into an integrated data source encounter structure. The resulting integrated data source encounter structure may then include all of the pertinent data relating to the patient 116 who was treated by the bystander 300 and by EMS, and even further by the hospital (not specifically elucidated in this example) which may employ even more medical devices in the emergency. In various examples, this integrated data source encounter structure could be sent to the appropriate healthcare provider(s), located either in proximity or remotely from the victim, for real-time and/or post-case review. FIGS. 3C and 3D, which is described further below, illustrates an example flow of data in some of these examples.

More specifically, FIG. 3C is a data flow diagram that illustrates transmission and storage activities of some examples. As show in FIG. 3C, the medical devices 302A-304D each generate respective case files 304A-304D, which may be updated on a continuous and/or regular basis over the course of the patient encounter. Each of the case files 304A-304D includes case data generated by its associated medical device during an encounter with the patient 116, for example, as illustrated in FIGS. 3A and 3B. For example, the case file 304A stores case data recorded by the automatic chest compressor 302A. The case file 304A includes case data records that document an identifier of the automatic chest compressor 302A, events detected by the automatic chest compressor 302A, details regarding those events, and timestamps that indicate the time when each event was detected. As illustrated in FIG. 3C, the types of events that automatic chest compressor 302A detects and records in the case file 304A include start/power on events, end/power off events, and configuration of automated compression settings. The automated compression settings can include depth, rate, and duty cycle, among other settings. In various embodiments, the device 302A continuously updates the case file 304A as it acquires data, which is in turn uploaded to the server executing the patient encounter data source integration service.

Continuing with FIG. 3C, the case file 304B stores case data recorded by the defibrillator/monitor 302B, which may be updated on a continuous and/or regular basis over the course of the patient encounter. The case file 304B includes case data records that document an identifier of the defibrillator/monitor 302B, events and parameters detected by the defibrillator/monitor 302B, details regarding those events and parameters, and timestamps that indicate the time when each event or parameter was detected. As illustrated in FIG. 3C, the types of events and parameters that defibrillator/monitor 302B detects and records in the case file 304B include start/power on events, end/power off events, measurements of the patient's blood pressure (invasive and non-invasive), pulse oximetry of the patient (instantaneous and trends), end-tidal carbon dioxide readings of the patient (instantaneous and trends), therapy pad attachment events, information regarding the therapy pads attached to the patient, information descriptive of electrotherapeutic shocks delivered to the patient, data descriptive of manual CPR compressions delivered to the patient, data descriptive of manual ventilations administered to the patient, ECG snapshots descriptive of the patient's cardiac activity recorded proximal to (e.g., within 10 seconds before and after) an electrotherapeutic shock, a mode of operation (automatic or manual) of the defibrillator/monitor 302B, ECG information of the patient recorded independent of electrotherapeutic shock delivery, capnography information of the patient, and therapy pad detachment events. The ECG information and/or ECG snapshots may be used to create a 12-lead ECG report associated with defibrillator/monitor 302B. Accordingly, the patient record (e.g., that includes case file 304B) may include the 12-lead ECG report. The blood pressure measurement can be systolic and/or diastolic. The information regarding the therapy pads can include the make, model, type, and impedance of the therapy pads. The information descriptive of the electrotherapeutic shocks can include the number of joules delivered and the impedance encountered. The data descriptive of the manual compressions can include average depth and average rate. The data descriptive of the manual ventilations can include average tidal volume and average vent rate. In various embodiments, the device 302B continuously updates the case file 304B as it acquires data, which is in turn uploaded to the server executing the patient encounter data source integration service.

Continuing with FIG. 3C, the case file 304C stores case data recorded by the ventilator 302C, which may be updated on a continuous and/or regular basis over the course of the patient encounter. The case file 304C includes case data records that document an identifier of the ventilator 302C, events and parameters detected by the ventilator 302C, details regarding those events and parameters, and timestamps that indicate the time when each event or parameter was detected. As illustrated in FIG. 3C, the types of events and parameters that ventilator 302C detects and records in the case file 304C include start/power on events, end/power off events, configuration of ventilator settings, pulse oximetry of the patient (instantaneous and trends), end-tidal carbon dioxide readings of the patient (instantaneous and trends), and capnography information of the patient. The ventilation settings can include tidal volume, rate, peak inspiratory pressure, peak end-expiratory pressure, and fraction of inspired oxygen. In various embodiments, the device 302C continuously updates the case file 304C as it acquires data, which is in turn uploaded to the server executing the patient encounter data source integration service.

The case file 304D stores case data recorded by the AED 302D. The case file 304D includes case data records that document an identifier of the AED 302D, events and parameters detected by the AED 302D, details regarding those events and parameters, and timestamps that indicate the time when each event or parameter was detected. As illustrated in FIG. 3C, the types of events and parameters that AED 302D detects and records in the case file 304D include start/power on events, end/power off events, therapy pad attachment and detachment events, information regarding the therapy pads attached to the patient, information descriptive of electrotherapeutic shocks delivered to the patient. The information descriptive of the electrotherapeutic shocks can include the number of joules delivered and the impedance encountered.

In combination, the case files 304A-304D a chronology of care received by the patient 116 during the patient encounter. The case data stored in the case files 304A-304D is provided for purposes of illustration only, and the examples described herein are not limited to this or any other type of case data.

In some examples, each of the case files 304A-304D is parsed and imported into a case data store (e.g., the case data store 132 of FIG. 1). This parsing and importation process accounts for the many differences in format and content between the various case files 304A-304D and stores the case data included in the case files, and/or copies of the case files themselves, in the case data store. As shown in FIG. 3C, the case files and/or case data can be stored according to any of a variety of data types, models, and formats. Also as shown in FIG. 3C, the case data store can store case files and data from various other medical devices 306. While this standardized and centralized source of case files and data provides many advantages, the inclusiveness of the case data store also gives rise to a need for a mechanism to efficiently search for, and find, case files and data with particular commonalities of interest, such as case files and data having originated from a single patient encounter.

FIG. 3D is a data flow diagram that illustrates associating, integration/consolidation, and reporting activities of some examples. As illustrated in FIG. 3D, a patient encounter data source integration service (e.g., the patient encounter data source integration service 130 of FIG. 1) can be configured to utilize association information to search for, and find, case files and data generated during a particular patient encounter and stored within the case data store 311. The case data store 311 is one, non-limiting example of the case data store 132 of FIG. 1. As shown in FIG. 3D, the case data store 311 includes a table 307 that lists case files imported and stored in the case data store 311. This table stores identifiers of the medical devices that originated the case files, a timestamp information with the medical device case file, a unique identifier of the case file and a copy of the case file stored as a binary large object (blob). The case data store 311 also includes additional tables that store case data parsed from the case files for easy, rapid, and standardized access. Table 309 illustrates one example of such a table, which stores configuration setting used by an automated chest compressor, according to one example. Other table layouts and overall database schema can be used with the various examples disclosed herein, which are not limited to a particular approach to organizing case data.

As shown in FIG. 3D, the patient encounter data source integration service is configured to receive and parse association information 301. In these examples, the patient encounter data source integration service can be further configured to use the parsed association information (e.g., device identifiers and timestamps) to search for and identify, within the case data store 132, the medical devices involved in a patient encounter corresponding to, and identified by the association information. The patient encounter data source integration service can be further configured to associate case files generated by the identified medical devices to one another and to generate an integrated data source encounter structure 308 that includes case data from the various, associated, case files and/or copies of the case files themselves. Details of the operation of the patient encounter data source integration service 130 are provided further below, but as illustrated in FIG. 3D, the integrated data source encounter structure 308 generated in some examples includes at least a portion of the case data from each associated case file. Using this integrated data source encounter structure, healthcare providers, such as the healthcare provider 118C can review, for example, shocks administered while the patient 116 was being treated by the bystander 300, shocks administered while the patient 116 was being treated by the healthcare provider 118A on scene, and other treatment provided to the patient 116 while en route to a hospital.

FIGS. 3A-3D generally illustrate some examples of using a mobile device to identify multiple medical devices and receive data from the multiple devices that can be combined into an integrated case data report. However, it should be understood that other pre-generated data records and/or data reports may be received by any mobile computing devices on-scene with the patient 116, as well as by any remote mobile computing devices, such as those used by healthcare professionals at a hospital. Examples of such pre-generated data records include 12-lead ECG reports that may be generated by the defibrillator/monitor 302B. Generally, a 12-lead ECG report provides a picture of the electrical conduction within a patient's heart based on electrical measurements from 12 leads placed on the patient's body.

Six of the 12 leads are considered "limb leads" because they are placed on the arms and/or legs of the patient. The other six leads are considered "precordial leads" because they are placed on the torso (precordium).

The 12-lead ECG report may include electrical waveforms collected from each of the 12 leads on the patient. In some examples the 12-lead ECG report also includes one or more interpretations of the waveforms to provide fast and convenient analysis for the user. These one or more interpretations may involve pattern recognition from amongst the different waveforms, which may generate alerts or indicators if a particular portion of a waveform has an abnormal pattern suggesting some form of heart damage. In some examples, the 12-lead ECG report is one part of the integrated case data report, as described above.

Figure 19:
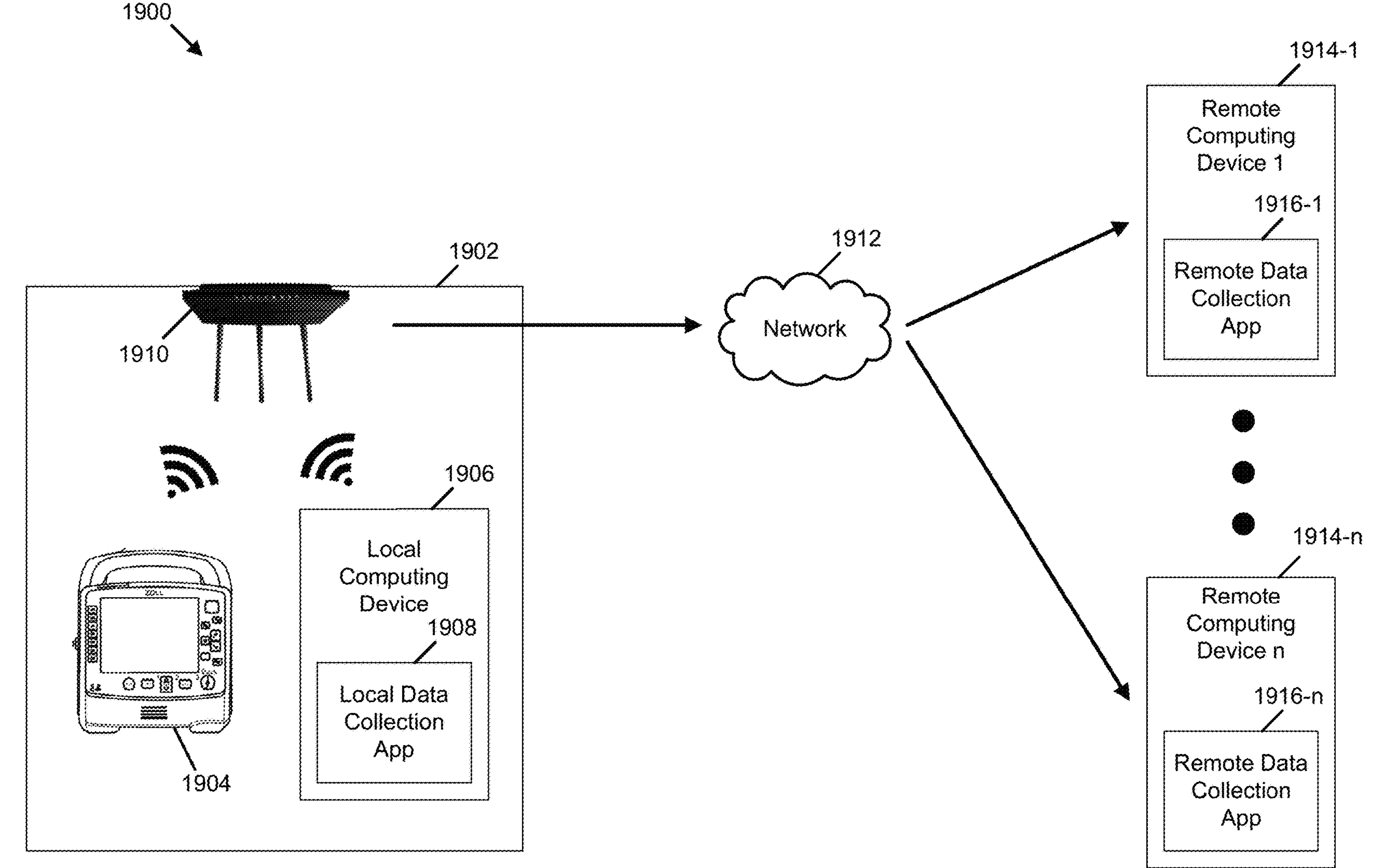
FIG. 19 is a schematic block diagram of a medical environment for transmitting data records, in accordance with at least one example disclosed herein.
Figure 20:
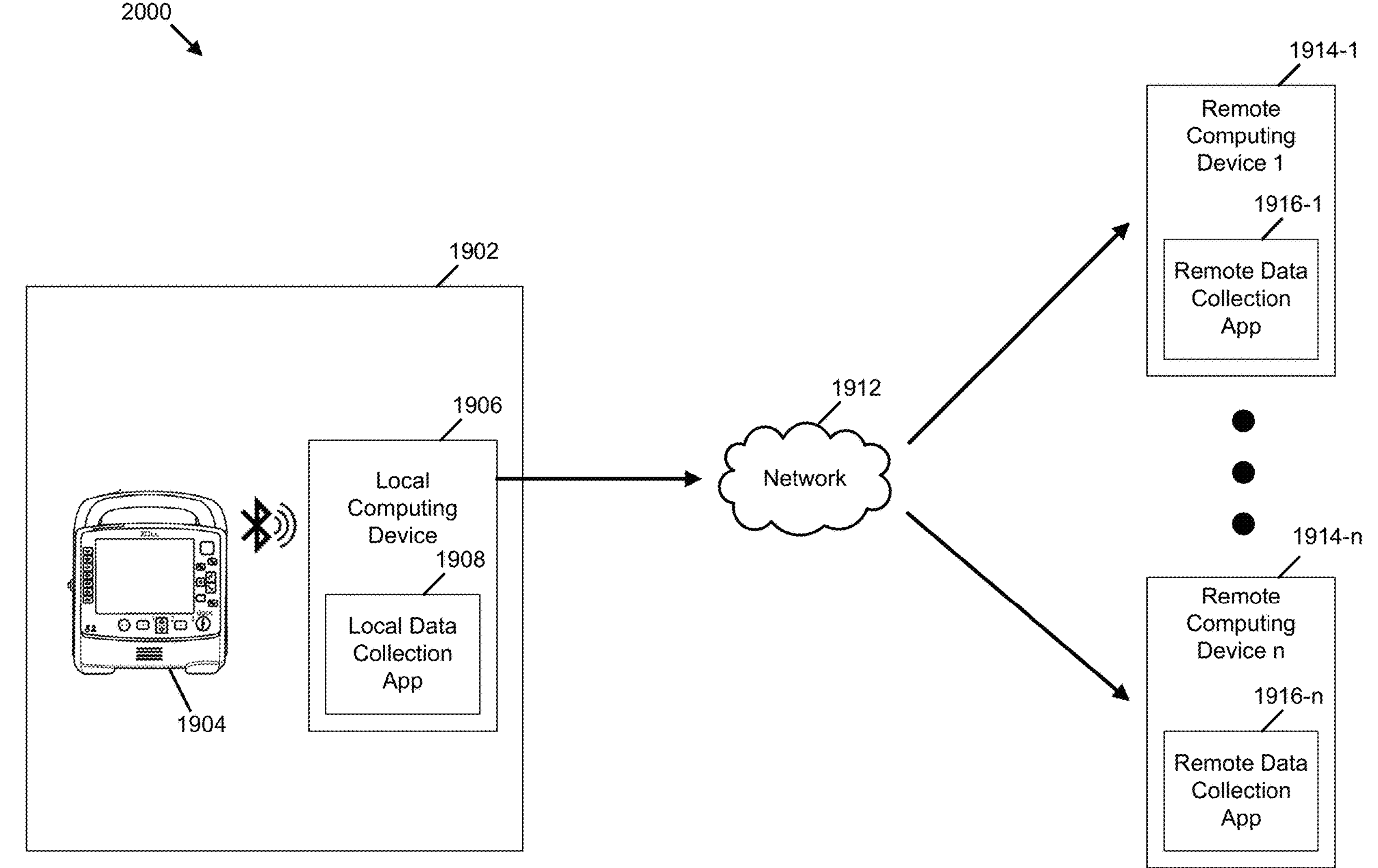
FIG. 20 is a schematic block diagram of another medical environment for transmitting data records, in accordance with at least one example disclosed herein.
Figure 21:
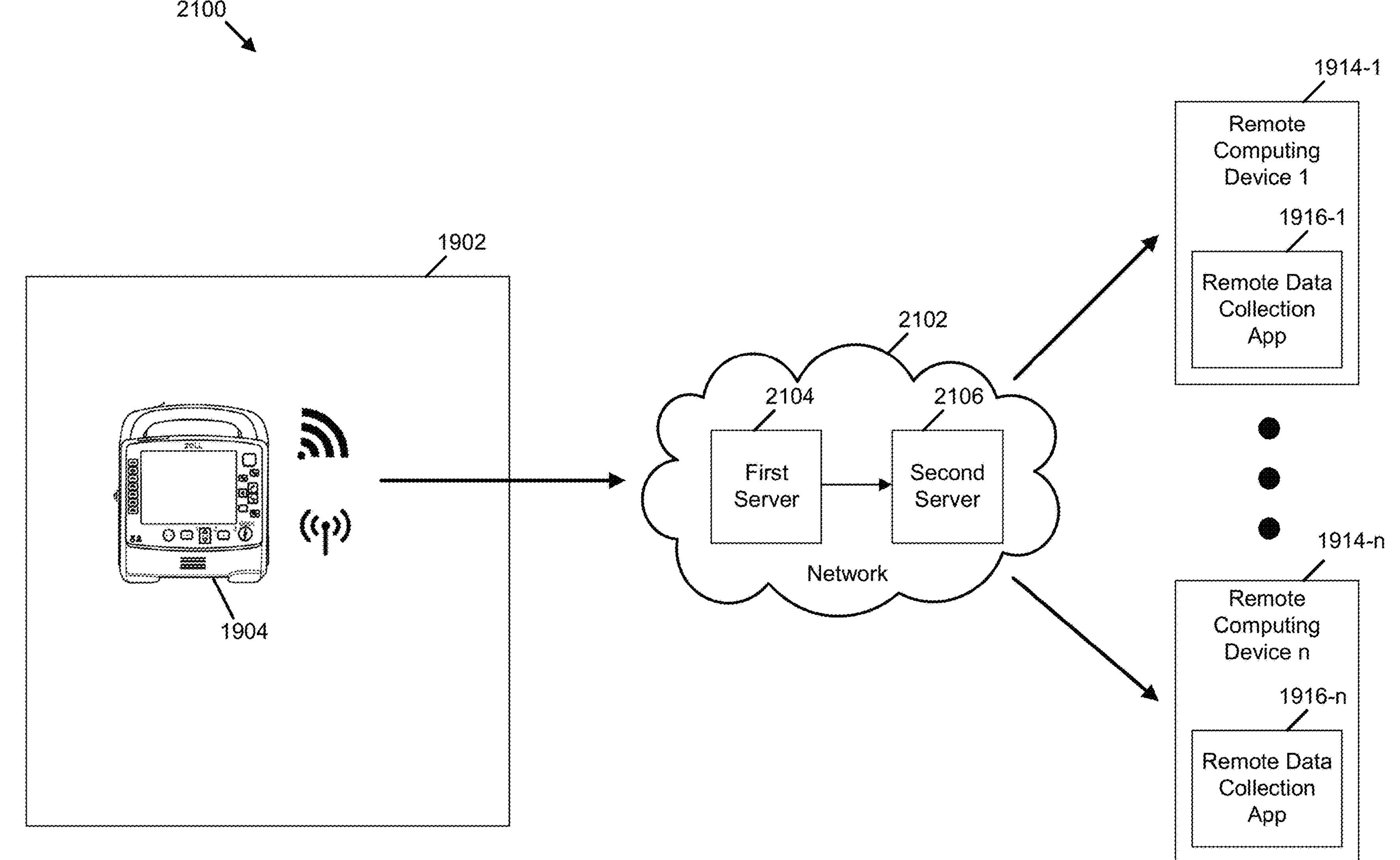
FIG. 21 is a schematic block diagram of another medical environment for transmitting data records, in accordance with at least one example disclosed herein.

FIGS. 19-21 illustrate example medical environments that involve communication of patient data between medical devices used at a particular location, such as an ambulance 1902, and the remote computing devices 1914. The data transfer may be facilitated by software applications installed on both local computing devices 1906 and remote computing devices 1914, as will be discussed in more detail herein. Example user interface screens for the software applications are discussed with reference to FIGS. 22-24.

FIG. 19 illustrates one example medical environment 1900 that involves wireless local area network (e.g., WIFI) communication of patient data between one or more medical devices and a local computing device 1906, and also the data communication with remote computing devices 1914. Any number of remote computing devices 1914 may receive medical-related data via the network 1912. In the illustrated example, n remote computing devices (labeled 1914-1 to **1914-*n*) are identified, each having a remote data collection application 1916-1 to 1916-*n*. Returning to the site where a patient may be located, a local computing device 1906 having a local data collection application 1908 is used to collect data from one or more local medical devices. In the illustrated example, a defibrillator/monitor 1904** has been set up to monitor a physiological state of a patient. The monitoring can involve the collection of various types of data, including collecting ECG data from a 12-lead measurement. An example of an appropriate defibrillator/monitor is the X Series® defibrillator/monitor, provided by ZOLL Medical Corporation, although other suitable defibrillator/monitor devices may be used in accordance with the present disclosure.

Any of the local computing device 1906 or the remote computing devices 1914 can include a tablet, smartphone, wearable device, and/or other mobile computing device and/or a combination of mobile devices that can execute applications described herein and communicate wirelessly with other communication devices over short-range or long-range wireless networks. The local computing device and/or the remote computing devices 1914 may have the same components as described above for the mobile computing devices 104A-104C. In some examples, the local computing device 1906 represents a tablet or smartphone used by a paramedic or other similar first-responder that is assisting a patient within the ambulance 1902 or at any location where the patient is. In some examples, the remote computing devices 1914 represent tables, smartphones, or PCs used by medical professionals at a remote location, such as at a hospital or clinic.

Data collected by the defibrillator/monitor 1904 may be formatted as a record or report to provide meaningful information to both local and remote users. In some examples, the defibrillator/monitor 1904 generates a 12-lead ECG report to provide waveforms and/or analysis of waveforms collected from a 12-lead apparatus. In the illustrated medical environment 1900, this report is transmitted via wireless communication protocol to a local wireless router 1910. Any other local computing devices having the local data collection app 1908 installed may also communicate wirelessly with the router 1910 to receive the 12-lead ECG report. In some examples, the 12-lead ECG report is encrypted to ensure confidentiality of the medical data and is decrypted at the mobile computing device 1906 using the local data collection app 1908 or stand-alone decryption software. Once received, the 12-lead ECG report may be viewed on the local computing device 1906. In some examples, the local data collection app 1908 also facilitates the transfer of the 12-lead ECG report to the one or more remote computing devices 1914 via the network 1912. For example, the 12-lead ECG report may first be transmitted via a wireless communication protocol to the router 1910, or to any other router in the vicinity of the local computing device 1906, and then transmitted from the router 1910 to the remote computing devices 1914 via the network 1912.

In some examples, the router 1910 is password-protected to ensure that only authorized devices can connect with router 1910 and receive data reports generated by the defibrillator/monitor 1904. For example, for the local computing device 1906 to communicate with the router 1910 to receive the data reports, it must first provide the requisite password to establish the wireless connection with the router 1904. Once the password is entered once, it may be remembered for future engagements such that it does not need to be entered again to establish the connection with the router 1910 when the local computing device 1906 is within range of router the 1910.

Although description above has primarily discussed the acquisition and transmission of a 12-lead ECG report, it should be understood that any measured patient parameters can be acquired and transmitted by the defibrillator/monitor 1904 to the local computing device 1906. Additionally, in some examples, any other measured patient parameters can be organized into one or more reports or records. Some examples of other measured patient parameters include respiration/breath rate, heart/pulse rate, blood-oxygen ($SpO_2$) saturation, methemoglobin (SpMET) saturation, carboxyhemoglobin (SpCO) saturation, end-tidal $CO_2$ ($ETCO_2$) value, fractional inspired carbon dioxide ($FiCO_2$) value, temperature, and invasive or non-invasive blood pressure. The transmitted data may include waveform snapshots of particular relevant events based on the measured data.

In some examples, data reports or records generated by the defibrillator/monitor 1904 are transmitted automatically to the local computing device 1906 upon being generated. In other words, there is no waiting for a request to be received for the data before transmitting it. Accordingly, any local computing devices having the local data collection app 1908 installed will receive any transmitted data reports or records generated by the defibrillator/monitor 1904 without any interaction required by the user. In some examples, a user may opt out of receiving the data reports or records using the local data collection app 1908.

In some examples, the network 1912 can include one or more communication networks through which the router 1910 and the remote computing devices 1914 can send, receive, and/or exchange data. In various implementations, the network 1912 can include a cellular communication network and/or a computer network. In some examples, the network 1912 includes and supports wireless network and/or wired connections. For instance, in these examples, the network 1912 may support one or more networking standards such as GSM, CMDA, USB, BLUETOOTH, CAN, ZigBee®, Wireless Ethernet, Ethernet, and TCP/IP, among others. The network 1912 may include both private networks, such as local area networks, and public networks, such as the Internet. It should be noted that, in some examples, the network 1912 may include one or more intermediate devices involved in the routing of packets from one endpoint to another. However, in other examples, the network 1912 can involve only two endpoints that each have a network connection directly with the other. In some examples, the network 1912 includes one or more server devices that may act as intermediary checkpoints for the medical data, records, or reports transferred from the router 1910 to the one or more remote computing devices 1914. For example, an ECG medical report related to a particular patient may be received by a server hosted in a secure domain. The server may store the received medical report as part of a larger medical record for the given patient that includes other data previously stored regarding the patient. The server may pass on either the received ECG medical report or the larger medical record to any of the one or more remote computing devices 1914.

In some examples, the remote computing devices 1914 include the remote data collection app 1916 to receive medical data, records, and/or reports via the network 1912. The remote data collection app 1916 may include much of the same functionality described above for the local data collection app 1908. For example, the remote data collection app 1916 may receive medical data measured from the defibrillator/monitor 1904 as a report or record that can be displayed to a user with minimal or no interaction required by the user. In some examples, the remote data collection app 1916 may provide an alert or notification to a user whenever a new data report is received. The alert may change depending on determined characteristics of the data report. For example, when a new 12-lead ECG data report is received, the alert may have an increased volume or a different tone to signify troubling patterns detected in one or more of the waveforms that demand immediate attention by the user. The troubling patterns may be detected using one or more pattern detection algorithms that compare the detected waveforms to predefined waveforms known to represent some form of heart damage or abnormality.

In some examples, the remote data collection app 1916 facilitates the storage of multiple data reports for one or more different patients and allows a user to access any of the stored data reports. Once selected, one or more of the data reports may be shown on a display associated with any of the remote computing devices 1914. For example, 12-lead ECG data reports may be periodically generated and timestamped based on the time of the creation. Each of these reports may be collected by the remote data collection app 1916 and listed for a user to select a particular 12-lead ECG data report to view. The listing may be sorted or organized based on the timestamp associated with each of the 12-lead ECG data reports.

In some examples, defibrillator/monitor 1904 generates a case file, such as case file 304B, that includes one or more 12-lead ECG reports. The full case file may then be received by local data collection app 1908 and ultimately transmitted to remote data collection app 1916. In some examples, one or more 12-lead ECG data reports generated by defibrillator/monitor 1904 are part of an integrated data source encounter structure as described, for example, with reference to FIG. 5.

FIG. 20 illustrates another example medical environment 2000 that involves local personal area network (e.g., BLUETOOTH network) communication of patient data between one or more medical devices and the local computing device 1906, and also data communication with the remote computing devices 1914. The local computing device 1906 having the local data collection application 1908 is used to collect data from one or more local medical devices, such as the defibrillator/monitor 1904.

The medical environment 2000 is similar to the medical environment 1900 described with reference to FIG. 19, however, one difference lies in how the medical data reports are transferred between the defibrillator/monitor 1904 and the local computing device 1906, and between the local computing device 1906 and the remote computing devices 1914. In the medical environment 2000, medical data, reports, and/or records measured/generated by the defibrillator/monitor 1904 are transferred to the local computing device 1906 via a secure personal area network connection. In some examples, the defibrillator/monitor 1904 generates a 12-lead ECG report to provide waveforms and/or analysis of waveforms collected from a 12-lead apparatus. Any other local computing devices having the local data collection app 1908 installed may also communicate wirelessly via the personal area network to receive the 12-lead ECG report. In some examples, data reports or records generated by the defibrillator/monitor 1904 are transmitted automatically to the local computing device 1906 upon being generated. In other words, there is no waiting for a request to be received for the data before transmitting it. In some examples, the 12-lead ECG report is encrypted to ensure confidentiality of the medical data and is decrypted at the local computing device 1906 using the local data collection app 1908 or stand-alone decryption software. Once received, the 12-lead ECG report may be viewed on the local computing device 1906. In some examples, a pairing process between the local computing device 1906 and the defibrillator/monitor 1904 must first be performed to establish the personal area network connection. This pairing process may involve manually accepting the connection with the local computing device 1906 on the defibrillator/monitor 1904.

In some examples, the local data collection app 1908 also facilitates the transfer of the 12-lead ECG report to the one or more remote computing devices 1914 via the network 1912. This data transfer may occur using long-range wireless communication, such as cellular communication, between the local computing device 1906 and the network 1912.

FIG. 21 illustrates another example medical environment 2100 that involves direct communication between one or more medical devices and the remote computing devices 1914 via a network 2102. Unlike the example medical environments 1900 and 2000, the medical environment 2100 does not involve computing devices local to the defibrillator/monitor 1904 in the transfer of medical data, records, or reports measured/generated by the defibrillator/monitor 1904.

In some examples, the defibrillator/monitor 1904 uses one or both of short-range and long-range communication to transfer medical data via the network 2102 to the remote computing devices 1914. Example short-range communication technologies include BLUETOOTH or WIFI while example long-range technologies include cellular communication.

In some examples, the network 2102 shares the same characteristics described above for the network 1912. In the illustrated example, the network 2102 includes at least a first server 2104 and a second server 2106. In some examples, the first server 2104 is configured to receive medical data, records, and/or reports from the defibrillator/monitor 1904 and provides a gateway of sorts for collecting and organizing the data. In some examples, the first server 2104 is hosted on a secure network. The first server 2104 may hand off the received medical data, records, and/or reports to the second server 2106, which disseminates the received data, records, and/or reports to the remote computing devices 1914. In some examples, the first server 2104 may be a centralized data server configured to receive medical data from a plurality of different medical devices operated by different hospital networks, and the second server 2106 may be a server hosted on a particular hospital network and designed to transmit the received medical data, records, and/or reports to the remote computing devices 1914 that are a part of the particular hospital network.

In some examples, the first server 2104 sends the received medical data, records, and/or reports out to an email distribution list stored within the first server 2104. The distribution list may be updated and modified to add or delete particular email addresses that are to receive data associated with a particular the defibrillator/monitor 1904. In some examples, individual email addresses in the distribution list may be configured to receive only particular types of data reports (such as only receiving 12-lead ECG reports), or only receiving data reports generated during a particular timeframe. In some examples, different distribution lists may be created having one or more associated account codes. Each of the account codes may be related to one or more defibrillator devices or to a particular hospital network.

In the example medical environments described above, medical reports such as 12-lead ECG reports are generated by the defibrillator/monitor 1904. However, in some examples, medical data is collected by the defibrillator/monitor 1904 and transferred to the local computing device 1906, and the local computing device 1906 generates a medical report based on the received data. The medical report may be generated using the local data collection app 1908. In some other examples, medical reports are generated by any of the one or more remote computing devices 1914 after receiving the medical data either directly from the defibrillator/monitor 1904 or from the local computing device 1906. The medical report may be generated using the remote data collection app 1916.

Figure 22:
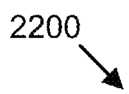
FIG. 22 is a view of a user interface screen provided by a local data collection application in accordance with at least one example disclosed herein.
Figure 22:
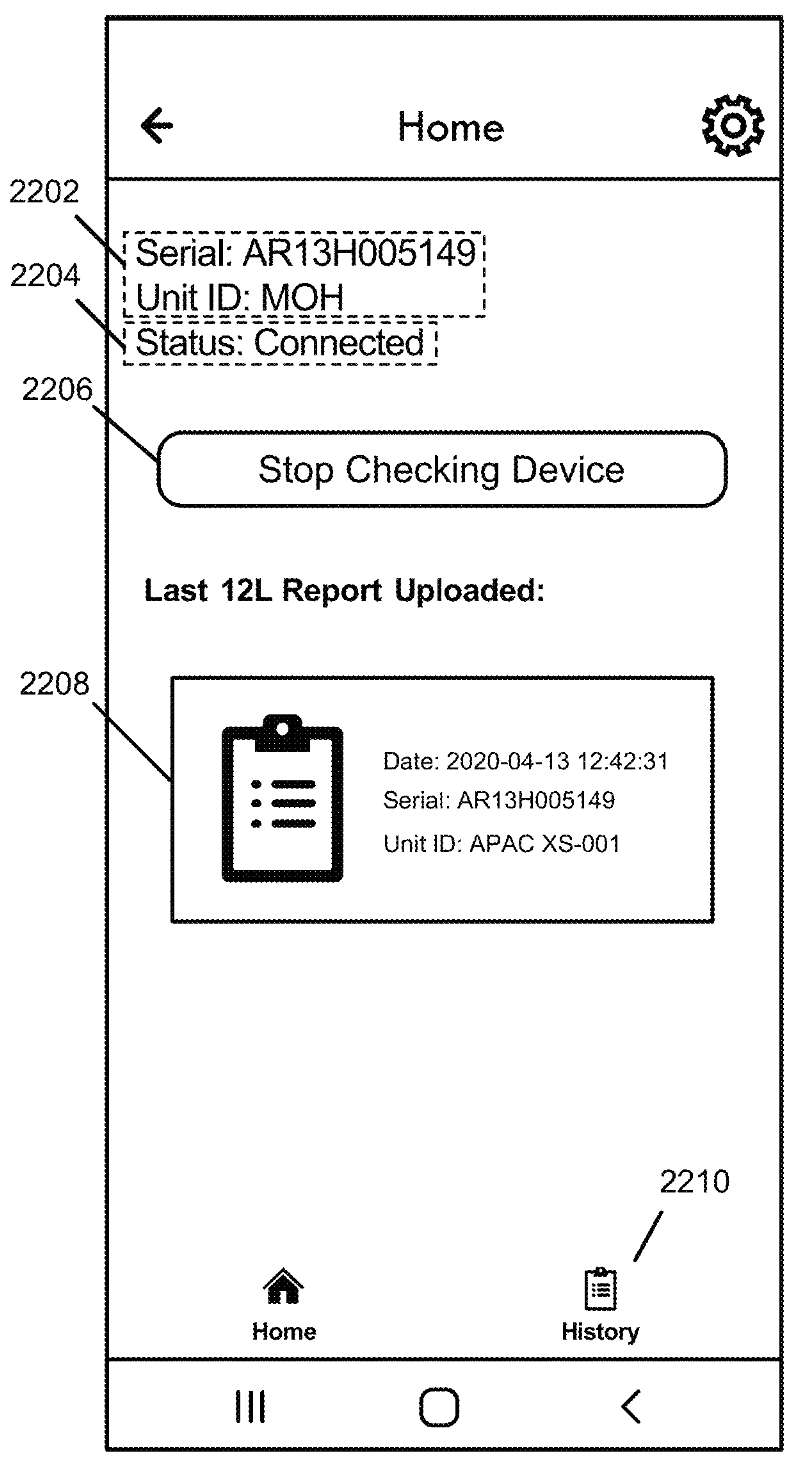

FIG. 22 illustrates an example user interface screen 2200 that is part of the local data collection app 1908. The user interface screen 2200 may be presented to a user on any type of display device and allows for a user to interact, via for example a touch interface, with the data being collected from the defibrillator/monitor 1904. Additionally, the user interface screen 2200 presents an example interface for viewing data records, such as ECG records, collected from the defibrillator/monitor 1904. It should be understood that the relative size and placement of the various regions and/or graphical objects on the user interface screen 2200 may be different than the particular illustrated example. In some examples, user interface screen 2200 provides a dedicated interface for the purpose of immediately presenting newly acquired data reports. The data reports appear on the screen as they are received, and in a listed order as more and more reports are received. In some examples, the list of received data reports can be scrolled through, sorted, or filtered.

The user interface screen 2200 displays information regarding a given medical device that it is receiving data from. For example, a region 2202 may include details like name, serial number, and/or unit ID for a given medical device, such as the defibrillator/monitor 1904. The user interface screen 2200 may include tabs in some examples to switch between different medical devices that are in the vicinity of the local computing device 1906. Accordingly, the region 2202 may include descriptive details regarding the current medical device for which data is being displayed. In some examples, a status indicator 2204 is provided to indicate whether a successful connection has been established with the medical device indicated in the region 2202.

In some examples, the user interface screen 2200 includes a button 2206 that is used to halt any polling for further data from the medical device. For example, the default setting when establishing a connection with a given medical device is to continuously check for new data from the medical device and receive any new data being transmitted from the given medical device. The button 2206 in essence allows a user to opt out from receiving any further medical data, records, or reports from the given medical device.

In some examples, the user interface screen 2200 includes a data report 2208 received from the given medical device. In some examples, a list of data reports may be provided in chronological order from when they are received. In some examples, the list of data reports may be sorted by time, name, or user-defined characteristics within the reports. As seen in the illustrated example, the displayed data report may include some descriptive details such as the date and time that the report was generated, a serial number associated with the medical device that generated the report and a unit ID of the medical device. In some examples, a user may click on or touch the displayed data report 2208 to view the report in further detail.

In some examples, a history button 2210 may be provided to access archived data reports generated by the given medical device. The archived reports may be organized by patient or by given time periods of data collection. For example, 12-lead ECG medical reports may be organized by the day or week that they were collected.

Figure 23B:
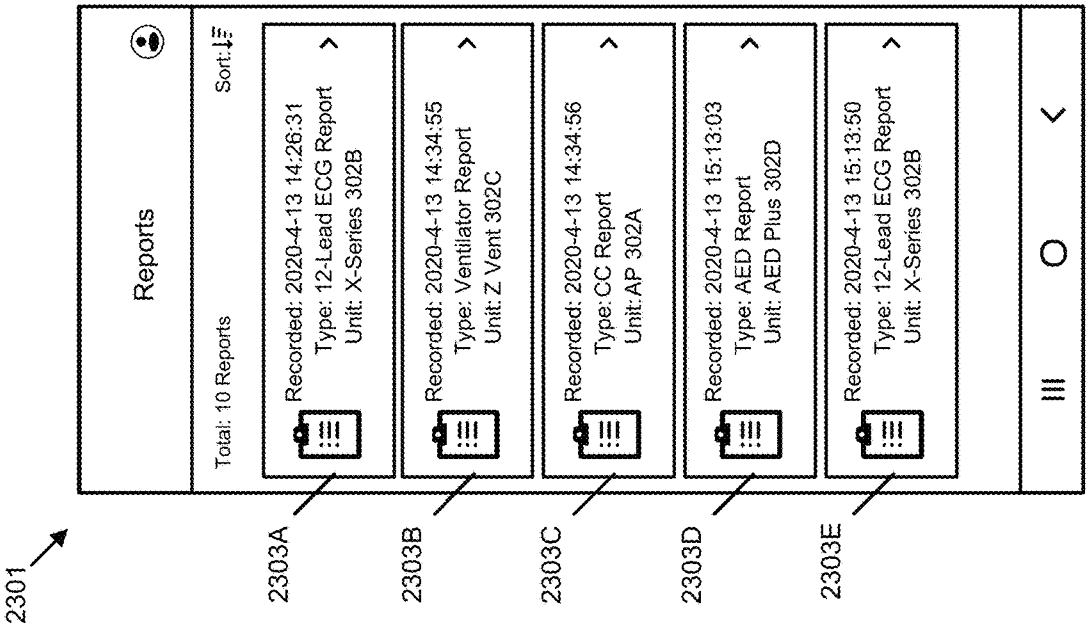
FIGS. 23A, 23B, and 24 are views of user interface screens provided by a remote data collection application in accordance with at least one example disclosed herein.
Figure 23A:
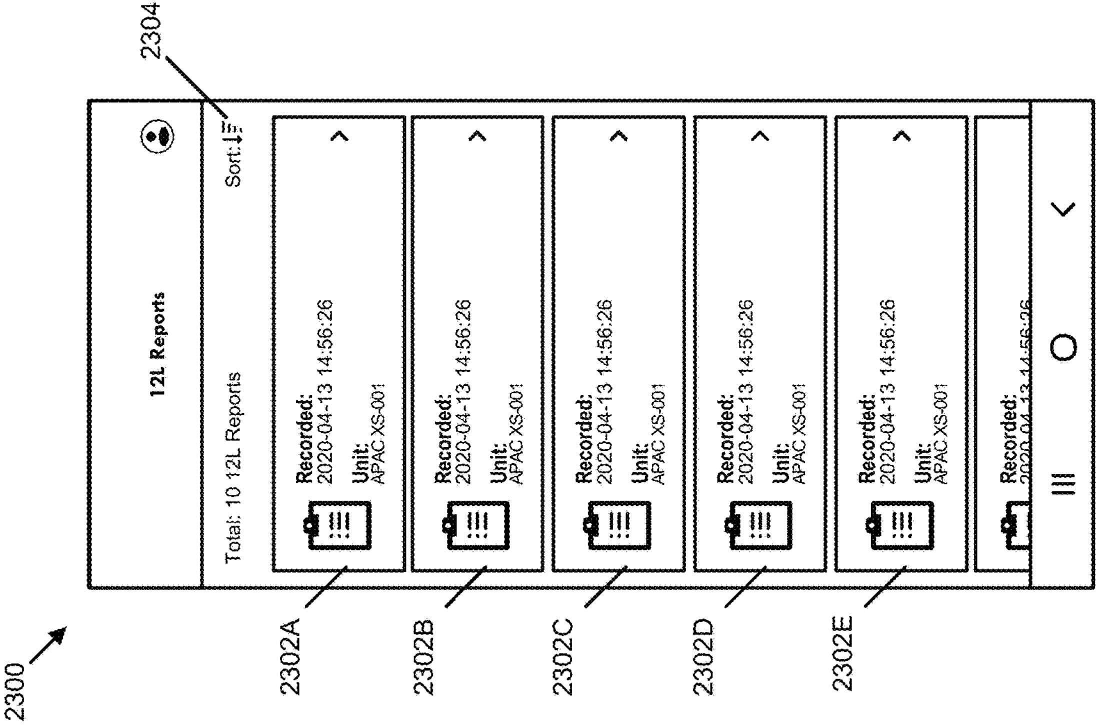

FIG. 23A illustrates an example user interface screen 2300 that is part of the remote data collection app 1916. The user interface screen 2300 may be presented to a user on any type of display device and allows for a user to interact, via for example a touch interface, with the data being collected from the defibrillator/monitor 1904. Additionally, the user interface screen 2300 presents an example interface for viewing data records, such as 12-lead ECG records, collected from the defibrillator/monitor 1904. It should be understood that the relative size and placement of the various regions and/or graphical objects on the user interface screen 2300 may be different than the particular illustrated example.

The user interface screen 2300 includes controls 2302A-2302E for accessing a plurality of received data reports collected from a given medical device, according to some examples. Although five 12-lead ECG data reports are illustrated, any number of data reports can be listed and scrolled through. For ease of discussion herein, any of the controls 2302A-2302E for accessing data reports may be identified with the more general label 2302. Each of the listed data reports may include some descriptive details such as the date and time that the report was generated, a serial number associated with the medical device that generated the report and a unit ID of the medical device. In some examples, the controls 2302 may be listed in chronological order of receipt of their corresponding data reports. In some examples, the controls 2302 may be sorted and/or filtered by time, name, or user-defined characteristics within their corresponding reports by activating a sort button 2304. In some other examples, the controls 2302 may be sorted and/or filtered based on the medical device that generated their corresponding reports, based on a given patient, or any other user-defined criteria.

In some examples, the data reports come from any number of different medical devices. Accordingly, the reports can include different types of data depending on the device that generated them. For example, some of the data reports may be from a defibrillator/monitor (such as defibrillator/monitor 302B), some data reports may be from a ventilator (such as ventilator 302C), and some data reports may be from an automated chest compressor (such as automated chest compressor 302A). FIG. 23B illustrates another example user interface screen 2301 that is part of the remote data collection app 1916. User interface screen 2301 presents an example interface with controls 2303A-2303E for viewing data reports collected from different medical devices associated with the same patient encounter. Such data reports received from different medical devices may be listed separately (as shown in FIG. 23B), or they may be combined into an integrated data source encounter structure (using, for example, a patient encounter data source integrated service 130 as described in FIG. 3D), and different ones of integrated data source encounter structures are listed instead. In the illustrated example, data reports have been received at different times from medical devices 302A-302D as described with reference to FIGS. 3B and 3C.

Figure 24:
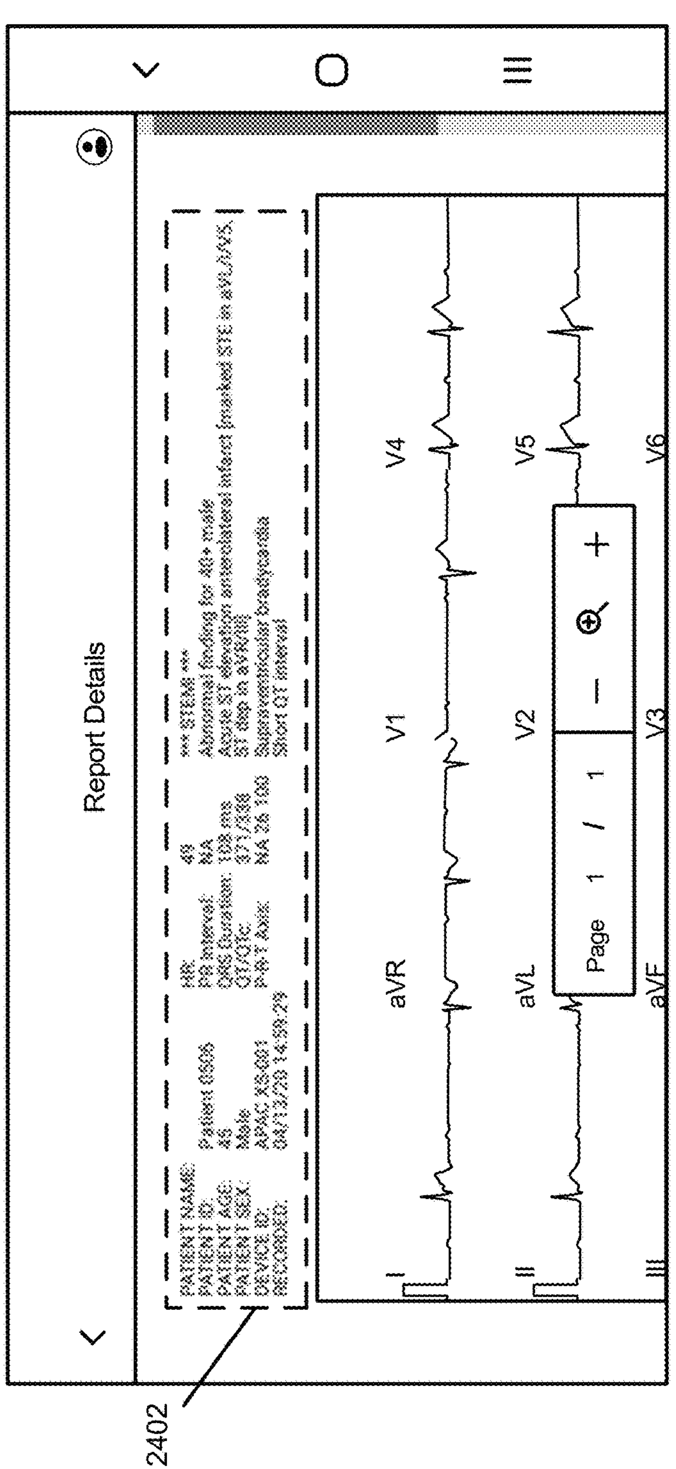

FIG. 24 illustrates another example user interface screen 2400 that is part of the remote data collection app 1916. The user interface screen 2400 provides an example view of a given data report 2302 after it has been selected, for example, from the user interface screen 2300. Selection of a given data report 2302 may change the view to show the details of the report to the user. In the illustrated example of the user interface screen 2400, a 12-lead ECG report has been selected and the details of the report are shown.

In some examples, the user interface screen 2400 includes a patient details region 2402 that includes various detailed regarding the patient associated with the medical report. As seen in the example, the patient's details may include the patient's name, patient ID, age, and sex. Further medical details ascertained from the medical device may be provided as well, such as the patient's heart rate, PR interval, QRS duration, QT/QTc, and P-R-T axis. In some examples, the patient details region 2402 also includes notes that have been added to the medical report from another caregiver, such as from a user of the local data collection app 1908 at the scene with the patient.

In some examples, the user interface screen 2400 displays particular waveforms from various leads of a 12-lead ECG measurement. For example, waveforms collected from each of the V1-V6, I, II, III, aVR, aVL, and aVF leads may be displayed. The data may be presented in a landscape view as illustrated in FIG. 24.

Figure 25:
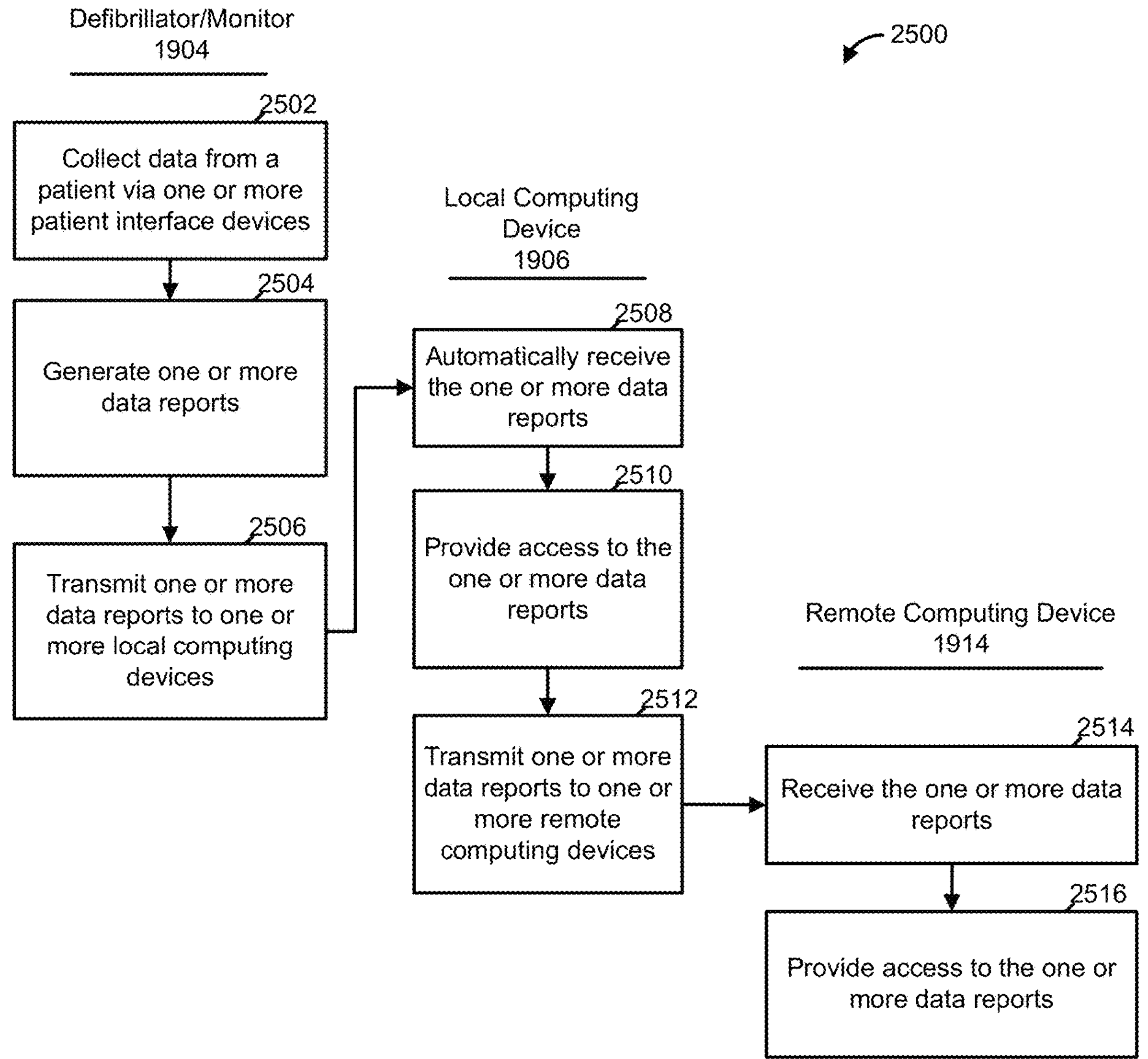
FIG. 25 is a flow diagram of data record transmission between local and remote devices in accordance with at least one example disclosed herein.

In some examples, devices from any of medical environment 1900, 2000, or 2100 are configured to execute a variety of processes that transmit and receive medical data records, such as ECG records or integrated data source encounter structures. FIG. 25, for instance, illustrates a data record transmission process 2500 that is executed by a medical device (e.g., defibrillator/monitor 1904 of FIG. 19), one or more local computing devices (e.g., local computing device 1906 of FIG. 19), and one or more remote computing devices (e.g., remote computing device 1914 of FIG. 19). In some examples, the operations attributed to the one or more local computing devices in FIG. 25 are executed by one or more local data collection apps (e.g., the local data collection app 1908 of FIG. 19) hosted by the one or more local computing devices.

Data record transmission process 2500 begins with collecting 2502 data from a patient using the medical device, in accordance with some examples. The data may be collected via one or more patient interface devices (e.g., physiological sensors, ECG sensors, SpO2 sensors, capnography sensors, blood pressure sensors, etc.) as described with reference to FIGS. 1 and 18. In some examples, the patient interface device includes 12-lead ECG sensors for collecting a 12-lead ECG of the patient.

After collecting the patient data, the medical device generates 2504 one or more data reports, such as a 12-lead ECG report. The 12-lead ECG report may include electrical waveforms collected from each of the 12 leads on the patient. In some examples the 12-lead ECG report also includes one or more interpretations of the waveforms to provide fast and convenient analysis for the user. These one or more interpretations may involve pattern recognition from amongst the different waveforms, which may generate alerts or indicators if a particular portion of a waveform has an abnormal pattern suggesting some form of heart damage. In some examples, the one or more data reports include at least one case file, such as case file 304B, that includes 12-lead ECG data. The case file may be one case file of an integrated data source encounter structure. Accordingly, data reports may be generated from a plurality of medical devices and combined to create the integrated data source encounter structure as generally discussed with reference to FIGS. 3C and 3D.

The medical device transmits 2506 one or more data reports (which may be included in one or more case files or integrated data source encounter structures) to one or more local computing devices. In some examples, data reports or records generated by the medical device are transmitted automatically (pushed) to the one or more local computing devices upon being generated. In other words, there is no waiting for a request (e.g., a poll) to be received for the data before transmitting it. Accordingly, any local computing devices configured to receive the data via, for example, the local data collection app, will automatically receive 2508 any transmitted data reports or records generated by the medical device without any interaction required by the user. In some examples, a user may opt out of receiving the data reports or records using the local data collection app. For example, the local data collection app can receive an input from the user that ceases automatically receiving any further data reports from a given medical device or from any medical devices. The medical device may transmit the one or more data reports using any known wireless communication interface such as WIFI, BLUETOOTH, or cellular. In some examples, the received one or more data reports are decrypted by the local computing device.

Any of the one or more local computing devices can provide access 2510 to the one or more received data reports. In some examples, access to the one or more received data reports includes viewing the contents of one or more integrated data source encounter structures. This access may include displaying a list of received reports along with the medical device they were received from. The displayed list may be automatically updated with any received data reports at the time that they are received. The list of reports may be sorted using various criteria such as by time received, time report was generated, medical device that transmitted the report, or certain parameters present in the medical report. According to some examples, at least one of the data reports is a 12-lead ECG report. An example of a user interface screen for providing one or more received data reports via a local computing device is illustrated in FIG. 22.

The local computing device is also configured to transmit 2512 any of the one or more received data reports to one or more remote computing devices. This data transmission may occur via any number of wireless pathways as generally illustrated in the medical environment 1900 or 2000. In some examples, the one or more received data reports are transmitted directly by the local computing device via cellular communication via a network, such as network 1912 from FIG. 19. In some examples, the one or more received data reports are transmitted across the network via a router within range of the local computing device. Regardless of the transmission technique used, one or more remote computing devices receive 2514 the one or more data reports, which may include at least one 12-lead ECG report.

The one or more remote computing devices are configured to provide 2516 access to the one or more data reports. In some examples, access to the one or more received data reports includes viewing the contents of one or more integrated data source encounter structures. The one or more remote computing devices may display a list of received reports along with the medical device or local computing device they were received from. The list of reports may be sorted using various criteria such as by time received, time report was generated, medical device that transmitted the report, or certain parameters present in the medical report. According to some examples, at least one of the data reports is a 12-lead ECG report. Example user interface screens for providing one or more received data reports via a remote computing device are illustrated in FIGS. 23 and 24.

Returning to FIG. 1, In some examples, the healthcare providers 118A and 118B can each be associated with the mobile computing devices 104 by, for example, being authenticated to an operating system and/or patient encounter device association application 150 executing on the mobile computing devices 104. As illustrated in FIG. 1, in some examples the mobile computing devices 104 may be configured to communicably coupled to the medical devices 102, although in some examples of the present disclosure, the mobile computing devices 104 are not necessarily in direct communication with the medical devices 102 but rather, the mobile computing devices 104 and the medical devices 102 are separately in communication with the server(s) 108 through the network 112.

In some examples, the mobile computing device 104A may be a device used by the healthcare provider 118A to generate the ePCR and/or other records and/or notes about the condition of the patient 116 and/or treatments applied to the patient 116. Similarly, in some examples, the mobile computing device 104B may be a device used by the healthcare provider 118A to generate an event log documenting specific treatment procedures (e.g., execution of a cardiac code) applied to the patient 116 such as the RescueNet® CodeWriter documentation mobile application, provided by ZOLL Medical Corporation, which allows for documentation of critical information of a code in an easy, intuitive manner. Although the ePCR application 122 and the event log application 140 are hosted by distinct mobile computing devices 104 in FIG. 1, the examples disclosed herein are not limited to this configuration. For instance, in some examples, a single mobile computing device 104 hosts both the ePCR application 122 and the event log application 140.

In some examples, the event log application 140 is configured to provide a set of user interface screens that are tailored to easily, quickly, conveniently, and accurately record events and sometimes determine additional event details encountered during the emergency medical treatment. These interface screens can be provided, for example, via a touchscreen of the mobile computing device 104 executing the event log application 140.

More specifically, in some examples, the event log application 140 is configured to provide screens including controls that are labeled and associated with events commonly encountered during emergency medical treatment. For instance, events such as administration of CPR, epinephrine (EPI), and/or electrotherapeutic shocks are commonly encountered while running a code blue and examples directed toward documenting a code blue have controls dedicated to recording these events. Many of these processes culminate in the storage of a date/time stamped entry that documents occurrence of specific events in an event log. The event log, in turn, documents the treatment provided to a patient and/or events that have occurred during the course of a patient encounter.

In some examples, the event log application 140 is further configured to respond to input selecting a control by executing a process that is associated with the control. For instance, in some examples, controls associated with administration of CPR, EPI, and shocks include timers and/or counters that are reset and/or incremented via execution of the process associated with the control. Further these processes can provide notifications after a threshold amount of time has elapsed since the control was last selected. For instance, the event log application 140 can provide, via the CPR control, a notification (e.g., flashing icon, color change, textual prompt) after 2 minutes has passed since CPR chest compressions were started or after 10 seconds has elapsed since CPR was paused. This notification after a predefined period of time, typically 2 minutes, of chest compressions is to remind the user that an interval of CPR has passed and that another phase in treating the patient may be required, such as a period of ECG analysis to determine whether the patient is in need of electrotherapy (e.g., defibrillation shock) or a short pause for one or more positive pressure ventilation breaths to be applied. Once this pause (e.g., for ECG analysis and/or ventilations) has passed, then chest compressions should immediately resume. Accordingly, the notification after 10 seconds of a pause in chest compressions may be appropriate to remind the user that chest compressions should resume. Similarly, in some examples, the event log application 140 can provide, via the EPI control, a notification after 3 minutes has passed since EPI was last administered. Such a notification may be appropriate to remind the user that a subsequent dosage of EPI is to be administered. These notifications can include causing the control to flash, become highlighted, change color, prompt with text, and/or provide another visual indication. Or, in some cases, an audible and/or haptic notification may be provided by the mobile computing device.

In some examples, to further ease treatment documentation in specific situations, the event log application 140 is configured to provide controls that enable a healthcare provider to change the documentation mode of the event log application 140 to either adult mode or pediatric mode. While operating in adult mode, the event log application 140 alters features of certain screens and controls to facilitate log entries that mark events directed to events encountered when treating an adult. For instance, controls associated and labeled with approaches to CPR that are only available to adults are visible only while the event log application 140 is operating in adult mode. Conversely, while operating in pediatric mode, the event log application 140 alters features of certain screens and controls to facilitate log entries that mark events directed to events encountered when treating a child. For instance, controls associated with approaches to CPR that are only available to children are visible only while the event log application 140 is operating in pediatric mode.

In certain examples, the event log application 140 is configured with controls to display a variety of information before, during, and after emergency treatment of a patient. For instance, in some examples, once the appropriate connections are made to acquire the relevant information, the event log application 140 is configured to display patient identification information to the healthcare provider via a patient information screen. Further, in at least one example, the event log application 140 is configured to display CPR quality metrics (e.g., chest compression metrics such as percentage of chest compressions that fall within a target depth, percentage of compressions that fall within a target rate, an average depth of compressions, an average rate of compressions, etc.) to the healthcare provider via a screen of the user interface. Further, in some examples, the event log application 140 is configured to provide screens with controls to receive MEWS factors and display MEWS scores calculated based on the MEWS factors. Further these screens may include a control that responds to input selecting the control by calling a rapid response or code team to, for example, the location of the mobile computing device.

The ePCR application 122 can render visual, audio, haptic, and/or tactile content, including content relating to ePCR generation. Thus the ePCR application 122 can receive input or provide output, thereby enabling a user to interact with the mobile computing device 104. The ePCR application 122 can be configured to receive charting data via various mechanisms, including, but not limited to, touchscreen, voice recognition, and scanner. For example, a patient may say his/her name and the ePCR application 122 can capture the patient name and store it as a portion of charting data. The ePCR application 122 can include a camera/scanner through which patient's driver license may be acquired/scanned and relevant information about the patient, such as name, address, age, can be stored as charting data. The healthcare provider 118A may dictate data or findings when examining the patient 116 via the ePCR application 122. Such dictation can be captured and saved as charting data, according to some examples. In certain examples, the ePCR application 122 utilizes the input devices 444 and/or the output devices 430 of FIG. 18.

In some examples, the ePCR application 122 implemented by a mobile computing device 104 can interoperate with a touchscreen and/or a flat panel PC or some other user interface hardware and a software stack configured to drive the hardware. Portions of the ePCR application 122 can be stored in the memory of the mobile computing device 104 as an Android™ application, an Apple® application, or other native application, and executed by the processor to interact with the healthcare provider 118. Alternatively or additionally, the memory of the mobile computing device 104 may store a browser, or some other execution environment, configured to receive and render portions of the ePCR application 122 from one or more webserver(s).

In some examples, the ePCR application 122 can generate charting data to be stored in the charting data store 134. For instance, the ePCR application 122 can include a graphical user interface, which permits the user to select different subsets and/or display modes of the information gathered from and/or sent to other devices, according to examples of the present disclosure. In one example, the ePCR application 122 can be used to note a dosage of medicine, CPR compression depth, or other treatment parameters given to the patient at a particular time. The ePCR application 122 can also be used to record biographic and/or demographic and/or historical information about a patient, for example the patient's name, identification number, height, weight, and/or medical history, according to examples of the present disclosure. The types of charting data received via the ePCR application 122 can also include patient physiologic parameters, documented events, and the like. Charting data can include, but is not limited to, patient information (e.g., name, age, gender, weight, and/or other identification and/or demographic information), medical event specific information (e.g., type of service requested, disposition), and/or clinical information (e.g., patient assessment, patient blood pressure). Charting data can further include any data from the patient care record, data from physician's chart, data from electronic health records, data from one or more health information exchanges, data from hospital charts, in addition to data from ePCRs.

In some examples, each of the association generators 142A and 142B is configured to process requests to generate information that associates one or more of the medical devices 120 with a particular patient encounter. In some examples, each association generator 142A and 142B exposes and implements a software interface (e.g., an API) configured to receive the requests to generate association information. In these examples, the ePCR application 122 and the event log application 140 are each configured to generate requests to generate association and to communicate the requests to the locally hosted association generator 142A or 142B. The ePCR application 122 and the event log application 140 may be configured to, for example, generate requests in response to receiving input from the healthcare provider 118A. This input may indicate initiation of a patient encounter, termination of a patient encounter, or simply that a patient encounter is in process. Alternatively or additionally, in some examples, each association generator 142A and 142B implements a user interface configured to receive the requests to generate association information. This user interface can include controls configured to receive input specifying initiation of a patient encounter, that a patient encounter is in process, and/or that a patient encounter has been completed. Further, the user interface can include controls configured to receiving input to initiate acquisition of representations of identifiers of medical devices and/or to receive other elements of association information as discussed herein. In addition, the user interface can include controls configured to receive input to initiate storage and transmission of the association information to the server(s) 108.

With continued reference to FIG. 1, the mobile computing devices 104 can include a combination of devices, according to some examples. For instance, the mobile computing devices 104 can each include a processor coupled with memory configured to store data manipulated by the processor. Each of the mobile computing devices 104 may have a clock, which can be synchronized with an external time source such as a network resource or a satellite to prevent the healthcare provider 118A from having to manually enter a time of treatment or observation (or having to attempt to estimate the time of treatment for charting purposes long after the treatment was administered), according to examples of the present disclosure. Each of the mobile computing devices 104 can include one or more systems, medical device(s), and/or network interfaces configured to receive and/or send data from and/or to other devices like the medical devices 102. In some examples, each of the mobile computing devices 104 can utilize these system(s), medical device(s), and/or network interfaces to communicate with another device or system (e.g., the remote computing device 106, another mobile computing device 104, and/or the server(s) 108) that aggregates or otherwise receives data from other devices, such as the medical devices 102. Alternatively or additionally, each of the mobile computing devices 104 can communicate with devices, such as the medical devices 102, by establishing or joining a previous established local network including data entry devices as well as diagnostic and/or therapeutic medical devices. This local network can be established in an ad-hoc manner at the time of treatment of a patient or patients in the field and can include two or more proximally located devices.

In various implementations, each of the mobile computing devices 104 can receive, organize, store, share, distribute, and display data from the other devices (e.g., the medical devices 102 and other mobile computing device 104) to further enhance the usefulness of the devices and to make it easier for the healthcare provider 118A to perform certain tasks that would normally require the healthcare provider 118A to divert visual and manual attention to the other devices separately, according to examples of the present disclosure. In other words, each of the mobile computing devices 104 can centralize, organize, and share information that might otherwise be de-centralized and disorganized, according to examples of the present disclosure. However, it should be noted that robust, bi-directional, fully authenticated network connections can require substantial computing resources and time to establish and maintain. As a consequence, at least some examples avoid these sorts of network connections.

In certain examples, each of the mobile computing devices 104 can share information received from the server (s) 108 with the other devices. For instance, in one example, the mobile computing device 104A can receive information from the server(s) 108 and can share (e.g., transmit via a local network) such information with the medical device 102A. Alternatively or additionally, if the medical device 102N takes an ECG reading of the patient 116, or if the medical device 102N administers a treatment (such as medication, chest compression, ventilation, defibrillation shock, etc.), information descriptive of the ECG and/or the treatment may be shared, via mobile computing device 104B or directly, with other devices (e.g., the remote computing device 106, the mobile computing device 104A, and/or the server(s) 108) for storage in a patient record maintained therein. In another example, each of the mobile computing devices 104 can be configured to receive patient information, such as medical records, known medical conditions, and biographical information form the health records data store 110, and to share this information with one or more of the medical devices 102. This biographical information can be inserted into a patient record (e.g., an ePCR) being maintained and/or generated at the mobile computing device 104.

When a mobile computing device 104 receives updated information from the other devices to which it is communicably coupled, and/or via input from a healthcare provider (e.g., either of the healthcare providers 118A or 118B), the mobile computing device 104 can send the updated information to the server(s) 108. Hence, information from one or more device(s) (e.g. the medical devices 102) may be stored locally at the mobile computing device 104 (e.g., in the memory 421) and/or at the server(s) 108 (e.g., in the memory 521, in the event log data store 146, and/or in the charting data store 134). Data from the mobile computing device 104 (and, when present, data from the other devices that may be communicably coupled with the mobile computing device 104) can be received by the server(s) 108 and stored in the event log data store 146, the charting data store 134, and/or the case data store 132 via the event log API 144, the ePCR API 128, and/or the case API 126 as described further below. The remote computing device 106 can also access the stored information via these interfaces to add the stored information to the health records data store 110.

According to some examples of the present disclosure, each of the mobile computing devices 104 can communicably couple (e.g. automatically or manually or selectively) to one or more medical devices 102 that include a defibrillator, a patient monitor, an automated external defibrillator, a ventilator, an automated chest compression device, and/or a wearable defibrillator. In these examples, any mobile computing device 104 so coupled can receive and display patient monitoring information generated by the one or more medical devices. Such a mobile computing device 104 can also be configured to receive patient-identifying protected health information from the one or more medical devices, to permit the mobile computing device 104 to query (e.g., across the network 112) an external database (e.g., the health records data store 110) to retrieve additional information about the patient 116. This mobile computing device 104 can also be configured to connect with an implantable cardioverter-defibrillator ("ICD") in a similar fashion, according to examples of the present disclosure.

In certain examples, each of the mobile computing devices 104 can be a tablet, smartphone, wearable device, and/or other mobile computing device and/or a combination of mobile devices that can access event log and patient charting system capabilities described herein via a server or cloud interface, for example, an interface with the server(s) 108. According to some examples of the present disclosure, the mobile computing devices 104 can include wristbands and/or smart phones such as an Apple® iPhone® or iPad® with an interactive data entry interface such as a touchscreen or voice recognition data entry interface that can be communicably coupled to the tablet and tapped to indicate what was done with the patient 116 and when it was done. Further, according to some examples of the present disclosure, the mobile computing devices 104 can be integrated with the medical devices 102, such that a single device can be configured to monitor the patient, treat the patient, as well as to generate records and/or notes about the patient's condition and/or treatments applied to the patient 116. In these examples, the ePCR application 122 can be embedded within the combination medical/computing device. Additional description of some components of the mobile computing devices 104 is provided further detail below with reference to FIG. 18.

In various implementations, the medical devices 102 can include patient treatment devices, or other kinds of device that include patient monitoring and/or patient treatment capabilities, according to examples of the present disclosure. For example, a medical device 102 can include a defibrillator and can be configured to deliver therapeutic electric shocks to the patient. In some examples, a medical device 102 can deliver other types of treatments, such as ventilation, operating a respirator, performing CPR, and/or administering drugs or other medication.

More specifically, one or more of the medical devices 102 can be, for example, a defibrillator with patient interface devices 190 such as electrodes and/or sensors configured for attachment to the patient 116 to monitor heart rate and/or to generate electrocardiographs (ECGs), according to examples of the present disclosure. Each of the medical devices 102 can include a clock, which can be synchronized with an external time source such as a network resource or a satellite to prevent the healthcare provider 118A from having to manually enter a time of treatment or observation (or having to attempt to estimate the time of treatment), according to examples of the present disclosure. Precise clock synchronization between the medical devices 102 and the mobile computing devices 104 can be particularly helpful in associating medical device case files to particular patient encounters, especially where timestamps are used in at least one search criterion, as is described further below. As such, in at least some examples, each medical device 102 and mobile computing device 104 includes a timing circuit with a local clock. The timing circuits can each include a local clock, and the timing circuits can communicate with one another to determine and correct for variations between the local clocks of the timing circuits. In some examples, one of the timing circuits can act as a "master" timing circuit, and each of the other timing circuits can act as "slave" timing circuits that synchronize with the local clock at the master timing circuit. In some cases, these timing circuits can enable the medical devices 102 and the mobile computing devices 104 to achieve sub-microsecond level synchronization. In other cases, these timing circuits can enable the processing circuits to achieve synchronization within the range of 1-100 microseconds (e.g., 1-10 microseconds), or less. In at least one example, the medical devices 120 and the mobile computing devices 104 utilize a timing protocol to coordinate timing between master timing circuits and slave timing circuits. Examples of such timing protocols can include the IEEE 1588 or Precision Time Protocol (PTP), the Network Time Protocol (NTP), the Clock Sampling Mutual Network Synchronization (CS-MNS) algorithm, the Reference Broadcast Synchronization (RBS) algorithm, the Reference Broadcast Infrastructure Synchronization (RBIS) algorithm, and the Global Positioning System (GPS). The IEEE 1588-2008 Standard for Precision Clock Synchronization Protocol for Networked Measurement and Control Systems is incorporated by reference herein in its entirety. The IEEE 1588 protocol is also described in further detail in Jones, Mike, "Get in Sync!: IEEE 1588v2 Transparent Clock Benefits for Industrial Control Distributed Networks," Micrel, Inc. (Mar. 22, 2012), and from Wu, Jiang and Peloquin, Robert, "Synchronizing Device Clocks Using IEEE 1588 and Blackfin Embedded Processors," Analog Dialogue 43-11 (November 2009), both of which are incorporated by reference herein in their entirety.

Each of the medical devices 102 can also include and/or couple to patient interface devices 190 such as sensors to detect and/or a processor to derive or calculate other patient parameters. In some examples, one or more of the medical devices 102 are configured to interoperate with the patient interfaces devices 190 to monitor, detect, treat, and/or derive or calculate blood pressure, temperature, respiration rate, blood oxygen level, end-tidal carbon dioxide level, pulmonary function, blood glucose level, and/or weight, according to examples of the present disclosure. Additional examples of the medical devices 102 and the patient interface devices 190 are described further below with reference to FIG. 18.

In some examples, to initiate easy access to the medical device case files generated by the medical devices 102 through the generation of association information, the healthcare provider 118A can use a medical device interface present within the mobile computing device 104 to acquire representations of identifiers of the medical devices. This medical device interface can include, for example, a camera, a near-field communication sensor, a radio frequency identification sensor, a universal serial bus connector, an infrared sensor, a personal area network sensor, a proximity detector, a geolocation detector, a wireless network connector, or another sensor appropriate to gather the relevant identifying information. Notably, in certain examples, these medical device interfaces acquire the representations without establishing a time-consuming communication or authentication session with the medical devices. For instance, in some examples, the medical device interface includes a camera and simply scans a QR code, bar code, or device identifier visible on the medical devices. Additionally or alternatively, in some examples the medical device interface reads a NFC tag or radio frequency identification (RFID) tag affixed to the medical devices. Regardless of the specific technology used, this lightweight approach to acquiring representations of the identifiers minimizes the time of the healthcare provider 118A required to generate association information, and ultimately be able to access the integrated data source encounter structure of the patient encounter in an easy and intuitive manner. It should be noted that, in at least some examples, the identifiers of the medical devices uniquely identify each medical device.

With continued reference to FIG. 1, upon completion of a patient encounter (e.g., via conclusion of patient treatment and/or transfer of the patient 116 to a healthcare facility, such as an emergency room (ER) of a hospital) and/or during the patient encounter, the healthcare provider 118A may wish to provide an ER attending or other healthcare provider 118B within an emergency response center with an integrated data source encounter structure of the patient encounter, and/or may wish to have immediate access to the integrated data source encounter structure during the medical emergency. In some situations, the integrated data source encounter structure must be provided quickly (e.g., where the patient's condition is critical and/or during the event). Thus, in some examples, the mobile computing device 104B is configured (e.g., via execution of the event log application 140) to transmit the association information to the mobile computing device 104C via a quick, lightweight communication technique using, for example, a medical device interfaces of a mobile computing devices 104. For example, in one example, the event log application is configured to render a visual representation of a token via a user interface of the mobile computing device 104B. In this example, the mobile computing device 104C is configured to (e.g., via execution of the encounter review application 148) acquire the representation of the token and transmit a request for the integrated data source encounter structure of the patient encounter via one or more of the interfaces 126 and 128. The encounter review application 148 can include the token in the request to uniquely identify the patient encounter for which an integrated data source encounter structure is sought. Completing the description of this example, the encounter review application 148 is configured to receive the response and provide the healthcare provider 118B with the integrated data source encounter structure via a user interface. Or, as discussed further herein, the server(s) 108 may transmit the integrated data source encounter structure back to one or more of the mobile computing devices 104 located at the scene, for benefit of the healthcare providers during the event.

According to examples of the present disclosure, the server(s) 108 can receive event log data and/or patient charting data from a mobile computing device 104 and store the data (e.g., via operation of the event log API 144 and/or the ePCR API 128) in the event log data store 146 and/or the charting data store 134 along with an authenticated time-stamp and an identifier associating the information with a particular mobile computing device 104. In this way, data from multiple devices can be accessed by various users.

In some examples, the network 112 can include one or more communication networks through which the medical device 102, the mobile computing device 104, the remote computing device 106, and the server(s) 108 can send, receive, and/or exchange data. In various implementations, the network 112 can include a cellular communication network and/or a computer network. In some examples, the network 112 includes and supports wireless network and/or wired connections. For instance, in these examples, the network 112 may support one or more networking standards such as GSM, CMDA, USB, BLUETOOTH, CAN, ZigBee®, Wireless Ethernet, Ethernet, and TCP/IP, among others. The network 112 may include both private networks, such as local area networks, and public networks, such as the Internet. It should be noted that, in some examples, the network 112 may include one or more intermediate devices involved in the routing of packets from one endpoint to another. However, in other examples, the network 112 can involve only two endpoints that each have a network connection directly with the other.

The server(s) 108 can include one or more physical and/or virtual server computers configured to implement the case API 126, the ePCR API 128, the event log API 144, the patient encounter data source integration service 130, the case data store 132, the event log data store 146, the criteria data store 136, and the charting data store 134. As such, the server(s) 108 can include one or more application servers, web servers, and/or data base servers. The server(s) 108 can communicate with the remote computing device 106, the medical devices 102, and the mobile computing devices 104 via the network 112. The server(s) 108 can include enterprise servers configured to support an organization as a sole tenant and/or cloud servers configured to support multiple organizations as multiple tenants.

The server(s) 108 may be implemented in one or more clouds that may communicably couple to one another. For example, a single cloud including one or more servers may include the elements 126, 128, 130, 132, 134, 136, 144, and 146 of FIG. 1. Alternatively, elements 126 and 132 may be implemented in a first cloud, elements 130 and 136 may be implemented in a second cloud, elements 128 and 134 may be implemented in a third cloud, and elements 144 and 146 may be implemented in a fourth cloud. As a further alternative, the elements 130 and 136 may be implemented in a same cloud as elements 126 and 132, or may be implemented in a same cloud as elements 144 and 146, or may be implemented in a same cloud as elements 128 and 134. As yet another alternative, elements 126, 128, 132, 134, 144, and 146 may be implemented in a first cloud and elements 130 and 136 may be implemented in a second cloud.

The communication link 188*a* illustrated in FIG. 1 between the patient encounter data source integration service 130 and the medical device case data store 132 is an optional link. Likewise, the communication link 188*b* illustrated in FIG. 1 between the patient encounter data source integration service 130 and the event log data store 146 is also an optional link. Likewise, the communication link 188*c* illustrated in FIG. 1 between the patient encounter data source integration service 130 and the charting data store 134 is also an optional link. In an implementation, the patient encounter data source integration service 130 may not communicate directly with these data stores for security purposes. In certain implementations, the patient encounter data source integration service 130 is conversant in multiple data formats and is able to interact with components of the medical device 102 and the mobile computing device 104 via a public API which can serve as a gatekeeper to resources provided by such devices. For example, the medical device case data store 132, the charting data store 134, and the event log data store 146 may be owned by a first entity or separately owned by a first, second, and third entity. The patient encounter data source integration service 130 may be owned by a fourth entity. Thus, the API's (126, 128, and/or 144) may provide security between these various entities in regard to access to the data stores 132, 134, and 146.

For these and/or other reasons, in certain implementations it may be preferred that the patient encounter data source integration service 130 not communicate directly with the medical device case data store 132, the charting data store 134, and/or the event log data store 146, as indicated by the broken lines 188*a*, 188*b*, and 188*c* shown in FIG. 1. In such case, the patient encounter data source integration service 130 may send the case API 126 a request for information that is stored in the medical device case data store 132. Likewise, the patient encounter data source integration service 130 may send the event log API 144 a request for information that is stored in the event log data store 146. Likewise, the patient encounter data source integration service 130 may send the ePCR API 128 a request for information that is stored in the charting data store 134. Any of these requests may include appropriate security credentials. Based on the security credentials, the case API 126, the ePCR API 128, and/or the event log API 144 may either grant or deny the request for information. If the respective interface grants the request for information, then the interface will retrieve the requested information from the appropriate data store. The patient encounter data source integration service 130 may perform one or more data merge operations according to one or more criteria identified by the patient encounter data source integration service 130. When the patient encounter data source integration service 130 completes the one or more data merge operations, the patient encounter data source integration service 130 may return the merged file (for example, a file that includes medical device data merged into patient charting data) to the case API 126 for storage in the medical device case data store 132.

In some examples, the server(s) 108 can exchange data with remote devices such as the medical devices 102, the mobile computing devices 104, and the remote computing device 106 via the case API 126, the ePCR API 128, and/or the event log API 144. These interfaces are configured to receive, process, and respond to commands issued by processes implemented by the remote devices, such as the ePCR application 122, the event log application 140, and the encounter review application 148 described herein. The interfaces 126, 128, and 144 may be implemented using a variety of interoperability standards and architectural styles. For instance, in one example, the interfaces 126, 128, and 144 are web services interfaces implemented using a representational state transfer (REST) architectural style. In this example, the interfaces 126, 128, and 144 communicate with a client process using Hypertext Transfer Protocol (HTTP) along with JavaScript Object Notation and/or extensible markup language. In some examples, portions of the HTTP communications can be encrypted to increase security. Alternatively or additionally, in some examples, the interfaces 126, 128, and 144 are implemented as a .NET web interface that responses to HTTP posts to particular uniform resource locators with data descriptive of case data, event log data, and charting data. Alternatively or additionally, in some examples, the interfaces 126, 128, and 144 are implemented using simple file transfer protocol commands and/or a proprietary application protocol accessible via a transmission control protocol socket. Thus, the interfaces 126, 128, and 144 as described herein is not limited to a particular implementation.

In some examples, the interfaces 126, 128, and 144 include a plurality of endpoints to enable reliable system performance. For instance, in at least one example, each of the interfaces 126, 128, and 144 includes a one or more first endpoints to receive and process requests for data previously stored in the case data store 132, the charting data store 134, or the event log data store 146 and one or more second endpoints to receive and process requests to store new data within the case data store 132, the charting data store 134, and the event log data store 146. This configuration can ensure that requests for data already stored in the case data store 132, the charting data store 134, and the event log data store 146 can be quickly serviced with minimal latency. This bifurcated architecture can be helpful because requests to upload ePCRs, case files, or event logs; parse the ePCRs, case files, or event logs; and store the resulting charting data, case data, or event log data in the case data store 132, the charting data store 134, or the event log data store 146 can require more processing time and resources.

In some examples, the interfaces 126, 128, and 144 are configured to transmit messages to the patient encounter data source integration service 130 that notify the patient encounter data source integration service 130 of (and/or include) newly received case data, charting data, event log data, and association information. Where the messages merely notify the patient encounter data source integration service 130 of the presence of new data, the messages can include one or more identifiers of the new data that can be utilized by the patient encounter data source integration service 130 to retrieve the new data from the case data store 132, the charting data store 134, and/or the event log data store, although the inclusion of identifiers of the new data is not a requirement. In certain examples, the case API 126 is configured to receive case files from the medical devices 102, process the case files, and transmit messages to the medical devices 102 that indicates the result of the processing. This processing can include parsing the case files to retrieve values of case data stored therein and storing the case data in the case data store 132. Similarly, in some examples, the ePCR API 128 is configured to receive ePCRs from the mobile computing devices 104, process the ePCRs, and transmit messages to the mobile computing devices 104 that indicates the result of the processing. This processing can include parsing the ePCRs to retrieve values of charting data stored therein and storing the charting data and/or the ePCRs in the charting data store 134. Likewise, in some examples, the event log API 144 is configured to receive event logs from the mobile computing devices 104, process the event logs, and transmit messages to the mobile computing devices 104 that indicates the result of the processing. This processing can include parsing the event logs to retrieve values of event log data stored therein and storing the event log data and/or the event logs in the event log data store 146. It should be noted that the ePCRs and/or the event logs can include association information, which can be referenced by the patient encounter data source integration service 130 to create consolidated case data.

In some examples, the interfaces 126 and 128 are further configured to receive requests from the encounter review application 148 for consolidated case data. The request can include a token that uniquely identifies the patient encounter for which consolidated data is requested. In response to receiving these requests, the interfaces 126 and 128 are configured to interoperate with the patient encounter data source integration service 130 to prepare and/or identify consolidated case data using the processes described herein and to return the consolidated case data to the encounter review application 148. Where the patient encounter data source integration service has prepared consolidated case data in advance (e.g., in response to receiving association information some time in advance of receiving the request from the encounter review application 148), the patient encounter data source integration service 130 can use the token to simply fetch the consolidated data from its storage and transmit the consolidated data to the encounter review application 148.

Continuing with FIG. 1, the charting data store 134 can be implemented by, for example, a database (e.g., a relational database) and stored on a non-transitory storage medium. In an implementation, the charting data store 134 includes a plurality of records that store charting data derived from a plurality of ePCRs. In at least one example, the charting data store 134 is organized into a set of relational database tables that includes an ePCR table and an ePCR fields table. In this example, the ePCR table includes rows of data that are each descriptive of an ePCR that documents a patient encounter in the charting data store 134. Thus, each row in the ePCR table can include fields configured to store a unique identifier of the ePCR, a timestamp indicating when the ePCR was created, and metadata descriptive of the patient encounter documented by the ePCR (e.g., patient identification information that uniquely identifies the patient, healthcare providers involved in the patient encounter, reasons the ePCR was closed ended and outcome, unique identifiers of medical devices and supplies used in the resolving the patient encounter, overall issues that occurred during the patient encounter, and/or a type of dispatched EMS event associated with the ePCR).

Continuing with this example, the ePCR fields table includes rows of data that are each descriptive of a field stored within an ePCR. Thus, each row in the ePCR fields table includes fields configured to store a unique identifier of the ePCR to which the field belongs, a field that uniquely identifies the field among the fields associated with the ePCR, a date/time stamp indicating when the field was populated with a value, a unique identifier of the source of the value (e.g., a particular medical device or a particular computing device), and a field that identifies (via a type identifier or textual information) one or more values associated with the field. Notably, each ePCR can have a large quantity of fields that each require entry of a specific data type. For instance, some example ePCRs may have as 100 fields, 200, fields, 400 fields, 600 fields, or more. This quantity of fields may be mandated and, therefore, it is important that each ePCR be complete. Therefore, in some examples the charting data store 134 and/or other components, such as the ePCR application 122, are configured to prevent modification/deletion of ePCR fields by a user of the ePCR application. It should be noted that, in some examples, ePCRs can be serialized into files for transmission to the charting data store 134. In these examples, the charting data store 134 can store complete and distinct copies of the ePCR files themselves (e.g., as large binary objects).

Continuing with FIG. 1, the case data store 132 can be implemented by, for example, a database (e.g., a relational database) and stored on a non-transitory storage medium. In an implementation, the case data store 132 includes a plurality of records that store case data derived from case files from a plurality of medical devices used to treat patients during encounters. Moreover, in some examples, the case data store 132 can store complete copies of the case files themselves (e.g., as large binary objects). The case data stored in the case data store 132 can document patient encounters from the point of view of medical devices. As such, case data generated by a medical device during a patient encounter can include an identifier of the medical device, physiologic parameter values of the patient recorded by the medical device during the encounter, characteristics of treatment provided by the medical device to a patient during the encounter, actions taken by healthcare providers during the encounter, and timestamps documenting when any of this information was recorded. For instance, where the medical device is a defibrillator, the case data can include patient physiologic parameters such as ECG data for the patient, as well as characteristics of therapeutic shocks delivered by the defibrillator to the patient, CPR (e.g., chest compressions and/or ventilations) performance data, and timestamps reflecting when the defibrillator was powered up and when this information was recorded, among other information.

The event log data store 146 can be implemented by, for example, a database (e.g., a relational database) and stored on a non-transitory storage medium. In one example, the event log data store includes a plurality of records that each specify a timestamped event. The event log data store 146 is configured to store a wide variety of events. Examples of these events include CPR administration, delivery of therapeutic electric pulses, provision of medication, occurrence of particular ECG rhythms, return of spontaneous circulation (ROSC), patient vitals information, procedures administered to the patient (e.g., placement of an intubation tube), medical device power on, entry of protected health information (e.g., information identifying a patient), provision of medical device prompts to the healthcare provider, provision of treatment (e.g., chest compressions sensed via acceleration signals generated from a sensor located on the sternum of the patient, ventilations sensed via flow/pressure signals generated from a sensor located along the patient airway), occurrence of particular ECG rhythms (e.g., ventricular fibrillation, ventricular tachycardia, asystole, pulseless electrical activity, sinus rhythm, etc.), delivery of a therapeutic electric pulse to the patient, and administration of medication, among other events.

The criteria data store 136 can be implemented by, for example, a database (e.g., a relational database) and stored on a non-transitory storage medium. In one example, the criteria data store 136 includes a plurality of records that each specify a relationship between elements of association information and parameters of case data, event log data, and/or charting data. In this example, each of the plurality of records also includes information that ranks the relationship relative to other relationships within the criteria data store 136. This ranking can be accessed by the patient encounter data source integration service during an iterative searching processes, as described further below with reference to FIGS. 15 and 16.

Criteria data store 136 optionally maintains an audit trail that tracks which data in an integrated record originated from an ePCR charting data file, and which data in the integrated record originated from a medical device case file. In certain embodiments where conflicting data exists, the most recently acquired data can take precedence over older data. In other embodiments where conflicting data exists, the configuration information can be used to specify a hierarchy of data sources that determine which data takes precedence (for example, retained) and which data is relegated (for example, discarded).

In one implementation an audit trail includes reference numbers for each file processed by the patient encounter data source integration service 130 along with an indication of the result of processing each file. For example, a medical device case file could be indicated as (i) having been merged with another medical device case file, or (ii) merged with an ePCR charting data file. Where multiple original medical device case files are merged and the resulting merged file is subsequently processed by the patient encounter data source integration service 130, the information in the audit file identifying the original files can be used to allow the patient encounter data source integration service 130 to (i) ignore the merged file if the original files have already been processed; (ii) select only a portion of the merged file for integration with an ePCR charting data file (for example, if the remainder of the merged file has already been integrated; or (iii) integrate the merged file with an ePCR charting data file with redundancy information that the ePCR API 128 can use to remove redundant information.

The case data store 132, the charting data store 134, and the event log data store 146 can be organized according to a variety of physical and/or logical structures. In at least one example, the case data store 132, the charting data store 134, and the event log data store 146 are implemented within a relational database having a highly normalized schema and accessible via a structured query language (SQL) engine, such as ORACLE or SQL-SERVER. This schema can, in some implementations, include columns and data that enable the case data store 132, the charting data store 134, and/or the event log data store 146 to house data for multiple tenants. In addition, although the description provided above illustrates the case data store 132, the charting data store 134, and the event log data store 146 as relational databases, the examples described herein are not limited to that particular physical form. Other databases may include flat files maintained by an operating system and including serialized, proprietary data structures, hierarchical database, xml files, NoSQL databases, document-oriented databases and the like. Thus, the case data store 132 and the charting data store 134 as described herein is not limited to a particular implementation.

The case data store 132, the charting data store 134, and the event log data store 146 can securely store the information received from the mobile computing devices 104 and/or the medical devices 102 for longer periods of time than the remote devices to permit later use of the information. For example, the mobile computing devices 104 may receive protected health information (e.g., patient-identifying information such as name, address, and/or social security number) via user input directly into the mobile computing devices 104, and then may convey some or all of the protected health information to the server(s) 108 to query the charting data store 134 or the event log data store 146 for past records involving the patient 116. In an implementation, the mobile computing devices 104 can convey some or all of the patient-identifying information to other servers via the network 112 to access patient records and/or information from various databases such as those provided by a medical facility, insurance company, medical billing service, financial record service, and/or a health information exchange. In other examples, the mobile computing devices 104 can be configured to receive information in other ways, including without limitation wired or wireless communication and/or messaging.

The server(s) 108 and/or other servers accessed via the network 112 can then forward any such records or portions of such records back to the mobile computing devices 104 (e.g. for display in an event log screen, a patient charting screen, or past medical history screen) to assist the healthcare provider 118A with the current emergency encounter. Similarly, such past encounter information may also be accessed by other users such as or the healthcare provider 118B, according to examples of the present disclosure.

The remote computing device 106 can include one or more physical and/or virtual computers configured to implement the health records data store 110. The health records data store 110 can include records descriptive of patient medical history. These records can include a variety of patient information, such as medical history prior to an encounter, symptoms that lead to an encounter, any diagnosis identified during the encounter, treatments prescribed as a result of the encounter, and outcomes resulting from the treatments. In at least one example, the remote computing device 106 and the health records data store 110 collectively act as a health information exchange (HIE) that is configured to expose one or more interfaces that support health data exchange standards, such as state-wide health data exchange standards, regional health data exchange standard, HL7 message standards, and National Council for Prescription Drug Programs (NCPDP) script standards. It should be noted that the health records data store 110 can include data generated by one organization or by other organizations or networks or third-party sources, such as hospitals, clinics, doctors' offices, and pharmacies.

Associating Processes

Figure 4:
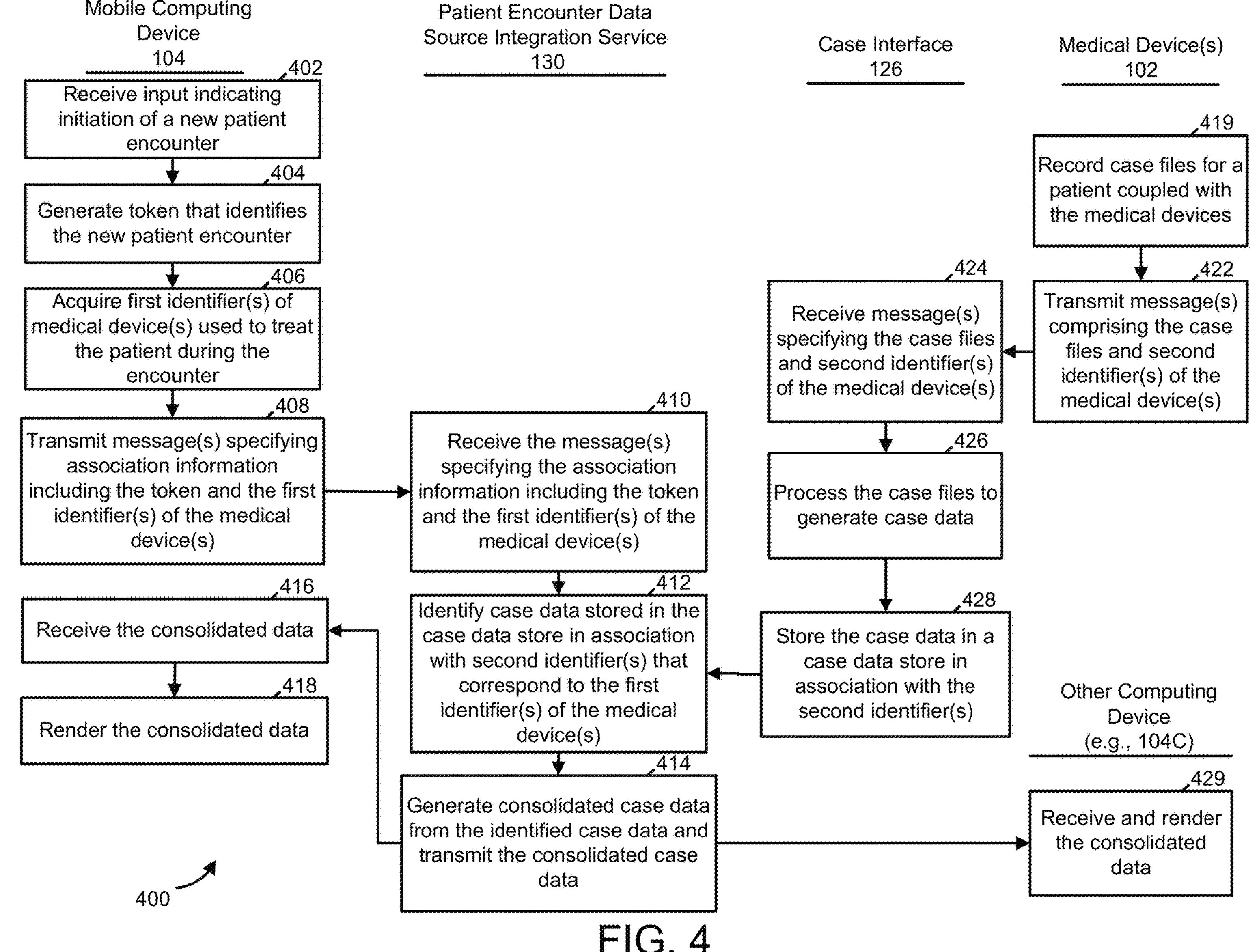
FIG. 4 is a flow diagram illustrating a case file consolidation process in accordance with at least one example disclosed herein.

In some examples, the system 100 is configured to execute a variety of processes that consolidate case data from a plurality of medical device case files. FIG. 4, for instance, illustrates a consolidation process 400 that is executed by a mobile computing device (e.g., a mobile computing device 104 of FIG. 1), a patient encounter data source integration service (e.g., the patient encounter data source integration service 130 of FIG. 1), a case interface (e.g., the case API 126 of FIG. 1), and one or more medical devices (e.g., the medical devices 102 of FIG. 1).

The consolidation process 400 starts with the mobile computing device receiving 402 input indicating initiation of a new patient encounter. For example, the mobile computing device may receive input requesting generation of association information such as for associating data generated by different medical devices involved in the patient encounter, input requesting creation of a new ePCR, or input request creation of a new event log. In response to reception of the input, the mobile computing device generates 404 (e.g., via execution of an association generator 142A or 142B of FIG. 1) a token to represent the new patient encounter. For instance, the association generator 142 can generate a UUID and store the UUID as the token in local memory. At some point during the patient encounter, the mobile computing device acquires 406 one or more representations of one or more first identifiers of one or more medical devices used to treat a patient (e.g., the patient 116 of FIG. 1) during the patient encounter. For instance, the mobile computing device can acquire an image of a QR code or identifying tag (e.g., via NFC) that identifies a medical device. Next, the mobile computing device transmits 408 one or more messages specifying association information including the token and the one or more first identifiers to the patient encounter data source integration service (e.g., via an ePCR interface or event log interface, such as the ePCR API 128 or the event log API 144 of FIG. 1).

As another part of the consolidation process 400, the medical devices record 419 case files for the patient during the patient encounter. For instance, the medical devices may acquire patient time-stamped physiological data, patient demographic data, and/or healthcare provider performance data and store this case data in association with one or more second identifiers of the medical devices in local memory. The medical devices transmit 422 messages comprising the case files and the one or more second identifiers of the medical devices to the case interface. The case interface receives 424 the messages comprising the case files and the one or more second identifiers and processes 426 (e.g., parses) the case files to generate case data. Next, the case interface stores 428 the case data in association with the second identifiers within a case data store (e.g., the case data store 132 of FIG. 1) for subsequent processing by the patient encounter data source integration service.

Continuing the consolidation process 400, the patient encounter data source integration service receives 410 the message specifying the association information. The patient encounter data source integration service identifies 412 (e.g., via execution of one or more associating processes, such as those described in detail below with reference to FIGS. 6, 7, and 12-16) case data stored in the case data store in association with second identifiers that correspond to the first identifiers of the medical devices. It should be noted that, although corresponding medical device identifiers are helpful in identifying case files for the patient encounter, corresponding medical device identifiers alone may be insufficient to positively identify only case files involved in the patient encounter. As such, some examples utilize additional criterion, such as timestamps and/or geotags, as discussed further below. The patient encounter data source integration service generates 414 consolidated case data from the identified case data and transmits 414 the consolidated case data to the mobile computing device (e.g., via one or both of the ePCR interface and the event log interface). This consolidated case data can comprise identified case data, charting data, and/or event log data, all associated with the same patient encounter.

Continuing the consolidation/integration process 400, the mobile computing device receives 416 the consolidated data and renders 418 the consolidated data, for example via execution of a local application (e.g., the ePCR application 122, the event log application 140, and/or the encounter review application 148). In some examples, because the mobile computing device is the source of the association information for the case files generated by the multiple medical devices linked to the patient encounter, the same mobile computing device may receive the consolidated data, by request or automatically, without requiring the healthcare provider to separately access other devices which could otherwise be an inconvenient exercise that could involve authentication or other inconvenient measures.

It should be noted that in some examples the consolidated case data may also be transmitted 414 to computing device other than the mobile computing device 104A (e.g., the mobile computing device 104C or another computing device) to be rendered 429 on a user interface display, such as at a medical case review station, remote telemedicine device, or the like. For instance, the consolidated case data may be made available for a clinician who is located remote from the scene, so that he/she can provide guidance or instruction for the healthcare providers who are immediately located onsite. Alternatively, or in addition, the consolidated case data may be accessed by a user after the medical event has ended, for post-case analysis and review.

It should also be noted that in some examples of the consolidation process 400, within the operation 422 the medical devices stream case files in real-time to the case interface. In these examples, the case interface and the patient encounter data source integration service also operate in real-time to identify case data being streamed as part of a live patient encounter, consolidate the streamed case data, and transmit the consolidated case data to the mobile computing device for real-time rendering. Accordingly, the consolidated case data may be updated in a real-time manner so that medical practitioners are able to receive live information generated by various devices located at the scene, so as to be able to achieve a high-level perspective of all notable occurrences during the patient encounter.

Figure 5A:
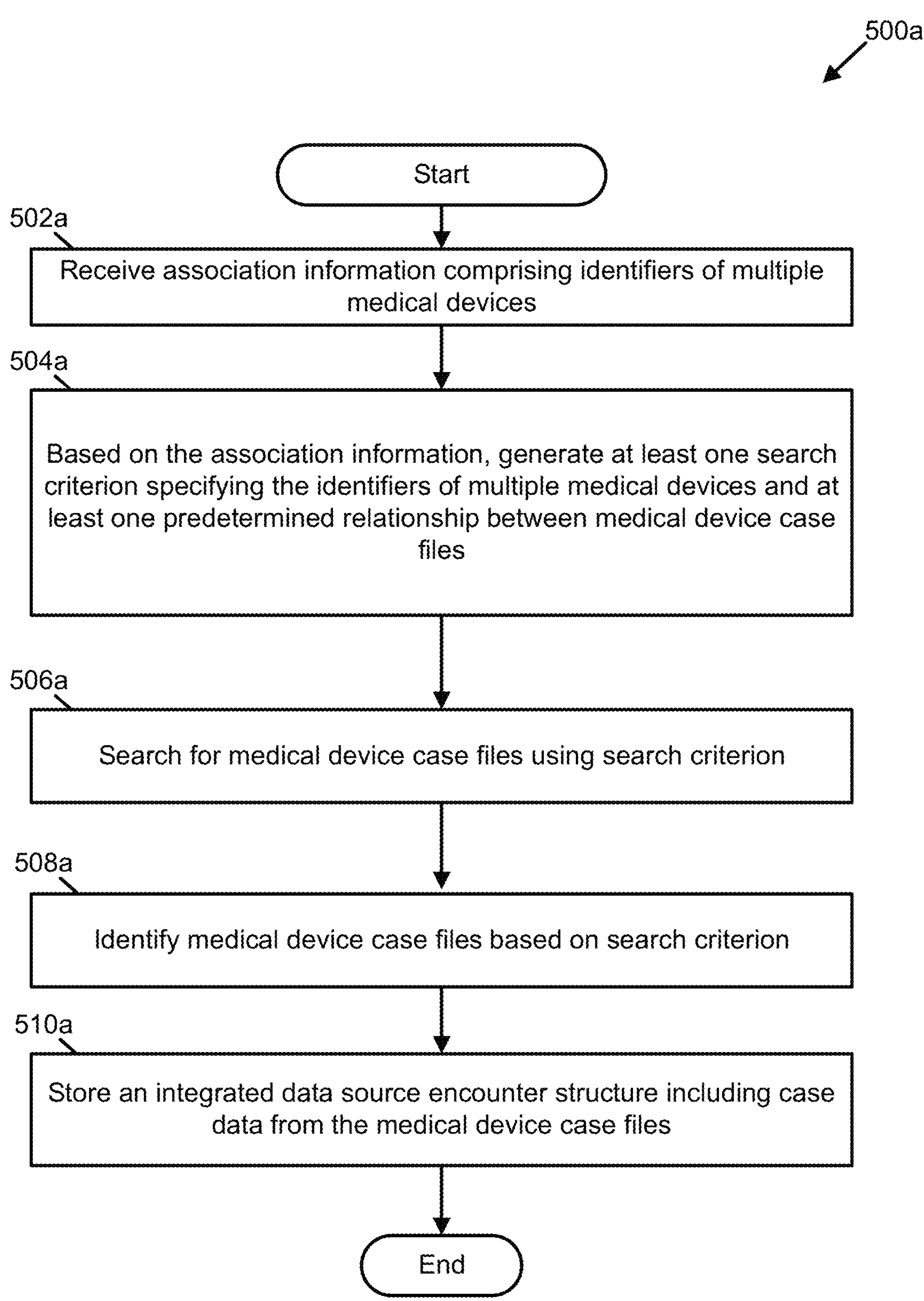
FIG. 5A is a flow diagram of a case file consolidation process executed by a patient encounter data source integration service in accordance with at least one example disclosed herein.

In some examples, the patient encounter data source integration service 130 is configured to identify a plurality of case files (e.g., generated by medical devices located at the scene) to associate with one another and, in some implementations, to associate with ePCRs and/or event logs that document a patient encounter. As discussed above, medical data from the case files, ePCRs, and event logs can be stored respectively within the case data store 132, the charting data store 134, and the event log data store 146, along with copies of the case files, ePCRs, and event logs. In some implementations, associations between case files, ePCRs, and event logs can be stored within the data stores 132, 134, and 146 as well. FIG. 5A illustrates one example of a consolidation process 500*a* executed by the patient encounter data source integration service 130 in these, and other, implementations.

As shown in FIG. 5A, the process 500*a* starts with the patient encounter data source integration service receiving 502*a* association information from the mobile computing device 104 located at the scene which has acquired identifying information from the medical device(s) and subsequently generated the association information to provide the link for the data originating from the medical device(s). In some examples, the healthcare provider using the mobile computing device for associating the medical device data may provide input on the mobile device to generate the association information between medical devices, and to send a request to the server(s) for associating of the relevant corresponding case files together. The patient encounter data source integration service can receive 502*a* a message generated from an interface (e.g., case API 126, ePCR API 128 and/or event log API 144 of FIG. 1) including the association information. Alternatively or additionally, in some examples, the patient encounter data source integration service can receive 502 the association information from a data store (e.g., the charting data store 134 and/or the event log data store 146 of FIG. 1). In these examples, the patient encounter data source integration service can utilize identifiers of charting data or event log data included in a message from the interface to request and receive 502*a* the association information as contained within the charting data or the event log data. Alternatively or additionally, in these examples, the patient encounter data source integration service can request and receive 502*a* charting data added to the charting data store or event log data added to the event log data store after a predefined timestamp maintained by the patient encounter data source integration service to mark the last time new charting data or event log data was requested.

Continuing the process 500*a*, the patient encounter data source integration service generates 504*a* at least one search criterion based on the association information. In some examples, the at least one search criterion specifies the identifiers of the plurality of medical devices included in the association information and at least one predetermined relationship between at least one element of the association information and at least one parameter associated with a medical device case file. The predetermined relationship can vary between examples. For instance, in some examples, the predetermined relationship can be an equality between the at least one element and the at least one parameter. A predetermined relationship of equality can be particularly useful where the at least one element and the at least one parameter include numeric values or strings that can be matched or satisfied with precision. Alternatively or additionally, the predetermined relationship can be a proximity or similarity between the at least one element and the at least one parameter. A predetermined relationship based on proximity or similarity can be particularly useful where the at least one element and the at least one parameter include timestamps, physiological measurements taken at different times or by different devices, or other values that can only be matched or satisfied inexactly (e.g., by satisfying a threshold proximity or similarity). Alternatively or additionally, the predetermined relationship can be a combination of equality, proximity, and/or similarity between multiple elements and parameters. For instance, in one example, the predetermined relationship requires at least one of an overlapping range between a case start time and a case end time as recorded in a case file and the association information and an equality between a patient biometric identifier from the case file and the association information and an equality between a healthcare provider biometric identifier from the case file and the association information. In some implementations the overlapping range between the case start times and end times recorded in a case file and the association information begins at the case start time included in the association information and ends at the case end time included in the association information. In other implementations the target time range begins slightly before or slightly after the case start time included in the association information and ends slightly before or slightly after the case end time included in the association information. Thus, the target time range may be defined by target range start and end times that are within a threshold proximity of respective case start and end times included in the association information. For example, if the association information indicates a case start time of 10:00 am and a case end time of 10:15 am, the target time range may be 9:55 am to 10:20 am, 9:55 am to 10:16 am, 9:59 am to 10:20 am, 10:01 am to 10:15 am, 10:00 am to 10:14 am, or any other suitable range. Thus, it will be appreciated that the difference between the target range start time and the association information case start time is not necessarily the same as the difference between the target range end time and the association information case end time. In general, clocks between different medical devices may not be exactly synced with one another. In some embodiments, the case start times/end times exactly match between the medical device case file and the association information.

In some examples, the at least one predetermined relationship is a hardcoded part of the patient encounter data source integration service. In these examples, the patient encounter data source integration service generates 504*a* the at least one search criterion by identifying the at least one element within the association information and associating the at least one element with the predetermined relationship.

For example, where the predetermined relationship is proximal and requires a parameter of a case file be within a range of an element of the association information and the element is a timestamp indicating when a case documenting an encounter was started, the patient encounter data source integration service generates 504*a* the at least one search criterion by identifying the timestamp within the association information and associating the timestamp with the range of case start times for subsequent use in searching 506*a*. It should be noted that such a range can be a dynamic value calculated by the patient encounter data source integration service and/or a predetermined value. For instance, a range can include a calculated range between a case start time and a transfer-of-care time from the association information. Alternatively or additionally, a predetermined range of case start times can be, for example, between 0-1, 0-2, 0-5, and 1-10 minutes. Any given predetermined relationship can apply these ranges between elements and time parameters indicating the same event (e.g., case start times) or between elements and time parameters indicating different events (e.g., a case start time and a treatment time or a transfer time).

In some examples, the at least one predetermined relationship is softcoded and stored within a criteria data store (e.g., the criteria data store 136 of FIG. 1). In these examples, the patient encounter data source integration service can generate 504*a* the at least one search criterion by identifying a preferred predetermined relationship from the criteria data store prior to identifying, within the association information as described above, the at least one element specified by the predetermine relationship. For instance, in some examples, the patient encounter data source integration service can identify the preferred predetermined relationship by finding the predetermined relationship with the highest rank that has not yet been used by the current instance of the process 500*a*.

It should be noted that each of the at least one element and the at least one parameter can be a single element or parameter or a plurality of elements or parameters. For instance, in some examples, the at least one element is a timestamp indicating a time when an ePCR or event log was opened and the at least one parameter is a timestamp indicating a time when a case file was started. In other examples, the at least one element includes a plurality of elements and the at least one parameter includes a plurality of parameters. In some of these examples, the plurality of elements includes a timestamp indicating a time when an ePCR or event log was uploaded to the server(s) 108 and an identifier of a mobile computing device that generated the ePCR or event log and the plurality of parameters includes a timestamp indicating a time when the case file was uploaded to the server(s) 108 and an identifier of a medical device that generated the case file. Other elements of association information can include patient identifiers, healthcare provider identifiers, medical device identifiers, timestamps indicative of patient transfer, patient treatment information, patient medical information, patient demographic information, and physiological measurements specified in the charting data. Other parameters associated with case files can include patient identifiers, healthcare provider identifiers, medical device identifiers, timestamps indicative of patient transfer, patient treatment information, patient medical information, patient demographic information, and physiological measurements taken by a medical device specified in the case file. The patient identifiers can include biometric information (e.g., facial recognition information, fingerprint information, retinal scan information, and the like). The medical device identifiers can include identifiers manually entered into an ePCR, identifiers retrieved from memory of the medical device, identifiers electronically transmitted by the medical device to the mobile computing device, and/or identifiers scanned from a bar or quick response code associated with the medical device. The physiological measurements can include blood pressure, body temperature, respiratory rate, heart rate, and electrocardiogram (ECG) data, among other physiological data.

Continuing the process 500*a*, the patient encounter data source integration service searches 506*a* the case data for a case file that matches or satisfies the at least one search criterion. During this searching 506*a*, the patient encounter data source integration service can identify 508*a* a case file to associate with the association information based on the at least one search criterion. For instance, the patient encounter data source integration service can identify 508*a* a case file as a corresponding case file where a parameter associated with the case file, stored in the case data, satisfies the predetermined relationship with an element of the association information stored in the at least one search criterion.

Where the patient encounter data source integration service identifies 508*a* an association of corresponding case data, the patient encounter data source integration service stores 510*a* an integrated data source encounter structure including case data (which may be streaming real-time) from the plurality of medical device case files for subsequent processing, and the process 500*a* ends. The integrated data source encounter structure can include, for example, a copy of or a pointer to the one or more of the plurality of medical device case files, case data generated from the plurality of medical device case files, and/or charting data and/or event log data containing or associated with the association information. As described above, association information can be associated with charting data and/or event log data via an identifier of a mobile device used to create both the association information and the charting data and/or the event log data. Further, in some examples, the integrated data source encounter structure can include a supplemented ePCR or event log that includes case data imported from and the associated plurality of medical device case files. The integrated data source encounter structure can be stored, for example, in the charting data store, the event log data store, and/or the case data store.

Figure 5B:
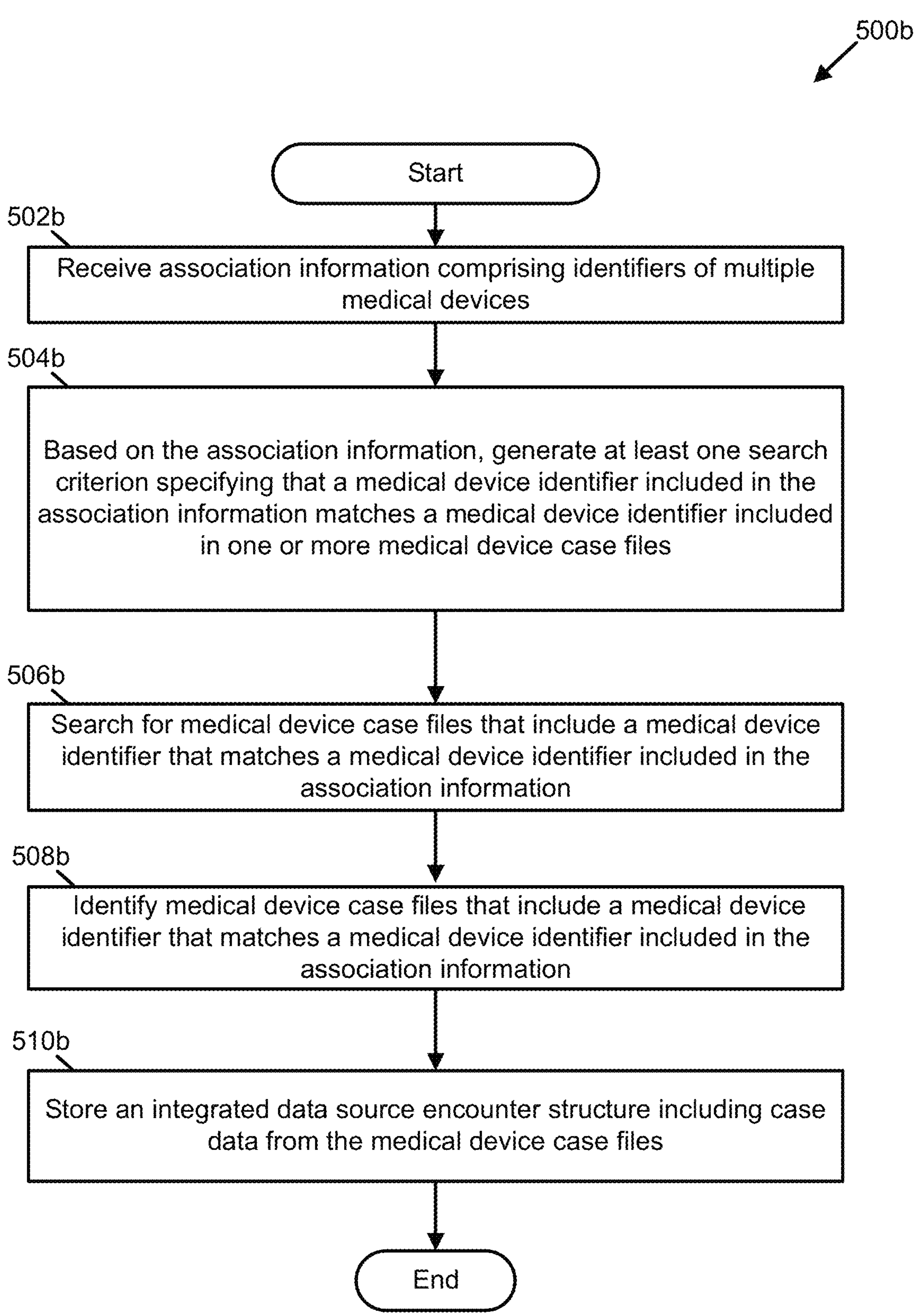
FIG. 5B is a flow diagram of a case file consolidation process executed by a patient encounter data source integration service in accordance with an example implementation that identifies a medical device case file that includes medical device identifiers that match medical device identifiers included in association information.

FIG. 5B illustrates an example of an integration process 500*b* that is executed by the patient encounter data source integration service 130 and that identifies one or more medical device case files that include a medical device identifier that matches (e.g., exactly or closely matching) a medical device identifier included in the association information.

As shown in FIG. 5B, the process 500*b* starts with the patient encounter data source integration service 130 receiving 502*b* association information uploaded by the mobile computing device 104. The patient encounter data source integration service 130 can receive 502*b* within the process 500*b* by executing actions such as those executed by the patient encounter data source integration service 130 to receive 502*a* within the process 500*a* described above with reference to FIG. 5A.

The patient encounter data source integration service 130 generates 504*b* at least one search criterion that specifies that a medical device identifier included in the association information matches (e.g., exactly or closely matching) a medical device identifier included in one or more medical device case files. The medical device identifier may include information from, for example, an RFID tag, a barcode, or a QR code. The medical device identifiers can include identifiers manually entered into an ePCR, identifiers retrieved from memory of the medical devices, identifiers electronically transmitted by the medical devices to the charting device, and/or identifiers scanned from a bar or QR code associated with the medical devices.

Continuing the process 500*b*, the patient encounter data source integration service 130 searches 506*b* for case files that satisfy the at least one search criterion. In particular, the patient encounter data source integration service 130 searches for medical device case files that include a medical device identifier that matches (e.g., exactly or closely matching) a medical device identifier included in the association information. Where the patient encounter data source integration service 130 identifies 508*b* one or more case files that include the medical device identifier based on the at least one search criterion, the patient encounter data source integration service 130 stores 510*b* an integrated data source encounter structure including case data and the process 500*b* ends. The patient encounter data source integration service 130 can store 510*b* within the process 500*b* by executing actions such as those executed by the patient encounter data source integration service 130 to store 510*a* within the process 500*a* described above with reference to FIG. 5A.

Another example of an integration process that is executed by the patient encounter data source integration service 130 identifies a medical device case file that includes a case start time and/or case end time that matches (e.g., exactly or closely matching) a case start time and/or case end time included in the association information. As used herein, matching a case start time and/or end time from a medical device case file with a case start time and/or end time included in the association information can include times that are within a target time range. In some implementations the target time range begins at the case start time included in the association information and ends at the case end time included in the association information. In other implementations the target time range begins slightly before or slightly after the case start time included in the association information and ends slightly before or slightly after the case end time included in the association information. Thus, the target time range may be defined by target range start and end times that are within a threshold proximity of respective case start and end times included in the association information. For example, if the association information indicates a case start time of 10:00 am and a case end time of 10:15 am, the target time range may be 9:55 am to 10:20 am, 9:55 am to 10:16 am, 9:59 am to 10:20 am, 10:01 am to 10:15 am, 10:00 am to 10:14 am, or any other suitable range. Thus, it will be appreciated that the difference between the target range start time and the association information case start time is not necessarily the same as the difference between the target range end time and the association information case end time. In general, clocks between different medical devices may not be exactly synced with one another. In some embodiments, the case start times/end times exactly match between the medical device case file and the association information. In an example process, the patient encounter data source integration service 130 generates at least one search criterion that specifies that a case start time and/or case end time included in the charting data matches (e.g., exactly or closely matching) a case start time and/or case end time included in the medical device case file. For example, in one implementation a case start time included in the association information matches a case start time included in a given medical device case file. In another implementation, a case end time included in the association information matches a case end time included in a given medical device case file. In another implementation, (a) a case start time included in the association information matches a case start time included in a given medical device case file and (b) a case end time included in the association information matches a case end time included in a given medical device case file. The patient encounter data source integration service 130 then searches the case data for one or more case files that satisfy the at least one search criterion. In particular, the patient encounter data source integration service 130 searches for one or more medical device case files that include a case start time and/or case end time that matches a case start time and/or case end time included in the association information. Where the patient encounter data source integration service 130 identifies one or more case files to associate with the association information based on the at least one search criterion, the patient encounter data source integration service 130 stores an integrated data source encounter structure, for example by executing actions such as those executed by the patient encounter data source integration service 130 to store 510*a* within the process 500*a* described above with reference to FIG. 5A.

Figure 5C:
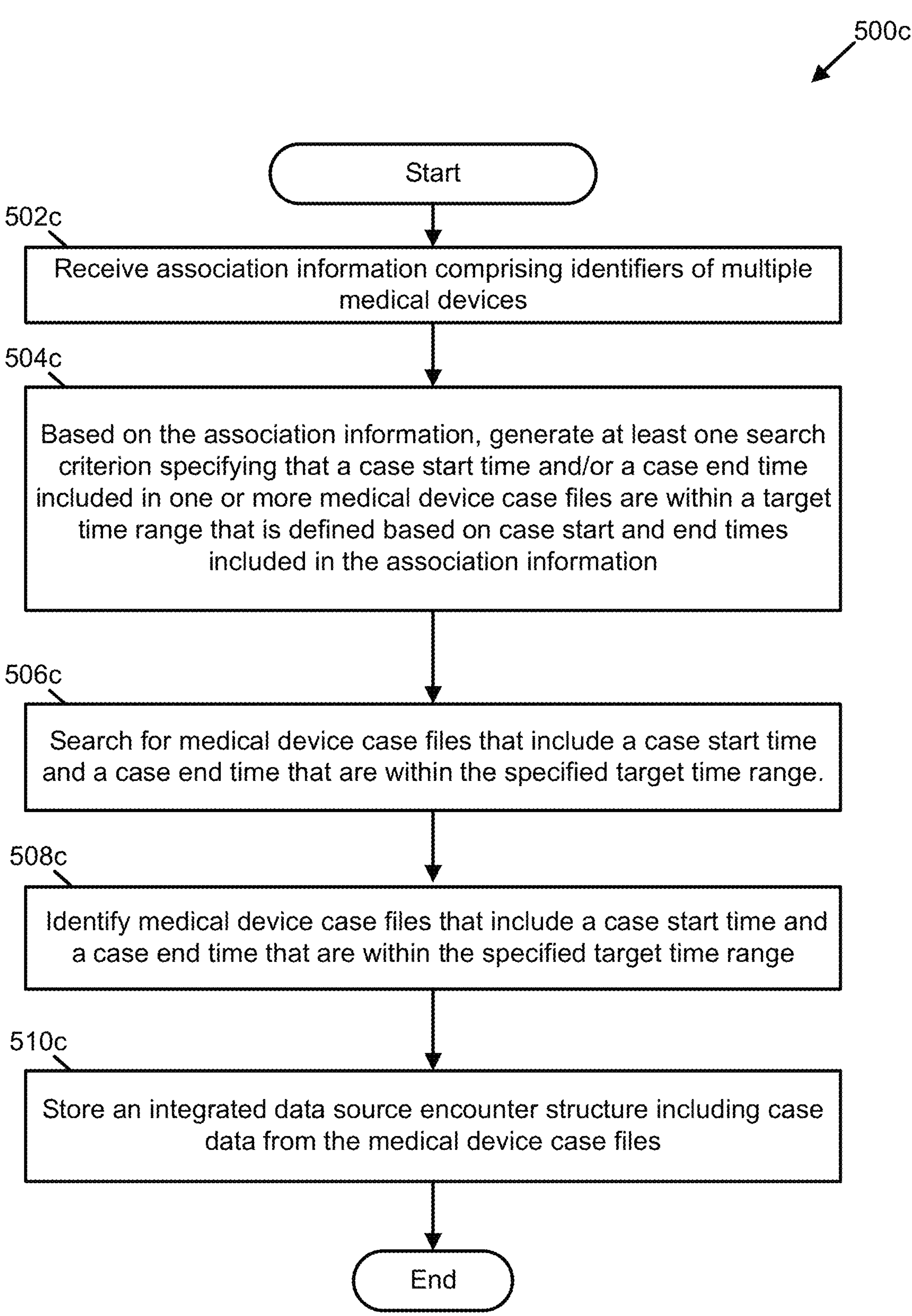
FIG. 5C is a flow diagram of a case file consolidation process executed by a patient encounter data source integration service in accordance with an example implementation that identifies medical device case files that include a case start time and a case end time that are within a target time range that is defined based on case start and end times included in association information.

FIG. 5C illustrates an example of an integration process 500*c* that is executed by the patient encounter data source integration service 130 and that identifies one or more medical device case files that include a case start time and/or a case end time that are within a "target time range" that is defined based on case start and end times included in the association information. In some implementations the target time range begins at the case start time included in the association information and ends at the case end time included in the association information. In other implementations the target time range begins slightly before or slightly after the case start time included in the association information and ends slightly before or slightly after the case end time included in the association information. Thus, the target time range may be defined by target range start and end times that are within a threshold proximity of respective case start and end times included in the association information. For example, if the association information indicates a case start time of 10:00 am and a case end time of 10:15 am, the target time range may be 9:55 am to 10:20 am, 9:55 am to 10:16 am, 9:59 am to 10:20 am, 10:01 am to 10:15 am, 10:00 am to 10:14 am, or any other suitable range. Thus, it will be appreciated that the difference between the target range start time and the association information case start time is not necessarily the same as the difference between the target range end time and the association information case end time.

As shown in FIG. 5C, the process 500*c* starts with the patient encounter data source integration service 130 receiving 502*c* association information uploaded by the mobile computing device 104. The patient encounter data source integration service 130 can receive 502*c* within the process 500*c* by executing actions such as those executed by the patient encounter data source integration service 130 to receive 502*a* within the process 500*a* described above with reference to FIG. 5A.

The patient encounter data source integration service 130 generates 504*c* at least one search criterion that specifies that a case start time and a case end time included in one or more medical device case files are within a target time range. As noted above, the target time range is defined based on case start and end times included in the association information. In some implementations the target time range begins at the case start time included in the association information and ends at the case end time included in the association information. In other implementations the target time range begins slightly before or slightly after the case start time included in the association information and ends slightly before or slightly after the case end time included in the association information.

Continuing the process 500*c*, the patient encounter data source integration service 130 searches 506*c* for one or more case files that satisfy the at least one search criterion. In particular, the patient encounter data source integration service 130 searches for one or more medical device case files that include a case start time and a case end time that are within the specified target time range. For example, in one implementation the patient encounter data source integration service 130 generates 504*c* the at least one search criterion by defining the target time range based on relevant timestamps within the association information. In another implementation the patient encounter data source integration service 130 generates 504*c* the at least one search criterion by defining the target time range based on relevant time-stamps within the association information and applying a suitable threshold proximity to the target range start time and/or the target range end time. Thus, the target time range is not necessarily defined by the start and end times included in the association information. Where the patient encounter data source integration service 130 identifies 508*c* one or more case files to associate with the association information based on the at least one search criterion, the patient encounter data source integration service 130 stores 510*c* an integrated data source encounter structure and the process 500*c* ends. The patient encounter data source integration service 130 can store 510*c* within the process 500*c* by executing actions such as those executed by the patient encounter data source integration service 130 to store 510*a* within the process 500*a* described above with reference to FIG. 5A.

Figure 5D:
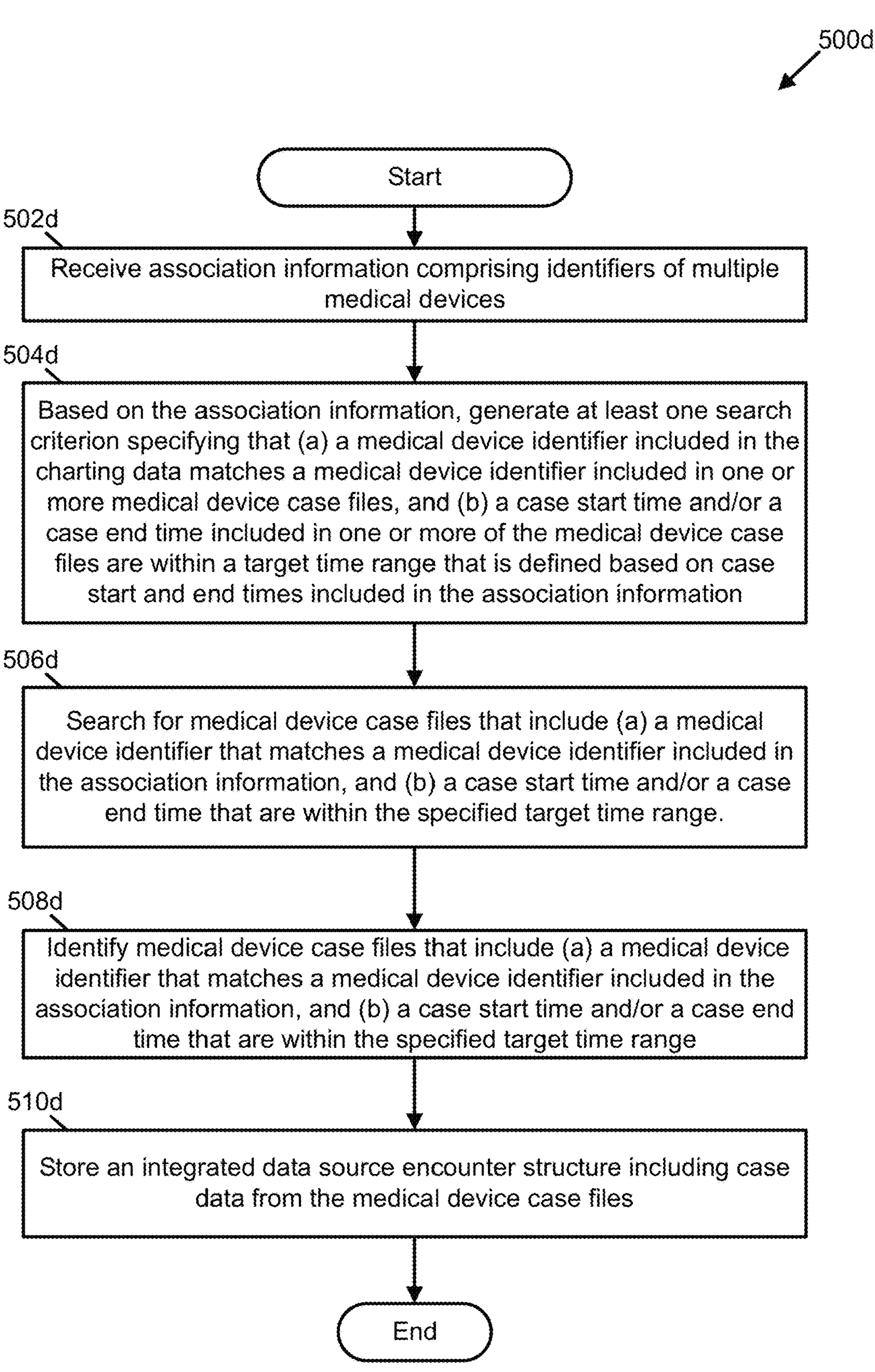
FIG. 5D is a flow diagram of a case file consolidation process executed by a patient encounter data source integration service in accordance with an example implementation that identifies medical device case files that include (a) medical device identifiers that match medical device identifiers included in association information, and (b) a case start time and a case end time that are within a target time range that is defined based on case start and end times included in association information.

FIG. 5D illustrates an example of an integration process 500*d* that is executed by the patient encounter data source integration service 130 and that identifies one or more medical device case files that include (a) a medical device identifier that matches (e.g., exactly or closely matching) a medical device identifier included in the association information, and (b) a case start time and a case end time that are within a "target time range" that is defined based on case start and end times included in the association information. As noted above, in some implementations the target time range begins at the case start time included in the association information and ends at the case end time included in the association information. In other implementations the target time range begins slightly before or slightly after the case start time included in the association information and ends slightly before or slightly after the case end time included in the association information. Thus, the target time range may be defined by target range start and end times that are within a threshold proximity of respective case start and end times included in the association information, as discussed previously with regards to FIGS. 5A-5C. The difference between the target range start time and the association information case start time is not necessarily the same as the difference between the target range end time and the association information case end time.

As shown in FIG. 5D, the process 500*d* starts with the patient encounter data source integration service 130 receiving 502*d* association information uploaded by the mobile computing device 104. The patient encounter data source integration service 130 can receive 502*d* within the process 500*d* by executing actions such as those executed by the patient encounter data source integration service 130 to receive 502*a* within the process 500*a* described above with reference to FIG. 5A.

The patient encounter data source integration service 130 generates 504*d* at least one search criterion that specifies that (a) a medical device identifier included in the association information matches (e.g., exactly or closely matching) a medical device identifier included in one or more medical device case files, and (b) a case start time and a case end time included in the one or more medical device case files are within a target time range. As noted above, the target time range is defined based on case start and end times included in the association information. In some implementations the target time range begins at the case start time included in the association information and ends at the case end time included in the association information. In other implementations the target time range begins slightly before or slightly after the case start time included in the association information and ends slightly before or slightly after the case end time included in the association information.

Continuing the process 500*d*, the patient encounter data source integration service 130 searches 506*d* for one or more case files that satisfy the at least one search criterion. In particular, the patient encounter data source integration service 130 searches for one or more medical device case files that include (a) a medical device identifier that matches (e.g., exactly or closely matching) a medical device identifier included in the association information, and (b) a case start time and a case end time that are within the specified time range. Where the patient encounter data source integration service 130 identifies 508*d* a case file to associate with the association information based on the at least one search criterion, the patient encounter data source integration service 130 stores 510*d* an integrated data source encounter structure and the process 500*d* ends. The patient encounter data source integration service 130 can store 510*d* within the process 500*d* by executing actions such as those executed by the patient encounter data source integration service 130 to store 510*a* within the process 500*a* described above with reference to FIG. 5A.

As noted above, a search criterion specifies at least one relationship between medical device case files and enables the identification of one or more of the medical device case files that have data to be integrated into an integrated data source encounter structure. FIGS. 5B through 5D illustrate example file integration processes, each of which uses one or more search criteria to search for and identify one or more medical device case files. Other search criteria can be used in these and other implementations, including one or more of the following: (i) a search criterion specifying that a case start time included in a medical device case file is within a threshold proximity of a case start time included in association information; (ii) a search criterion specifying that a case end time included in a medical device case file is within a threshold proximity of a case end time included in association information; (iii) a search criterion specifying that case start and end times included in a medical device case file are both within a target time range, wherein the target time range begins at a case start time included in association information and ends at a case end time included in the association information; and (iv) a search criterion specifying that case start and end times included in a medical device case file are both within a target time range, wherein the target time range begins at a specified duration before a case start time included in association information and ends at the specified duration after a case end time included in the association information. In implementations where a search criterion that relies on comparing timestamps included in association information with timestamps included in a medical device case file, optional adjustments can be included to account for different time standards upon which the timestamps in the association information and the timestamps in the medical device case file are based. Such differing time standards may be the result of using different time zones or using daylight savings time.

The various search criteria and methods described in FIGS. 5B, 5C, and 5D may depend upon various equipment configurations and capabilities. These configurations and capabilities may determine the manner in which the case start time, the case end time, and/or the medical device identifiers are recorded in the integrated data source encounter structure. For example, these values may be automatically recorded or manually entered or triggered. Further, these configurations and capabilities may determine whether one or more of the case start time, the case end time, and/or the medical device identifiers are available as search criteria. For example, in a system that lacks the capability to automatically record or prompt for one or more of the case start time, the case end time, and/or the medical device identifiers, one or more of these values may be unavailable for use as a search criteria. Finally, these configurations and capabilities may determine the relative reliability or accuracy of the case start time, the case end time, and/or the medical device identifiers as search criteria. For example, automatically recorded values may be more accurate and reliable than manually entered values.

The association information may include a case start time and a case end time. These times may be recorded automatically in, for example, a patient charting file or event log. In an implementation, these times may correspond to clock times on the mobile computing device 104. For example, the case start time may be the clock time at which a patient charting application or event log application opens and initiates a new charting file and the case end time may be the clock time at which the patient charting application or event log application closes the charting file. As another example, the patient charting application or event log application may receive a case start time transmitted from a computer aided dispatch (CAD) or other dispatch server or device to the mobile computing device 104 and record this time in the patient charting file or event log, which may be included as part of the association information. This case start time may correspond to a clock time at the CAD or dispatch server or device at the time the case is assigned to an EMS crew. As a further example, the time may correspond to a clock time on the mobile computing device 104 at which the EMS crew accepts a case assignment from the CAD or other dispatch server or device. In this scenario, the mobile computing device 104 may display the case assignment, prompt the user for an acceptance, and automatically record the acceptance time as the case start time in the patient charting file or event log. In some embodiments, a case start time may correspond to the time at which a user activates and/or initiates a case file with one or more of the medical devices associated with the medical event. As yet another example, the mobile computing device 104 may receive time at a patient transport destination (e.g., based on a WIFI or BLUETOOTH or other communicative coupling initiated at the transport destination) and automatically record this received time as the case end time. As yet a further example, the mobile computing device 104 may transmit the case file to the charting data store 134 and/or to a remote computing device 106 (e.g., a hospital server or other computing device at a patient transport destination) and the mobile computing device 104 may record the time of transmission as the case end time.

In an implementation, the mobile computing device 104 may receive and automatically record the case start time and/or the case end time from a geofencing application on the mobile computing device 104. For example, the geofencing application may provide a case start time to the mobile computing device 104 based on the mobile computing device 104 crossing a geofence around an EMS agency location or around a patient location. As another example, the geofencing application may provide a case end time to the mobile computing device 104 based on the mobile computing device 104 crossing a geofence around a patient location or around a patient transport destination (e.g., a hospital, a doctor's office, a dialysis center, a psychiatric center, or other care provider location). Similarly, the mobile computing device 104 may receive and automatically record the case start time and/or the case end time based on one or more GPS coordinates of the mobile computing device 104.

In some implementations, the case start time may be a time of treatment (e.g., a time that defibrillation shock, drug, or other therapy was delivered to the patient by the medical device. The medical device also records times at which the device provides therapy (e.g., as a time-stamped event marker). Thus, a correlation between "case start time" may include a correlation between therapy delivery times as recorded in the association information and in the medical device case file. The association information may receive this information from the medical device (e.g., as transmitted information) or may receive this information via an entry to the association information.

In an implementation, mobile computing device 104 may prompt the user to enter or confirm a case start time and/or a case end time at the ePCR application 122 or the event log application 140. The mobile computing device 104 may record this user entered or confirmed time in the association information. In this case, the recorded time may be a clock time on the mobile computing device 104 confirmed by the user or may be a time gathered from a watch or other time source separate from the mobile computing device 104 and entered into the association information by the user.

For case times and other entries to the association information as discussed herein, these entries may be manual entries (e.g., via a keyboard), audio entries (e.g., via a microphone and a speech recognition capability at the mobile computing device 104), entries captured via an augmented reality device, and/or entries captured at a wearable device that either communicates with the mobile computing device 104 or servers 108.

In some scenarios, the case end time may lag behind the actual discharge of the patient from the care of EMS. For example, an EMS crew may transport a patient to a hospital, discharge the patient to the hospital, and then proceed to complete the patient chart. This lag time may be necessary operationally if the EMS crew does not have time to complete patient charting during the patient care because they do not have time to divert their attention from the patient care to the task of patient charting. Thus, even if a communicative coupling exists between the mobile computing device 104 and the medical device(s) 102A-102N with a sufficient bandwidth and signal strength to transfer files between these devices, the file association may still need to occur in the cloud because the association information may not be complete until some time after the event. At this time, the relevant medical device(s) may be redeployed or powered off. Additionally, in some cases, for privacy and data protection reasons, a caregiver must manually initiate or confirm a file transfer from a medical device to a mobile computing device. If the caregiver forgets to initiate this transfer, the file association can still occur in the cloud rather than based on a device to device transfer. Furthermore, the medical devices, the patient charting application, and/or the event log application may be from different vendors and may not be compatible with one another in terms of file formats. Therefore, even with an available communications channel, in the absence of an appropriate software development kit (SDK), file transfers between these devices may not be possible and may require a file association in the cloud as described herein.

The case end time may correspond to a completion of the association information or a time entered by the user. In various implementations, the case start time in the association information may be a time at which a caregiver arrives at the patient scene (e.g., an "at patient side time") and the case end time may be a time at which the patient is discharged from the care of EMS (e.g., a "time of patient care transfer"). The time at which the caregiver arrives at the patient scene may be the earliest time at which a medical device could be deployed and/or activated for use on the patient. Thus, this time may be the relevant case start time. Similarly, the time at which the patient care is transferred away from EMS is the latest time at which a medical device could be detached from the patient and/or deactivated. In some embodiments, a case end time may correspond to the time at which a user deactivates and/or closes a current case file with one or more of the medical devices associated with the medical event. Typically, upon arrival at a transport destination, such as a hospital, a patient is transferred from medical devices belonging to the EMS agency to those belonging to the hospital.

During care of the patient, the EMS crew may couple the patient to one or more medical devices. The medical device may automatically record a case start time or a case end time as a time of power on or power off or as a time at which a patient interface device is coupled to or removed from the patient. The medical device may recognize this coupling or removal based on the presence or absence of a physiologic signal from the patient or based on a sensor signal that indicates a patient connection (e.g., a closed circuit based on a proper attachment of a pair of electrodes to a patient) or based on a sensor signal indicating that a patient interface device has been removed from a package or otherwise deployed. In an implementation, a medical device and a mobile computing device may communicatively couple and one or more both devices may record a case start time and/or a case end time based on a time associated with the initiation of communications. In an implementation, a medical device may request a user entry or confirmation of a case start time or a case end time.

In an implementation, the medical device(s) 102A-102N may automatically record a device identifier in the medical device case file. For example, this device identifier may be a code unique to the particular medical device (e.g., a serial number and/or model number and/or other identifying information) included as metadata with the medical device case file. In an implementation, the medical device(s) 102A-102N may communicatively couple with the mobile computing device 104 and transmit the medical device identifier to the mobile computing device 104. The mobile computing device 104 may automatically record this identifier in the association information. In an implementation, the medical device(s) 102A-102N may include the medical device identifier on an exterior housing, for example, on an affixed tag or sticker or as an embossed or engraved code. The caregiver may visually inspect this code and manually enter the code at the ePCR application 122 or the event log application 140. Alternatively, the caregiver may capture the code using a camera or other visual recording device and transmit the captured code to the mobile computing device 104 for recordation in the association information. As another option, the medical device identifier may be a bar code or QR code and the caregiver may capture the code using a scanner and transmit the captured code to the mobile computing device 104 for recordation in the association information. In an implementation, the mobile computing device 104 may include the camera and/or the scanner. As a further option, the caregiver may read and vocalize the code and the mobile computing device 104 may include a microphone configured to capture the audible information and automatically record the code in the association information. In an implementation, particular medical devices may be associated with a particular EMS crew and/or EMS vehicle. In such an implementation, the caregiver may provide a crew or vehicle identification to the association information and the mobile computing device 104 may consult a look-up table or other reference to associated a medical device identifier with the association information based on the crew or vehicle identification.

Given the various possible modes of time recordation on the mobile computing device 104 and the medical device(s) 102A-102N, the reliability and accuracy of any correlation, or match, between the times in the association information and the medical device case file may vary to differing degrees depending on how each device records these times. Similarly, the various possible modes of capturing and recording the medical device identifier by the mobile computing device 104 may determine the reliability and accuracy of any correlation, or match between the information in the association information and in the medical device case file. Therefore, a system may use one or other or both of these criteria, as exemplified in FIGS. 5B, 5C, and 5D, as search criteria for file associations.

Use of both of these criteria may be not be necessary for a small EMS agency that owns only one or a few medical devices, such as defibrillators, automated compression devices, ventilators, etc. and/or has only one or a few medical devices deployed simultaneously (e.g., for two concurrent emergencies or scheduled transports). In this case, the times may be sufficient to associate the medical device case files and the association information. However, for a large EMS agency, such as an agency in a major metropolitan area, the agency may own 100-200 medical devices and may have 10-20 concurrent deployments. In this case, the times may be insufficient and the medical device identifiers may be needed in conjunction with the times for accuracy of the file associations. This situation may be particularly true for a mass casualty situation where the times would substantially overlap between patients and there may be confusion in the field regarding timely recordation of medical device identifiers. Therefore, in this case, the search criterion may require several parameters for reliable and accurate file associations. A multiple or mass casualty situation also provides another example of a situation in which a file association may need to occur in the cloud even if a communicative coupling exists between the mobile computing device 104 and the medical device(s) 102A-102N with a sufficient bandwidth and signal strength to transfer files between these devices. For example, if a long range communicative coupling such as WIFI or cellular is unavailable (e.g., in an interior space, a parking garage, an urban canyon, a remote location, etc.), the devices may only be able to communicate via a short range connection such as BLUETOOTH. However, multiple devices within short range communications distance of one another may interfere with detection capabilities that enable an automatic transfer of files between the medical devices and the mobile computing device.

Figures 6, 7:
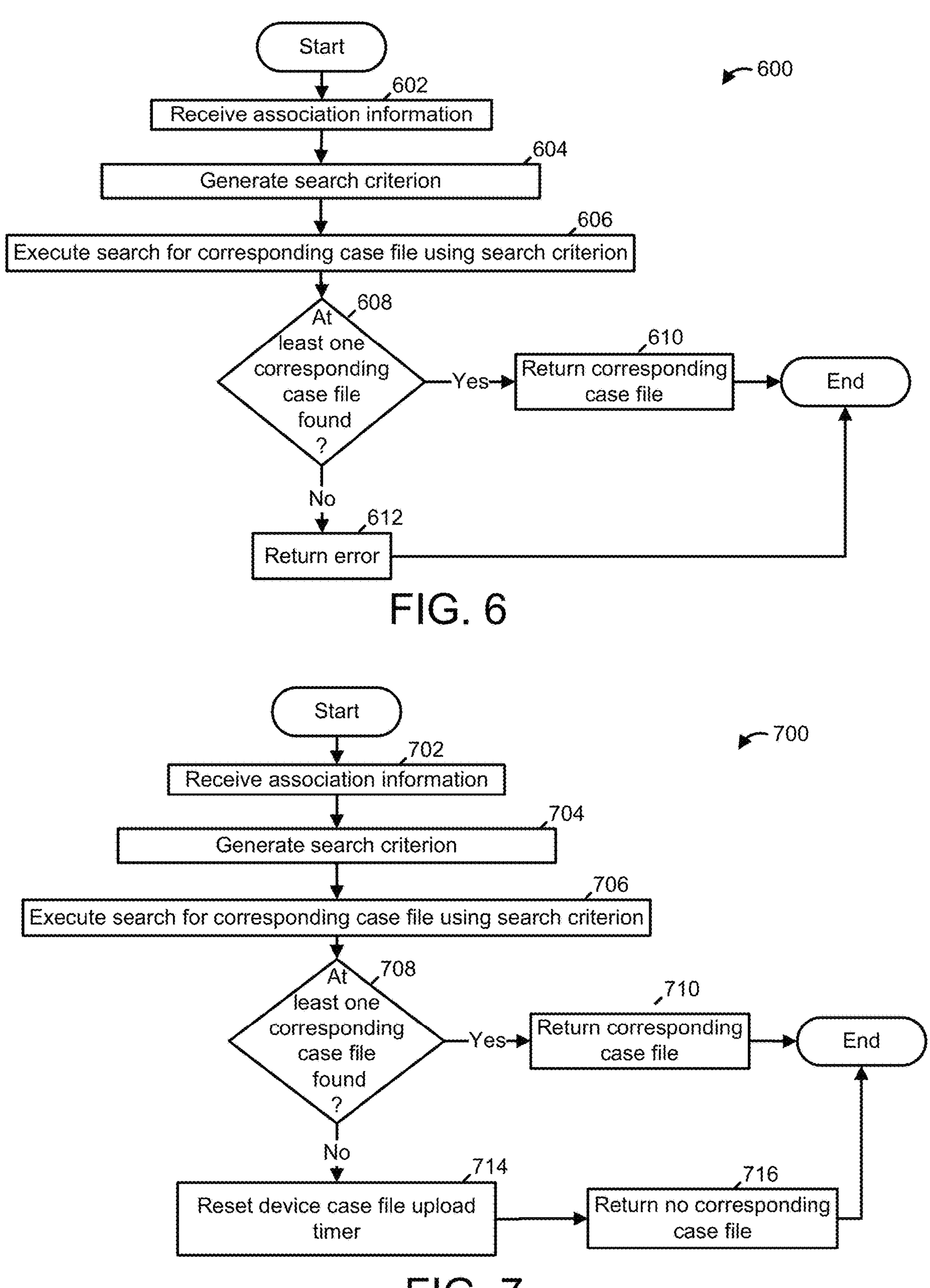
FIG. 6 is a flow diagram of a case file data source integration process executed by a patient encounter data source integration service in accordance with at least one example disclosed herein.
FIG. 7 is a flow diagram of case file data source integration process executed by a patient encounter data source integration service in accordance with at least one example disclosed herein.

FIG. 6 illustrates one example of an associating process 600 executed by a patient encounter data source integration service (e.g., the patient encounter data source integration service 130 of FIG. 1) in some implementations. The patient encounter data source integration service can be configured to execute the process 600 in response to an event, such as expiration of a periodic timer and/or a request from a calling process (e.g., the ePCR API 128 and or the event log API 144 of FIG. 1).

As shown in FIG. 6, the process 600 starts with the patient encounter data source integration service receiving 602 association information. This association information may be included in a message from the calling process or stored with charting data or event log data processed by the patient encounter data source integration service in response to expiration of the periodic timer. After receiving 602 the association information, the patient encounter data source integration service generates 604 at least one search criterion based on the association information and searches 606 case data stored in a case data store (e.g., the case data store 132 of FIG. 1) for one or more case files that match or satisfy the at least one search criterion. In some examples, the patient encounter data source integration service can receive 602, generate 604, and search 606 within the process 600 by executing actions such as those executed by the patient encounter data source integration service to receive 502, generate 504, and search 506 within the process 500 described above with reference to FIG. 5.

Next, the patient encounter data source integration service determines 608 whether at least one corresponding case file was identified by the search 606. Where the patient encounter data source integration service determines 608 that at least one corresponding case file was not found, the patient encounter data source integration service generates and returns 612 an error message to the calling process, and the process 600 ends. Where the patient encounter data source integration service determines 608 that at least one corresponding case file was found, the patient encounter data source integration service returns 610 a message including the at least one corresponding case file or at least one identifier thereof to the calling process, and the process 600 ends.

FIG. 7 illustrates one example of an associating process 700 executed by a patient encounter data source integration service (e.g., the patient encounter data source integration service 130 of FIG. 1) in some implementations. The patient encounter data source integration service can be configured to execute the process 700 in response to an event, such as expiration of a periodic timer and/or a request from a calling process (e.g., the ePCR API 128 of FIG. 1).

As shown in FIG. 7, the process 700 starts with the patient encounter data source integration service receiving 702 association information. This association information may be included in a message from the calling process or stored with charting data or event log data processed by the patient encounter data source integration service in response to expiration of the periodic timer. After receiving 702 the association information, the patient encounter data source integration service generates 704 at least one search criterion based on the association information and searches 706 case data stored in a case data store (e.g., the case data store 132 of FIG. 1) for one or more case files that match or satisfy the at least one search criterion. In some examples, the patient encounter data source integration service can receive 702, generate 704, and search 706 within the process 700 by executing actions such as those executed by the patient encounter data source integration service to receive 502, generate 504, and search 506 within the process 500 described above with reference to FIG. 5.

Next, the patient encounter data source integration service determines 708 whether at least one corresponding case file was identified by the search 706. Where the patient encounter data source integration service determines 708 that at least one match was not found, the patient encounter data source integration service resets 714 resets a timer (e.g., the event-triggering periodic timer described above) and transmits 716 a return message to the calling process that indicates no corresponding case file was found. Where the patient encounter data source integration service determines 708 that at least one corresponding case file was found, the patient encounter data source integration service returns 710 the at least one corresponding case file or at least one identifier thereof to the calling process, and the process 700 ends.

Figure 8:
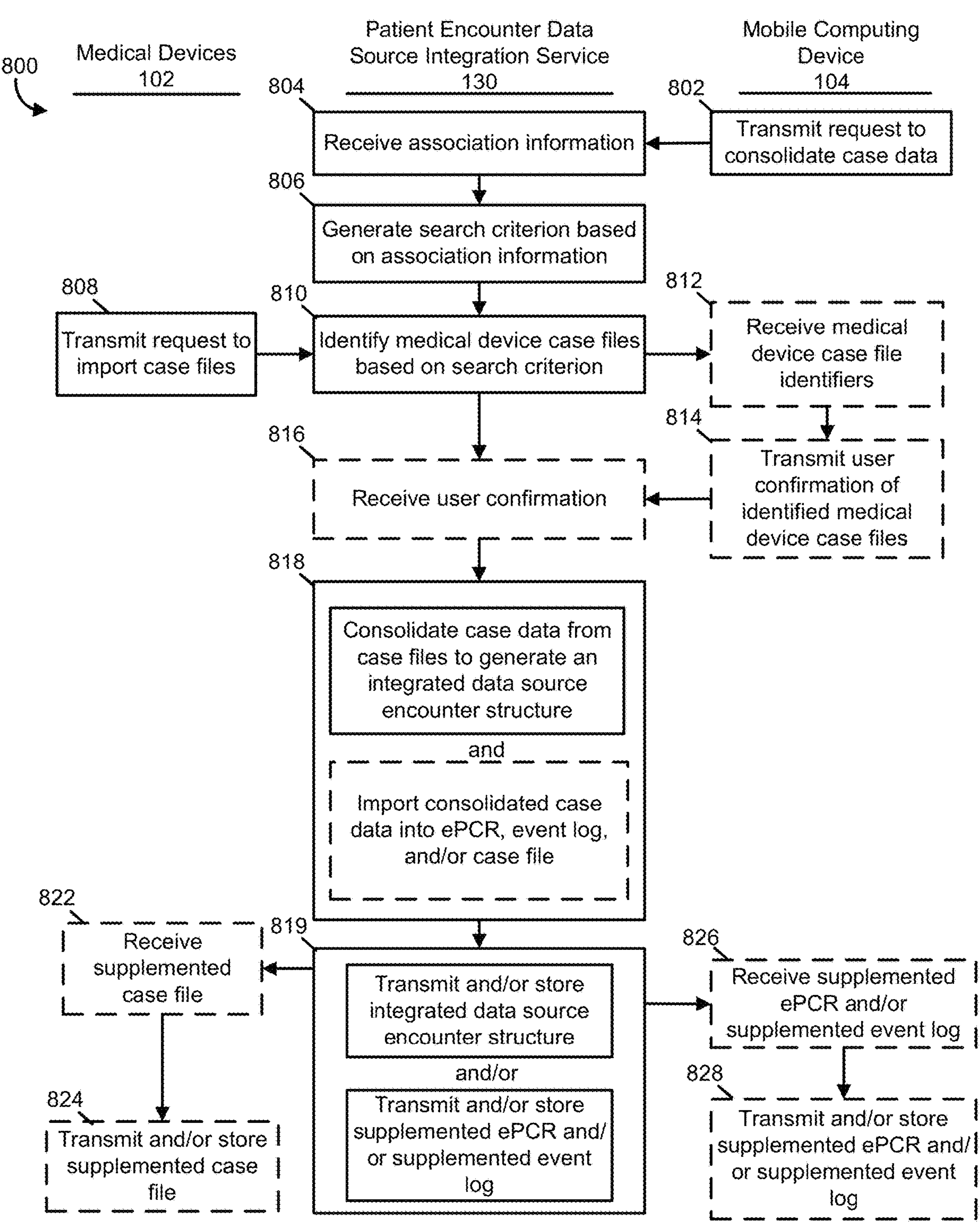
FIG. 8 is a flow diagram of a consolidation process executed by a medical device, a charting device, and a patient encounter data source integration service in accordance with at least one example disclosed herein.

FIG. 8 illustrates one example of a consolidation process 800 executed by a plurality of medical devices, a patient encounter data source integration service, and a mobile computing device (e.g., the medical devices 102, the patient encounter data source integration service 130 and a mobile computing device 104 of FIG. 1) in some implementations. As shown in FIG. 8, operations rendered with dashed line boarders may not present in some examples.

Within the process 800, the mobile computing device transmits 802 a request message to the patient encounter data source integration service. This request message can include a request to associate to case data (e.g., a medical device case file or a portion thereof) from multiple medical device case files to one another. The request message can include association information to be used to develop at least one search criterion and/or an identifier of such association information to be (e.g., an identifier of charting data and/or event log data that subsumes the association information within a charting data store and/or an event log data store, such as the charting data store 134 and/or the event log data store 146 of FIG. 1). In some examples, the mobile computing device can transmit the request message and/or the association information to the patient encounter data source integration service via one or more messages to an ePCR interface and/or an event log interface (e.g., the ePCR API 128 and/or the event log API 144 of FIG. 1) implemented by a server (e.g., a server of the server(s) 108 of FIG. 1). Alternatively or additionally, the mobile computing device can store the association information within the charting data store and/or the event log data store via the ePCR interface and/or the event log interface as part of transmitting 802 the request message.

Continuing the process 800, the patient encounter data source integration service receives 804 the association information from the ePCR interface and/or the event log interface or the charting data store and/or the event log data store. This action is followed by the patient encounter data source integration service generating 806 at least one search criterion based on the association information. In some examples, the patient encounter data source integration service can receive 804 and generate 806 within the process 800 by executing actions such as those executed by the patient encounter data source integration service to receive 502 and generate 504 within the process 500 described above with reference to FIG. 5.

As shown in FIG. 8, the medical devices transmit 808 one or more request messages to a case interface (e.g., the case API 126) implemented by a server (e.g., a server of the server(s) 108 of FIG. 1). The request messages can include one or more requests to import a plurality of case files into a case data store (e.g., the case data store 132 of FIG. 1). The request messages can include the case files to be imported. In response to receiving the request messages, the case interface can receive the case files, parse the case files to retrieve case data from the case files, store the case data and/or the case files in the case data store, and transmit one or more response messages to the medical devices that indicate results of processing the request messages.

Continuing the process 800, the patient encounter data source integration service identifies 810 case data associated with the imported case files as satisfying the at least one search criterion. In some examples, the patient encounter data source integration service can identify 810 within the process 800 by executing actions such as those executed by the patient encounter data source integration service in identifying 508 within the process 500 described above with reference to FIG. 5. The patient encounter data source integration service can further generate and transmit a confirmation request including one or more identifiers of case files and/or other metadata descriptive of the case files to the mobile computing device as part of identifying 810 the case files. The one or more identifiers of the case files can include, for example, one or more timestamps indicating when the case files were created by the medical devices and identifiers of medical devices that generated the case files.

Figure 9:
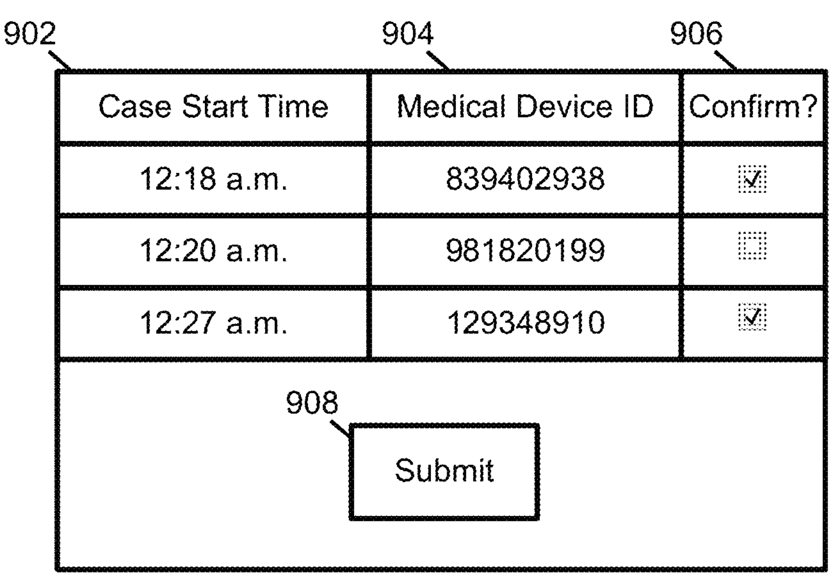
FIG. 9 is a view of a user interface screen provided by an ePCR application to request confirmation of one or more medical device case files in accordance with at least one example disclosed herein.

Continuing with the process 800, the mobile computing device receives 812 the confirmation request including the identifiers and/or other metadata of the case files from the patient encounter data source integration service and prompts a user (e.g. the healthcare provider 118A of FIG. 1) to confirm whether the case files are descriptive of the same patient encounter. In some examples, the mobile computing device prompts the user via an ePCR application and/or an event log application (e.g., the ePCR application 122 and/or the event log application 140 of FIG. 1) using the identifiers. FIG. 9 illustrates one example of a user interface screen 900 that the ePCR application and/or the event log application is configured to render in response to receiving a confirmation request. As shown in FIG. 9, the screen 900 includes columns of case controls 902 and 904; a column of confirmation controls 906; and a submit control 908. The case controls 902 and 904 are configured to display the identifiers of and information regarding the case files identified in the confirmation request. More specifically, each of the case controls 902 is configured to display a case start time and each of the case controls 904 is configured to display an identifier of the medical device that generated the case file. The confirmation controls 906 are configured to receive input indicating whether the case file identified by the row in which the confirmation control 906 resides is confirmed or not confirmed to be associated for other case files (e.g., that each was generated during the same patient encounter). The submit control 908 is configured to receive input indicating that the user has confirmed or not confirmed the case files as desired.

Returning to the process 800, where the ePCR application and/or the event log application receives input confirming the case files (e.g., selection of the submit control 908), the ePCR application and/or the event log application transmits 814 a confirmation response to the patient encounter data source integration service (e.g., via the ePCR interface and/or the event log interface). The patient encounter data source integration service receives 816 the confirmation response.

In some examples, the patient encounter data source integration service consolidates 818 the case data from the associated case files into consolidated case data in an integrated data source encounter structure. For instance, in some examples, the patient encounter data source integration service consolidates 818 the case data into consolidated case data by establishing associations between all, or a portion of, the records of case data stored in the case data store that originated from the associated case files. Further, the patient encounter data source integration service can integrate the consolidated case data, or a portion thereof, with charting data and/or event log data by, for example, importing at least a portion of the consolidated case data into an ePCR and/or an event log as part of the integrated data source encounter structure. This consolidation generates supplemented ePCRs and/or supplemented event logs. Moreover, the patient encounter data source integration service can integrate the consolidated case data, or a portion thereof, with one or more case files of the associated case files by, for example importing at least a portion of the consolidated case data into the one or more case files. This consolidation generates supplemented case files.

Continuing the process 800, the patient encounter data source integration service stores and/or transmits 819 the consolidated case data to the medical devices and/or the mobile computing device. For instance, in some examples, the patient encounter data source integration service stores the supplemented case files in the case data store and/or transmits 819 the supplemented case files to the medical devices. Alternatively or additionally, in some examples, the patient encounter data source integration service stores the supplemented ePCR and/or supplemented event log in the charting data store and/or transmits 819 the supplemented ePCR and/or the supplemented event log to the mobile computing device.

Where the patient encounter data source integration service transmits 819 the supplemented case files to the medical devices, the medical devices receive 822 the supplemented case files and transmit and/or locally store 824 the supplemented case files. Where the patient encounter data source integration service transmits 819 the supplemented ePCR and/or the supplemented event log to the mobile computing device, the mobile device receives 826 the supplemented ePCR and/or the supplemented event log and transmits and/or locally stores 828 the supplemented ePCR and/or the supplemented event log.

Figure 10:
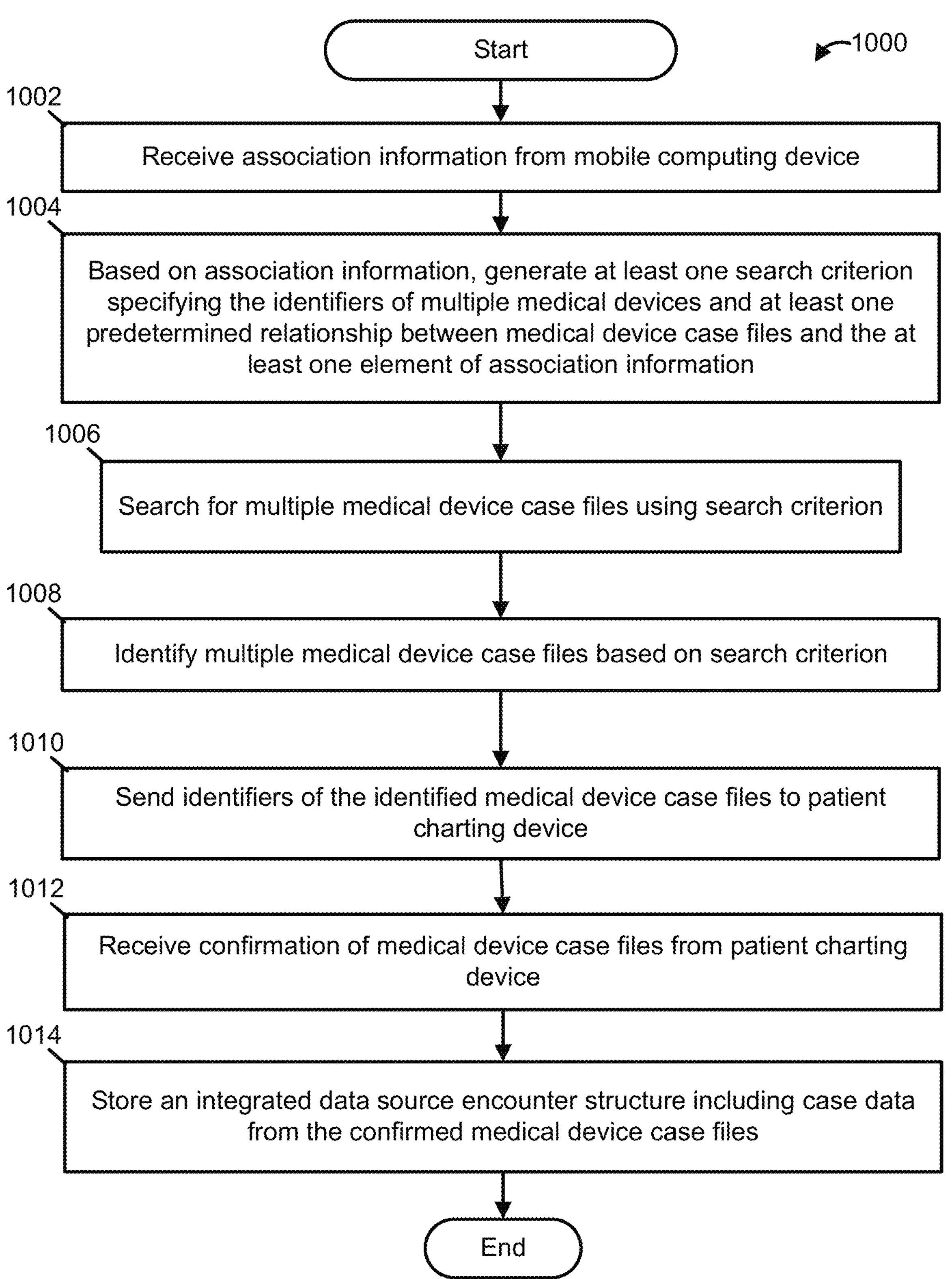
FIG. 10 is a flow diagram of a case file consolidation process executed by a charting device and a patient encounter data source integration service in accordance with at least one example disclosed herein.

FIG. 10 illustrates one example of a consolidation process 1000 executed by a patient encounter data source integration service and a mobile computing device (e.g., the patient encounter data source integration service 130 and the mobile computing device 104 of FIG. 1) in some implementations.

As shown in FIG. 10, the process 1000 starts with the patient encounter data source integration service receiving 1002 association information from the mobile computing device. This action is followed by the patient encounter data source integration service generating 1004 at least one search criterion based on the association information, searching 1006 case data stored in a case data store (e.g., the case data store 132 of FIG. 1) for a plurality of medical device case files that match or satisfy the at least one search criterion, and identifying 1008 the medical device case files as being associated with one another and a specific patient encounter based on the at least one search criterion. In some examples, the patient encounter data source integration service can receive 1002, generate 1004, search 1006, and identify 1008 within the process 1000 by executing actions such as those executed by the patient encounter data source integration service to receive 502, generate 504, search 506, and identify 508 within the process 500 described above with reference to FIG. 5.

Next, the patient encounter data source integration service transmits 1010 identifiers of the identified case files to the mobile computing device. These identifiers can include a timestamp indicating when the case files were generated by the medical devices. In some examples, the patient encounter data source integration service transmits 1010 the timestamps to an ePCR application and/or an event log application (e.g., the ePCR application 122 and/or the event log application 140 of FIG. 1) hosted by the mobile device. In certain examples, the mobile computing device receives the identifiers of the case files from the patient encounter data source integration service and prompts a user (e.g. the healthcare provider 118A of FIG. 1) to confirm whether the case files are descriptive of the same patient encounter. In some examples, the mobile computing device prompts the user via the ePCR application and/or the event log application. Where the ePCR application and/or the event log application receives input confirming the case files, the ePCR application and/or the event log application transmits a confirmation message to the patient encounter data source integration service (e.g., via an ePCR interface and/or an event log interface such as the ePCR interface 126 and/or the event log API 144 of FIG. 1).

Continuing the process 1000, the patient encounter data source integration service receives 1012 the confirmation message from the patient mobile computing device, stores 1014 an integrated data source encounter structure including case data from the confirmed case files (which may be streaming real-time from medical device(s) during the patient encounter), and the process 1000 ends. In some examples, the patient encounter data source integration service can store 1014 the integrated data source encounter structure within the process 1000 by executing actions such as those executed by the patient encounter data source integration service to store 510 an integrated data source encounter structure within the process 500 described above with reference to FIG. 5.

Figure 11:
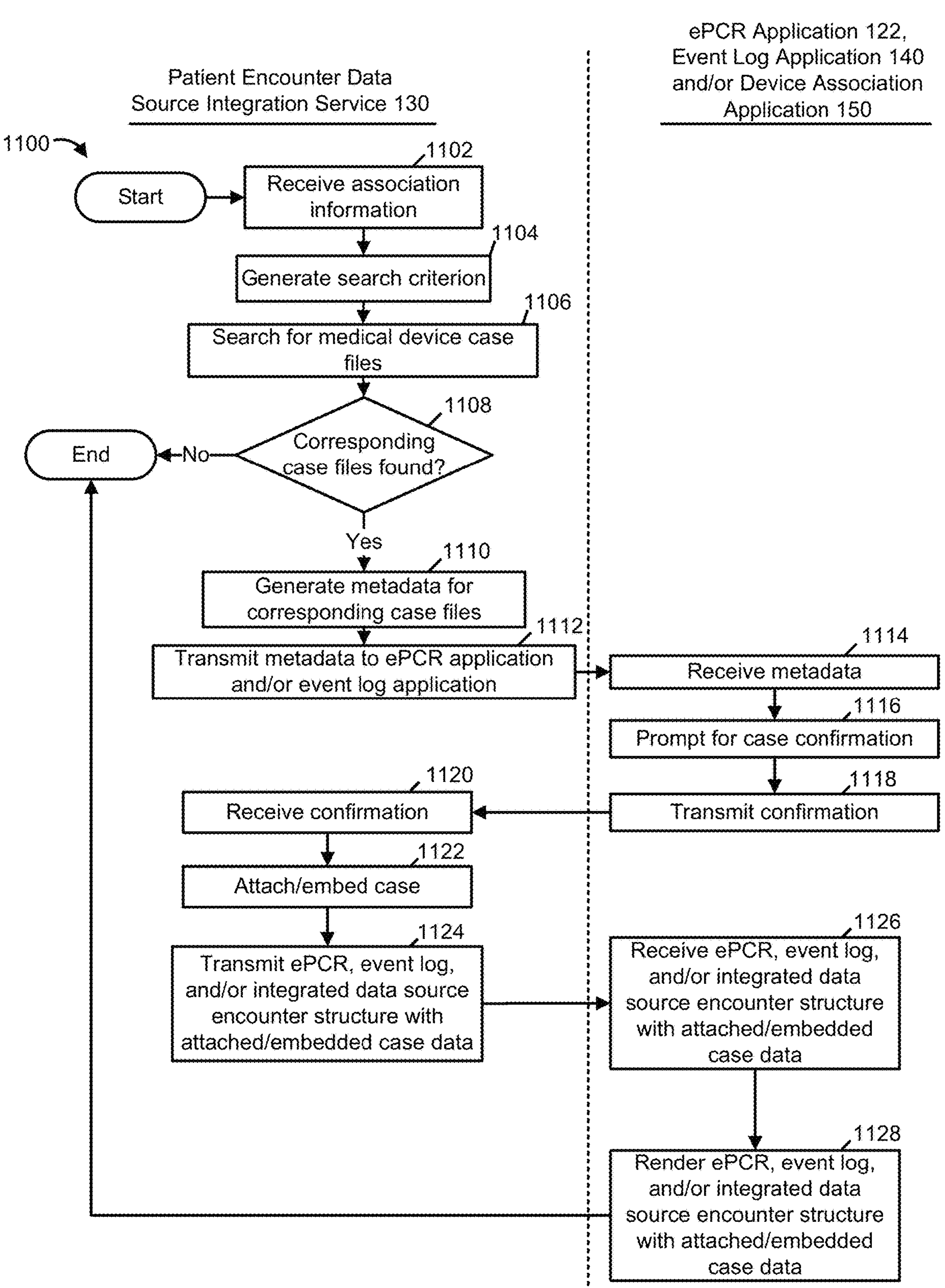
FIG. 11 is a flow diagram of a consolidation process with user confirmation executed by a charting device and a patient encounter data source integration service in accordance with at least one example disclosed herein.

FIG. 11 illustrates one example of a consolidation process 1100 executed by a patient encounter data source integration service and an ePCR application, an event log application, and/or a device association application hosted by a mobile computing device (e.g., the patient encounter data source integration service 130, the ePCR application 122, the event log application 140 and/or patient encounter device association application 150, and the mobile computing device 104 of FIG. 1) in some implementations.

As shown in FIG. 11, the process 1100 starts with the patient encounter data source integration service receiving 1102 association information. This action is followed by the patient encounter data source integration service generating 1104 at least one search criterion based on the association information and searching 1106 case data stored in a case data store (e.g., the case data store 132 of FIG. 1) for a plurality of medical device case files that match of satisfy the at least one search criterion. In some examples, the patient encounter data source integration service can receive 1102, generate 1104, and search 1106 within the process 1100 by executing actions such as those executed by the patient encounter data source integration service to receive 502, generate 504, and search 506 within the process 500 described above with reference to FIG. 5.

Next, the patient encounter data source integration service determines 1108 whether the search resulted in identification of one or more case files that match or satisfy the at least one search criterion. Where the patient encounter data source integration service determines 1108 that no corresponding case files were identified, the process 1100 ends. Where the patient encounter data source integration service determines 1108 that one or more corresponding case files were identified, the patient encounter data source integration service generates 1110 metadata descriptive of the corresponding case files. This metadata can include identifiers of the corresponding case files, such as timestamps indicating when the corresponding case file was created by medical devices, identifiers of the medical devices that created the corresponding case files, and/or identifiers of one or more mobile computing devices coupled with the medical devices during creation of the case files, among other identifiers.

Continuing the process 1100, the patient encounter data source integration service transmits 1112 the metadata to the ePCR application, the event log application, and/or the device association application over a network (e.g., the network 112 of FIG. 1). In some examples, the patient encounter data source integration service transmits the metadata via messages generated by one or more interface calls (e.g., calls supported by the ePCR API 128 and/or the event log API 144 of FIG. 1). These messages can include a confirmation request.

The ePCR application, the event log application, and/or the device association application receives 1114 the metadata and renders 1116 a prompt for each case file described in the metadata. For instance, the ePCR application, the event log application, and/or the device association application can render a timestamp and/or a medical device identifier for each case file within its associated prompt. Each of the one or more prompts can be configured to receive input confirming that its associated case file is descriptive of operation of a medical device coupled to a patient (e.g., the patient 116 of FIG. 1) during an encounter associated with the association information. In response to receiving input confirming a case file, the ePCR application, the event log application, and/or the device association application transmits 1118 a confirmation response to the patient encounter data source integration service (e.g., via the ePCR interface and/or the event log interface). The confirmation response can include an identifier of each confirmed case file.

Next, the patient encounter data source integration service receives 1120 the confirmation response and parses the confirmation response to retrieve identifiers of case files stored therein. The patient encounter data source integration service attaches and/or embeds 1122 the case files into an integrated data source encounter structure. This integrated data source encounter structure can be attached and/or embedded into ePCRs and/or event logs. The case files can be embedded and/or attached in whole or in part. Where the case files are embedded, case data stored within the case files can be stored in fields of the ePCR and/or in fields of the event log.

Continuing the process 1100, the patient encounter data source integration service transmits 1124 the ePCR, the event log, and/or the integrated data source encounter structure containing the attached/embedded case data to the ePCR application, the event log application, and/or the device association application. The ePCR application, the event log application, and/or the device association application receives 1126 the ePCR with the attached/embedded case data, the event log with the attached/embedded case data, and/or the integrated data source encounter structure and renders 1128 the ePCR, event log and/or the integrated data source encounter structure for review and manipulation by the healthcare provider.

Figure 12:
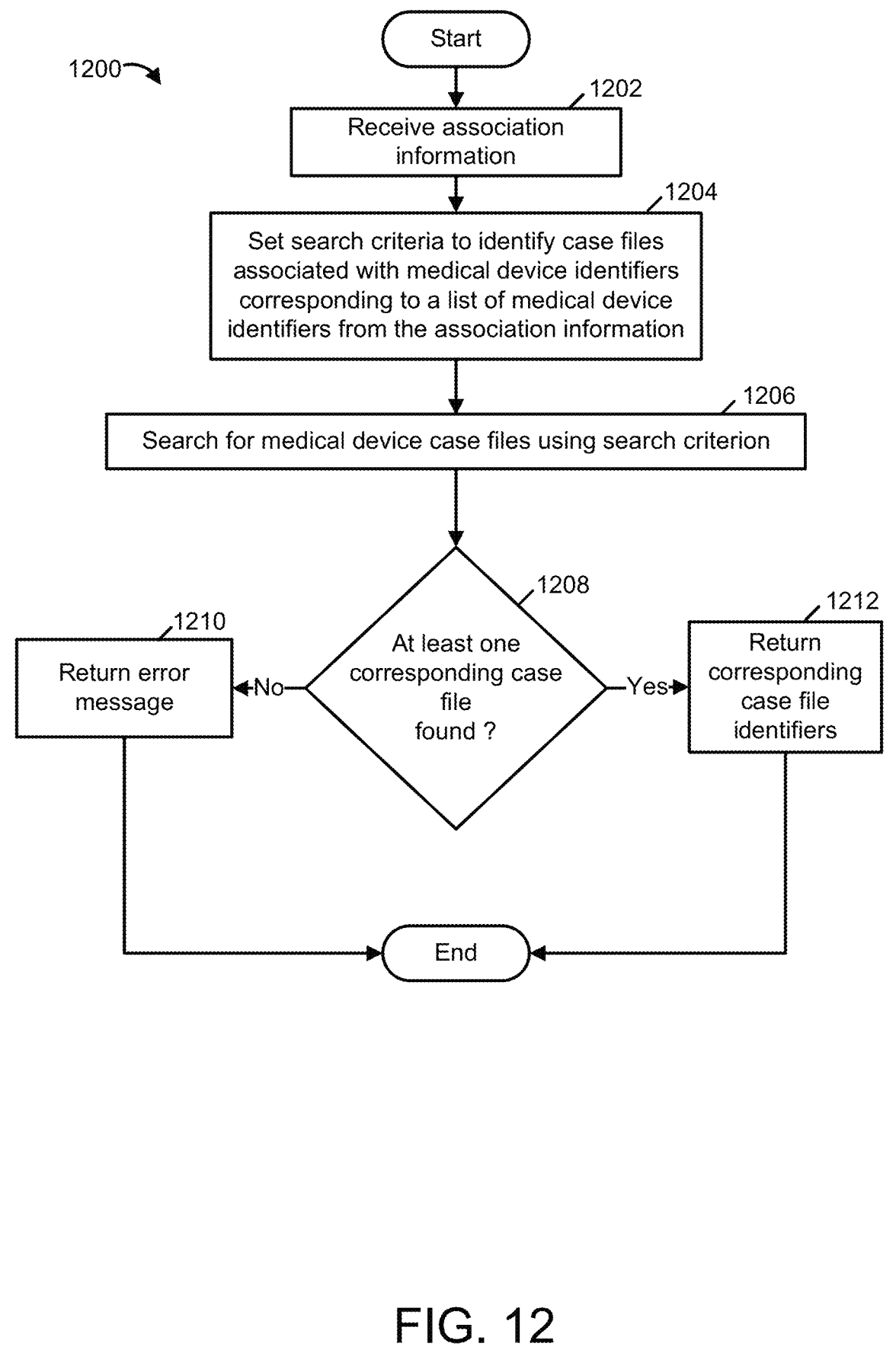

FIG. 12 illustrates one example of an associating process 1200 executed by a patient encounter data source integration service (e.g., the patient encounter data source integration service 130 of FIG. 1) in some implementations. The patient encounter data source integration service can be configured to execute the process 1200 in response to an event, such as expiration of a periodic timer and/or a request from a calling process (e.g., the ePCR API 128 and or the event log API 144 of FIG. 1).

As shown in FIG. 12, the process 1200 starts with the patient encounter data source integration service receiving 1202 association information. This action is followed by the patient encounter data source integration service generating 1204 at least one search criterion based on the association information and searching 1206 case data stored in a case data store (e.g., the case data store 132 of FIG. 1) for multiple medical device case files that match or satisfy the at least one search criterion. In some examples, the patient encounter data source integration service can receive 1202, generate 1204, and search 1206 within the process 1200 by executing actions such as those executed by the patient encounter data source integration service to receive 502, generate 504, and search 506 within the process 500 described above with reference to FIG. 5. However, within the process 1200, the patient encounter data source integration service generates 1204 at least one search criterion that specifies a list of medical device identifiers from the association information, one of which must equal a medical device identifier associated with a case file for the case file to be a corresponding case file. The patient encounter data source integration service uses this search criterion to search 1206 for associating case files.

Next, the patient encounter data source integration service determines 1208 whether at least one corresponding case file was identified by the search 1206. Where the patient encounter data source integration service determines 1208 that no corresponding case files were found, the patient encounter data source integration service generates and returns 1210 an error message indicating no corresponding case file was found to the calling process, and the process 1200 ends. Where the patient encounter data source integration service determines 1208 that at least one corresponding case file was found, the patient encounter data source integration service generates and returns 1212 the at least one corresponding case file or at least one identifier thereof to the calling process, and the process 1200 ends.

Figure 13:
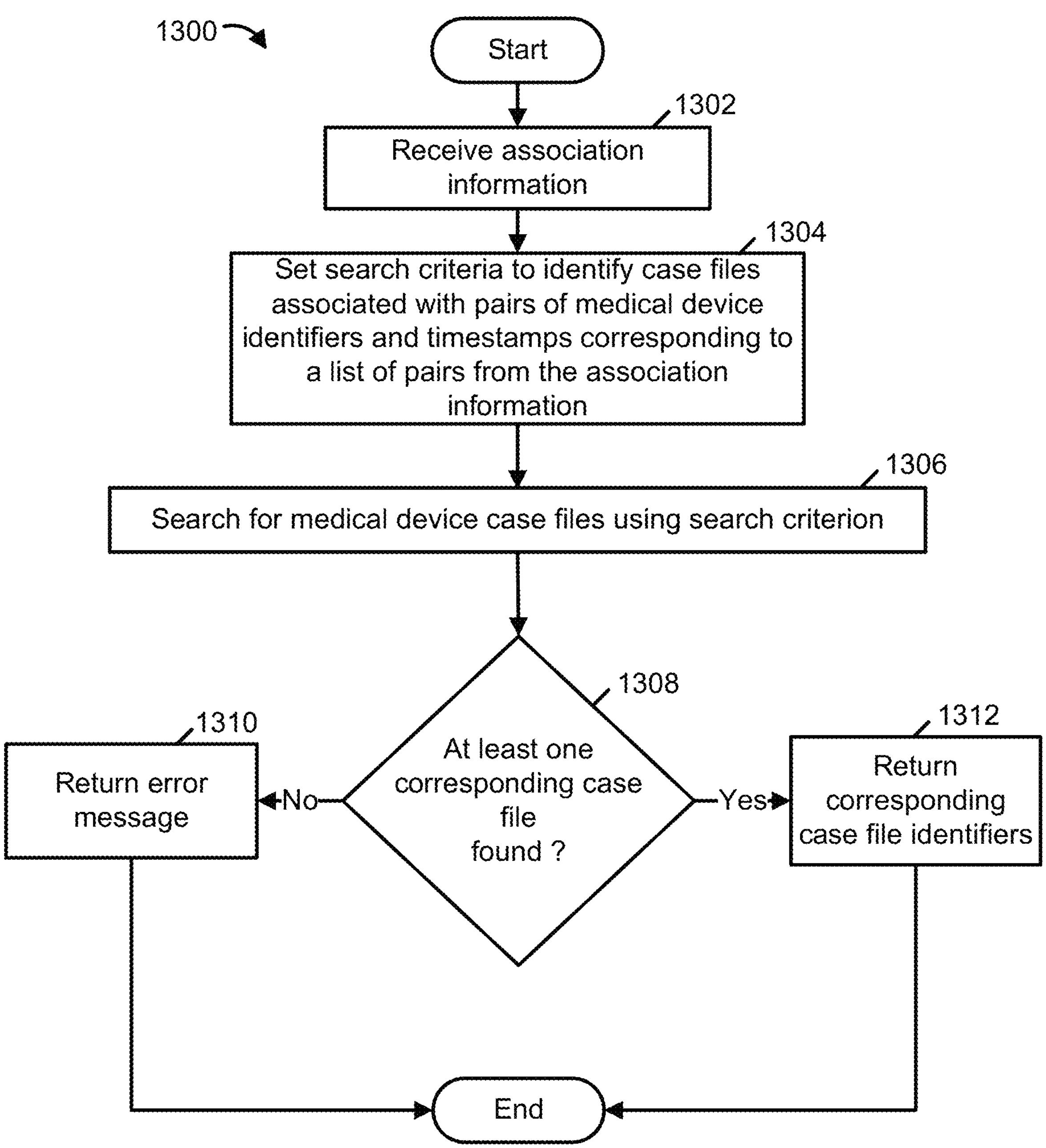
FIG. 13 is a flow diagram of a case file data source integration process executed by a patient encounter data source integration service in accordance with at least one example disclosed herein.

FIG. 13 illustrates one example of an associating process 1300 executed by a patient encounter data source integration service (e.g., the patient encounter data source integration service 130 of FIG. 1) in some implementations. The patient encounter data source integration service can be configured to execute the process 1300 in response to an event, such as expiration of a periodic timer and/or a request from a calling process (e.g., the ePCR API 128 and or the event log API 144 of FIG. 1).

As shown in FIG. 13, the process 1300 starts with the patient encounter data source integration service receiving 1302 association information. This action is followed by the patient encounter data source integration service generating 1304 at least one search criterion based on the association information and searching 1306 case data stored in a case data store (e.g., the case data store 132 of FIG. 1) for a medical device case file that matches or satisfies the at least one search criterion. In some examples, the patient encounter data source integration service can receive 1302, generate 1304, and search 1306 within the process 1300 by executing actions such as those executed by the patient encounter data source integration service to receive 502, generate 504, and search 506 within the process 500 described above with reference to FIG. 5. However, within the process 1300, the patient encounter data source integration service generates 1304 at least one search criterion that specifies a list of pairs of medical device identifiers and timestamps from the association information, one of which must equate to a medical device identifier and timestamp pair associated with a case file for the case file to be a corresponding case file. The patient encounter data source integration service uses this search criterion to search 1306 for associating case files.

Next, the patient encounter data source integration service determines 1308 whether one or more corresponding case files were identified by the search 1306. Where the patient encounter data source integration service determines 1308 that no corresponding case files were found, the patient encounter data source integration service generates and returns 1310 an error message to the calling process, and the process 1300 ends. Where the patient encounter data source integration service determines 1308 that at least one corresponding case file was found, the patient encounter data source integration service generates and returns 1312 the at least one corresponding case file or at least one identifier thereof to the calling process, and the process 1300 ends.

Figure 14:
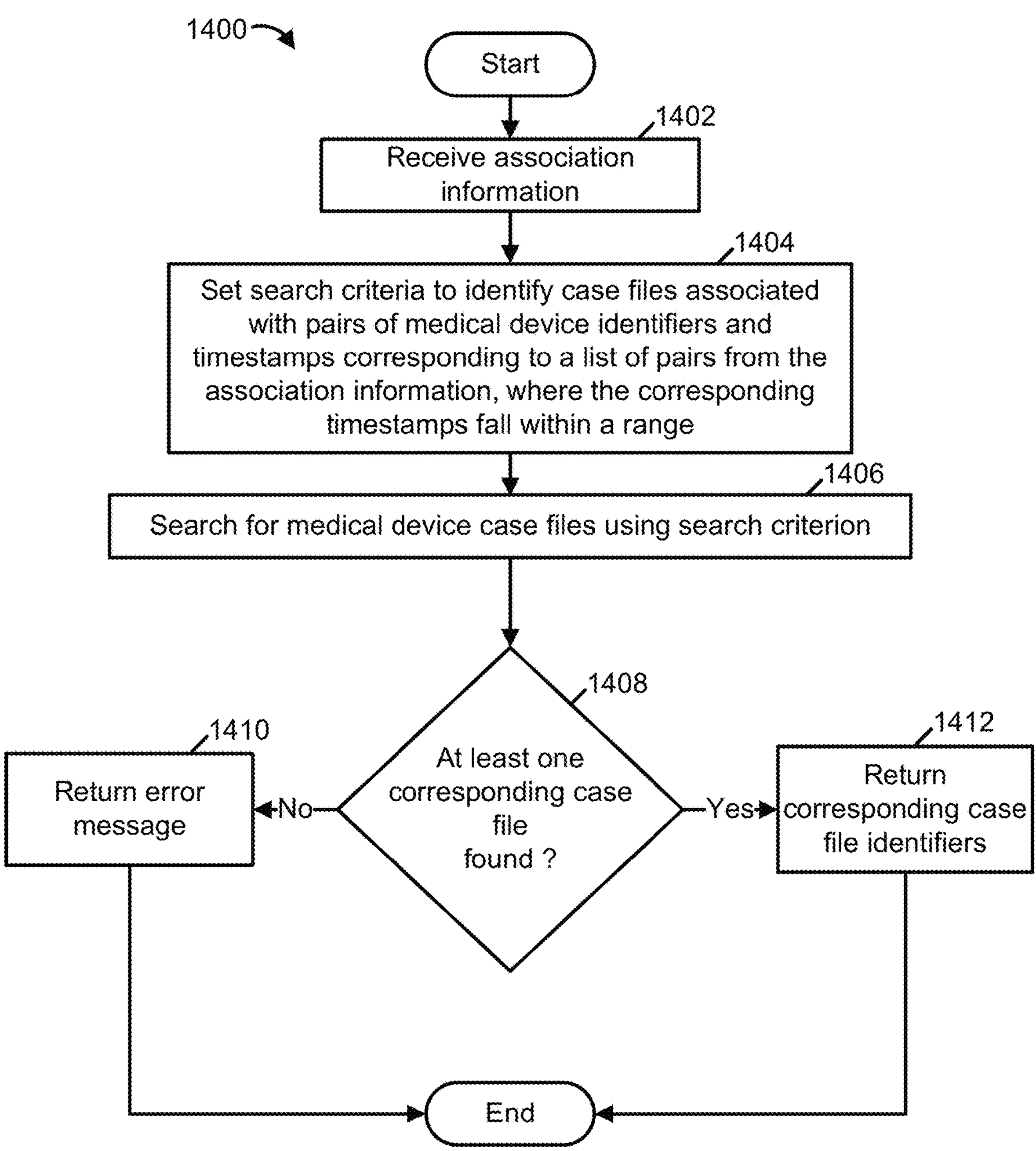
FIG. 14 is a flow diagram of a case file data source integration process executed by a patient encounter data source integration service in accordance with at least one example disclosed herein.

FIG. 14 illustrates one example of an associating process 1400 executed by a patient encounter data source integration service (e.g., the patient encounter data source integration service 130 of FIG. 1) in some implementations. The patient encounter data source integration service can be configured to execute the process 1400 in response to an event, such as expiration of a periodic timer and/or a request from a calling process (e.g., the ePCR API 128 and or the event log API 144 of FIG. 1).

As shown in FIG. 14, the process 1400 starts with the patient encounter data source integration service receiving 1402 association information. This action is followed by the patient encounter data source integration service generating 1404 at least one search criterion based on the association information and searching 1406 case data stored in a case data store (e.g., the case data store 132 of FIG. 1) for a medical device case files that matches or satisfies the at least one search criterion. In some examples, the patient encounter data source integration service can receive 1402, generate 1404, and search 1406 within the process 1400 by executing actions such as those executed by the patient encounter data source integration service to receive 502, generate 504, and search 506 within the process 500 described above with reference to FIG. 5. However, within the process 1400, the patient encounter data source integration service generates 1404 at least one search criterion that specifies a list of pairs of medical device identifiers and timestamps from the association information. In the at least one search criterion, the predetermined relationship requires that a corresponding case file be associated with a medical device identifier equal to a medical device identifier from the list and that the corresponding case file have a timestamp within a predetermined range of a timestamp paired with the medical device identifier from the list. The patient encounter data source integration service uses this search criterion to search 1406 for associating case files.

Next, the patient encounter data source integration service determines 1408 whether one or more corresponding case files were identified by the search 1406. Where the patient encounter data source integration service determines 1408 that no corresponding case files were found, the patient encounter data source integration service generates and returns 1410 an error message to the calling process, and the process 1400 ends. Where the patient encounter data source integration service determines 1408 that at least one corresponding case file was found, the patient encounter data source integration service generates and returns 1412 the at least one corresponding case file or at least one identifier thereof to the calling process, and the process 1400 ends.

Figure 15:
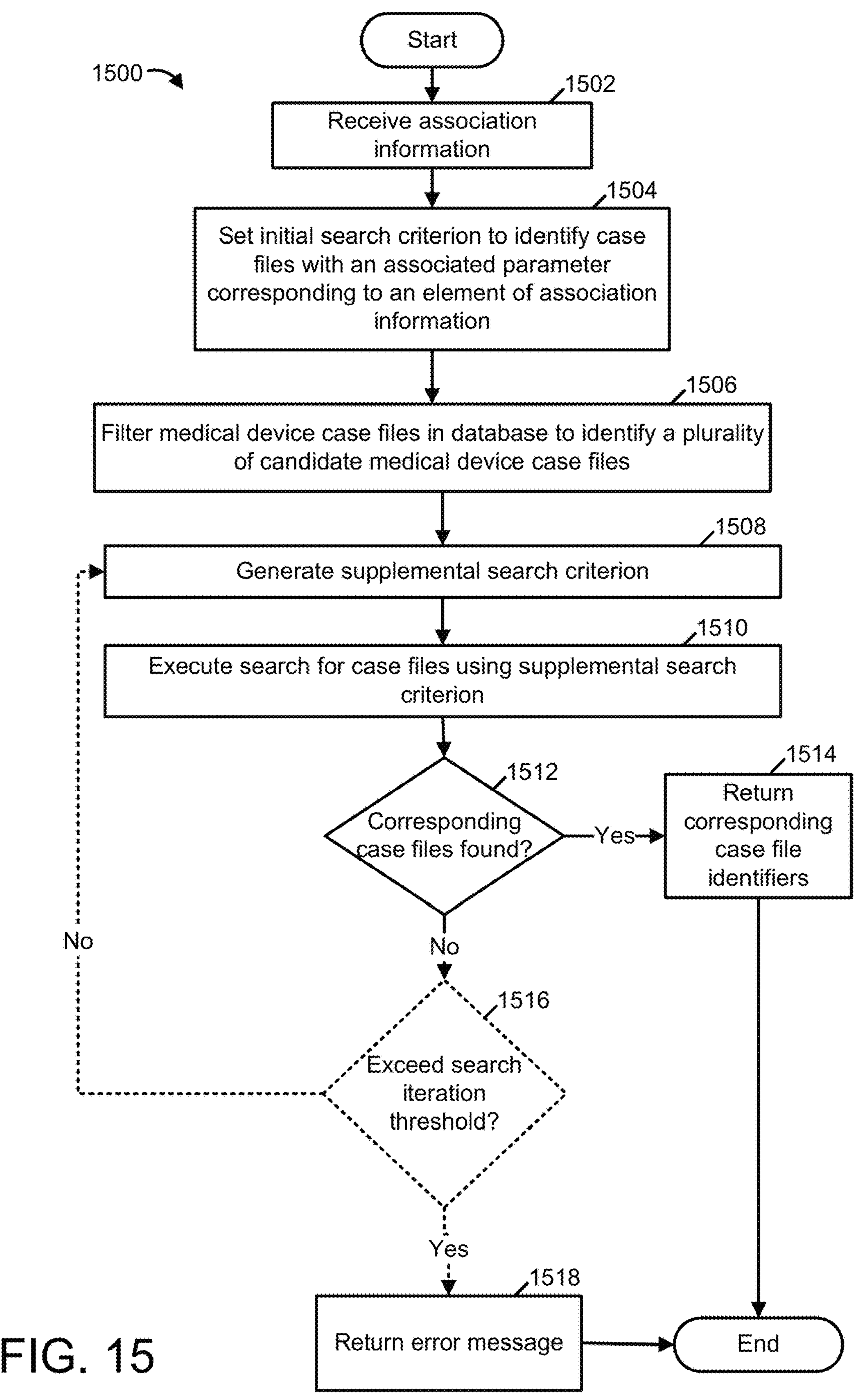
FIG. 15 is a flow diagram of a case file associating process executed by a patient encounter data source integration service in accordance with at least one example disclosed herein.

FIG. 15 illustrates one example of an associating process 1500 executed by a patient encounter data source integration service (e.g., the patient encounter data source integration service 130 of FIG. 1) in some implementations. The patient encounter data source integration service can be configured to execute the process 1500 in response to an event, such as expiration of a periodic timer and/or a request from a calling process (e.g., the ePCR API 128 and or the event log API 144 of FIG. 1). As shown in FIG. 15, operations rendered with dashed line boarders may not present in some examples.

As shown in FIG. 15, the process 1500 starts with the patient encounter data source integration service receiving 1502 association information. This action is followed by the patient encounter data source integration service generating 1504 at least one search criterion based on the association information and filtering 1506 case data stored in a case data store (e.g., the case data store 132 of FIG. 1) for medical device case files that match or satisfy the at least one search criterion. In some examples, the patient encounter data source integration service can receive 1502, generate 1504, and filter 1506 within the process 1500 by executing actions such as those executed by the patient encounter data source integration service to receive 502, generate 504, and search 506 within the process 500 described above with reference to FIG. 5. However, within the process 1500, the patient encounter data source integration service searches 1506 the case data for the case file by filtering (e.g., via a query) the case data store using an initial search criterion and, in so doing, identifies a plurality of candidate case files. In some examples, the initial search criterion employed by the filter specifies that an element of association information (e.g., a timestamp) must fall within a range of a parameter associated with a case file.

Next, the patient encounter data source integration service generates 1508 at least one supplemental search criterion. In some examples, the at least one supplemental search criterion specifies at least one supplemental predetermined relationship between at least one supplemental element of association information and at least one supplemental parameter associated with candidate case files. For example, where the at least one supplemental relationship is hard-coded, the patient encounter data source integration service generates 1508 the at least one supplemental search criterion by identifying at least one supplemental element from the association information and associating the at least one supplemental element with the at least one supplemental relationship. Alternatively or additionally, where the at least one supplemental relationship is softcoded, the patient encounter data source integration service generates 1508 the at least one supplemental search criterion by first identifying the next preferred predetermined relationship by rank within a criteria data store (e.g., the criteria data store 136 of FIG. 1) and next identifying the at least one supplemental element of association information as specified in the next preferred predetermined relationship and associating the at least one supplemental element with the at least one supplemental relationship. In at least one example, the at least one supplemental element includes a geotag and the predetermined relationship specifies that corresponding case files be associated with a geotag within a predetermined range of the geotag from the association information.

Continuing the process 1500, the patient encounter data source integration service searches 1510 the candidate case data for a medical device case files that match or satisfy the at least one supplemental search criterion. In some examples, the patient encounter data source integration service can search 1510 within the process 1500 by executing actions such as those executed by the patient encounter data source integration service to search 506 within the process 500 described above with reference to FIG. 5. However, within the process 1500, the patient encounter data source integration service can restrict its search 1510 to case data from the candidate case files. For instance, the patient encounter data source integration service can identify a candidate case file as a corresponding case file where a supplemental parameter associated with the candidate case file, stored in the case data, satisfies the supplemental relationship with the supplemental element of the association information stored in the at least one supplemental search criterion.

Next, the patient encounter data source integration service determines 1512 whether at least one corresponding case file was found. Where the patient encounter data source integration service determines 1512 that at least one corresponding case file was found, the patient encounter data source integration service generates and returns 1514 the corresponding case files or identifiers thereof to the calling process, and the process 1500 ends. Where the patient encounter data source integration service determines 1512 that no corresponding case files were found, the patient encounter data source integration service iterates a counter and determines 1516 whether the counter has transgressed a configurable constraint to the number of search iterations acceptable in a single instance of the process 1500. Where the patient encounter data source integration service determines 1516 that the counter has not transgressed the constraint, the patient encounter data source integration service generates 1508 another supplemental search criterion and the process 1500 continues. Where the patient encounter data source integration service determines 1516 that the counter has transgressed the constraint, the patient encounter data source integration service returns 1518 an error message to the calling process, and the process 1500 ends.

Figure 16:
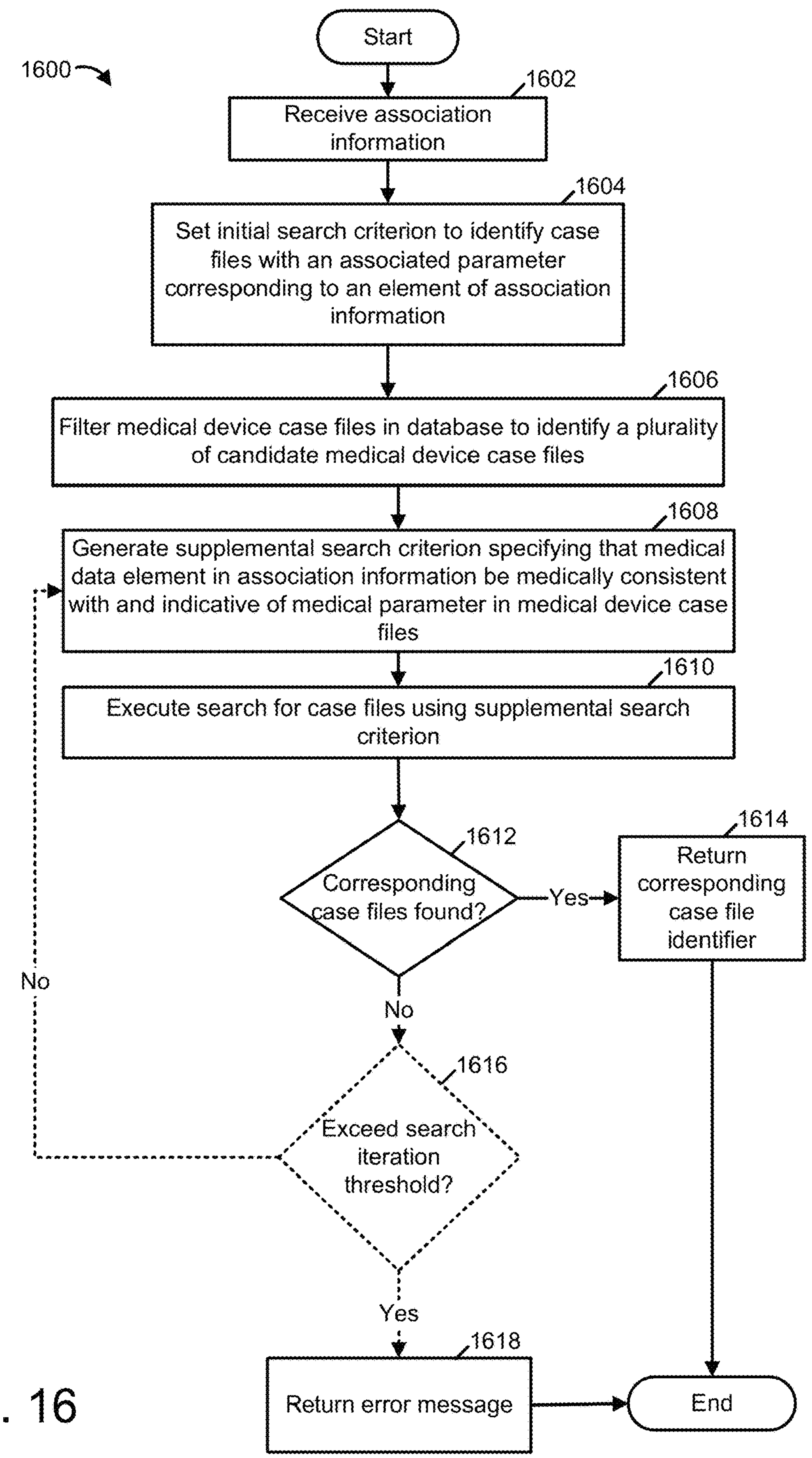
FIG. 16 is a flow diagram of a case file data source integration process executed by a patient encounter data source integration service in accordance with at least one example disclosed herein.

FIG. 16 illustrates one example of an associating process 1600 executed by a patient encounter data source integration service (e.g., the patient encounter data source integration service 130 of FIG. 1) in some implementations. The patient encounter data source integration service can be configured to execute the process 1600 in response to an event, such as expiration of a periodic timer and/or a request from a calling process (e.g., the ePCR interface 168 and or the event log API 144 of FIG. 1). As shown in FIG. 16, operations rendered with dashed line boarders may not present in some examples.

As shown in FIG. 16, the process 1600 starts with the patient encounter data source integration service receiving 1602 association information. This action is followed by the patient encounter data source integration service generating 1604 at least one search criterion based on the association information and filtering 1606 (e.g., via a query) case data stored in a case data store (e.g., the case data store 132 of FIG. 1) using the at least one search criterion to identify a plurality of candidate case files. In some examples, the patient encounter data source integration service can receive 1602, generate 1604, and filter 1606 within the process 1600 by executing actions such as those executed by the patient encounter data source integration service to receive 1502, generate 1504, and filter 1506 within the process 1500 described above with reference to FIG. 15. However, within the process 1600, the initial search criterion employed by the filter includes an initial predetermined relationship that specifies an equality between an element of association information and a parameter associated with medical device case files that is non-medical. These non-medical elements and parameters can include case start time, medical device identifier, and/or patient identifiers.

Next, the patient encounter data source integration service generates 1608 at least one supplemental search criterion. In this example, the at least one supplemental search criterion specifies that at least one medical element in the association information be medically consistent with and indicative of at least one medical parameter in a case file. In these examples, the at least one medical element can include a patient complaint, a medic impression, a drug administration, a vital sign, a physiological measurement, a treatment provided to the patient, a symptom of chest pain, an ECG with ST elevation, and/or a STEMI diagnosis. Further, in these examples, the at least one medical parameter can include a type of physiological measurement, a value of a physiological measurement, a medical treatment (e.g., a defibrillation shock), and an alarm.

Continuing the process 1600, the patient encounter data source integration service searches 1610 the candidate case data, determines 1612 whether at least one corresponding case file was found, and returns 1614 the corresponding case files or identifiers thereof to the calling process where a corresponding case file was found. Where a corresponding case file was not found, the patient encounter data source integration service determines 1616 whether a search limit has been exceeded, returns 1618 an error message indicating no corresponding case file to the calling process where the search limit has been exceeded, and returns to generate 1608 at least one supplemental search criterion where the search limit has not been exceeded. In some examples, the patient encounter data source integration service can search 1610, determine 1612, return 1614, determine 1616, and return 1618 within the process 1600 by executing actions such as those executed by the patient encounter data source integration service to search 1510, determine 1512, return 1514, determine 1516, and return 1518 within the process 1500 described above with reference to FIG. 15.

As explained above, in the process 1600 generates 1608 at least one supplemental search criterion that specifies at least one medical element in association information be medically consistent with and indicative of at least one medical parameter in a case file. In this example, the at least one predetermined relationship specifies that the association information be "medically consistent with an indicative of" case data. This predetermined relationship is complex and difficult to evaluate using commonly available comparison operations. As such, in this example, the patient encounter data source integration service evaluates the predetermined relationship while searching 1610 by executing one or more specialized heuristic, statistical, and/or machine learning processes that compare association information and case data. Table 1 provides association information and case data that satisfy the "medically consistent with and indicative of" predetermined relationship according to some examples.

TABLE 1

| MEDICAL DATA | | | |
|---|---|---|---|
| A | B | C | D |
| Primary Element of Association Information | Secondary Element of Association Information | Primary Case Data | Secondary Case Data |
| Patient complaint of Chest Pain | Drug Administration (aspirin and/or nitroglycerin) | 12 Lead ECG | Shock administration |
| Patient complaint of difficulty breathing and/or Medic Impression of Respiratory Distress | Drug Administration (albuterol, steroids, epinephrine) Airway Placement | Pulse Oximetry Capnography | 12 Lead ECG Alarms (heart rate, respiratory rate, pulse oximetry, blood pressure) |

More specifically, as shown in Table 1 columns A and B list primary and secondary elements of association information that are medically consistent with and indicative of the primary and secondary medical device case data listed on columns C and D. In some examples, the patient encounter data source integration service can generate 1608 supplemental search criteria specifying that any corresponding case data found while searching 1610 must be medically consistent with and indicative of the primary and secondary elements of association information. Alternatively, in some examples, the patient encounter data source integration service can generate 1608 a first supplemental search criterion specifying that any corresponding case data found while searching 1610 must be medically consistent with and indicative of the primary element of association information. Where no corresponding case data is found to the first supplemental search criterion during searching 1610, the patient encounter data source integration service can generate 1608 a second supplemental search criterion specifying that any corresponding case data found while searching must be medically consistent with and indicative of the secondary element of association information.

Figure 17:
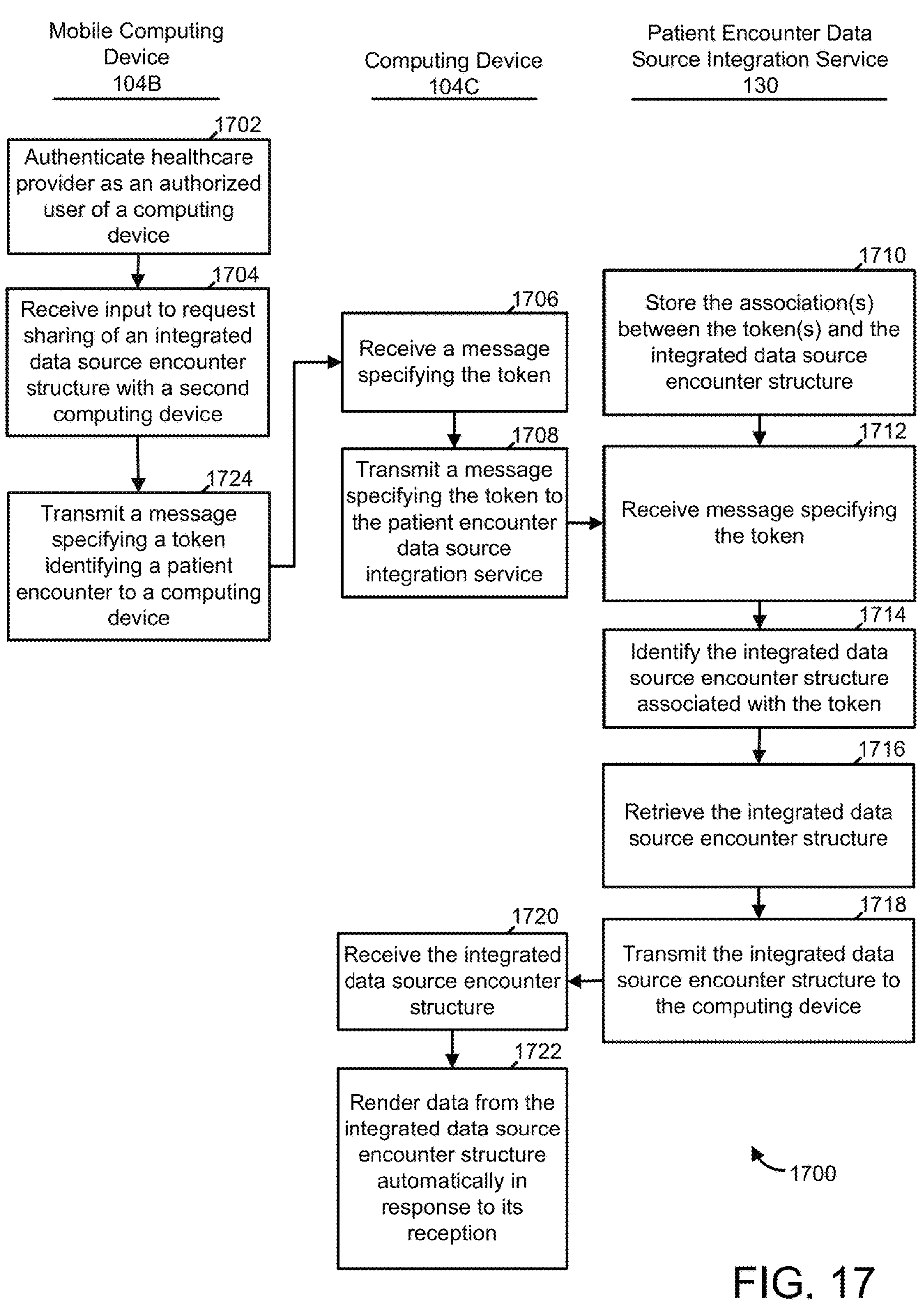
FIG. 17 is a flow diagram of a consolidated data sharing process executed by a patient encounter data source integration service in accordance with at least one example disclosed herein.

In some examples, the system 100 is configured to execute a variety of medical device case file sharing processes. FIG. 17, for instance, illustrates a sharing process 1700 that involves a mobile computing device (e.g., the mobile computing device 104A of FIG. 1), a computing device (e.g., the mobile computing device 104B of FIG. 1), and a patient encounter data source integration service.

The sharing process 1700 starts with the mobile computing device authenticating 1702 a healthcare provider (e.g., the healthcare provider 118A of FIG. 1) as an authorized user. The mobile computing device receives 1704 input from the user requesting that the mobile computing device share consolidated case data from a patient encounter with the computing device. For instance, an event log application and/or an ePCR application (e.g., the event log application 140 and/or the ePCR application 122 of FIG. 1) can receive the input. In response to reception of the input, the mobile computing device transmits 1724 a token identifying the patient encounter to the computing device. For instance, the mobile computing device may display a visual representation of the token via a user interface and/or may transmit data representing the token via NFC.

Continuing the sharing process 1700, the computing device receives 1706 the token (e.g., by scanning the visual image with a camera) and transmits 1708 a request for consolidated case data for the patient encounter identified by the token to the patient encounter data source integration service. For instance, an encounter review application (e.g., the encounter review application 148 of FIG. 1) can transmit the request.

As another part of the sharing process 1700, the patient encounter data source integration service, as part of a previously executed consolidation process (e.g., the consolidation process 400 of FIG. 4), stores 1710 the consolidated case data for the patient encounter identified by the token, in association with the token. The patient encounter data source integration service receives 1712 the request for the consolidated case data from the computing device. The patient encounter data source integration service identifies 1714 the consolidated case data using the token, retrieves 1716 the consolidated case data, and transmits 1718 the consolidated case data to the computing device.

Continuing the sharing process 1700, the computing device receives 1720 the consolidated case data and renders the consolidated case data automatically in response to receipt of the consolidated case data. For instance, the encounter review application can render an event log including the consolidated data.

Figure 18:
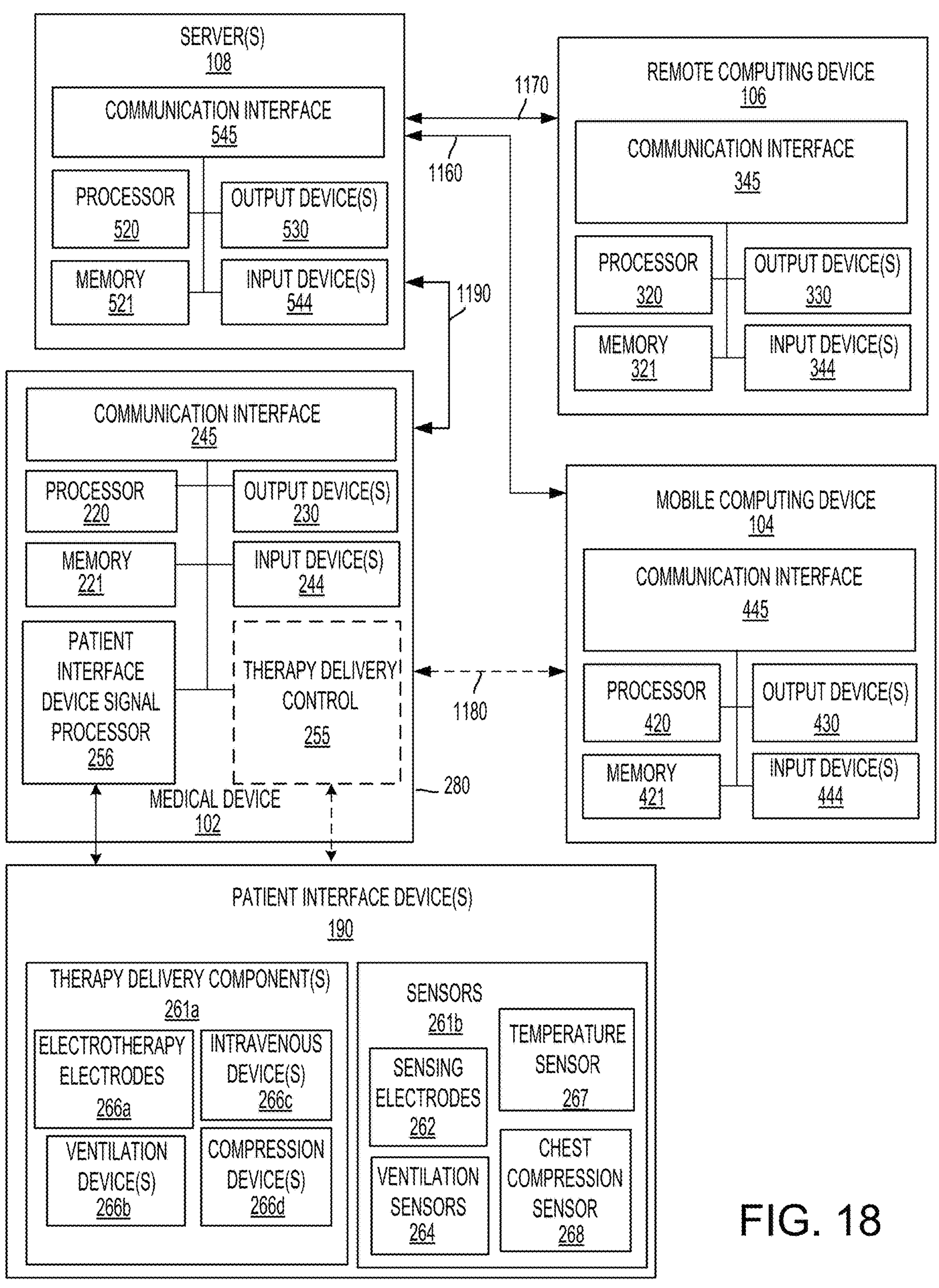
FIG. 18 is a schematic block diagram of examples of computing and medical device components with which at least one example disclosed herein may be implemented.

Referring to FIG. 18, a block diagram of examples of computing and medical device components are shown schematically.

The medical device 102 can include a processor 220, a memory 221, one or more output devices 230, one or more user input devices 244, and a communications interface 245. The communications interface 245 can include any of a variety of transmitters and/or receivers. For instance, in some examples, the communications interface 245 includes one or more of an NFC tag, an RFID tag, a barcode, and a QR code.

In various implementations, the medical device 102 can be a defibrillator, patient monitor, defibrillator/monitor, an automated compression device, a therapeutic cooling device, an extracorporeal membrane oxygenation (ECMO) device, a ventilation device, combinations thereof, or another type of medical device configured to couple to one or more therapy delivery components to provide therapy to the patient. In an implementation, the medical device 102 can be an integrated therapy delivery/monitoring device within a single housing 280. The single housing 280 can surround, at least in part, a patient interface device signal processor 256 and/or a therapy delivery control module 255.

The patient interface device(s) 190 can include one or more therapy delivery component(s) 261*a* and/or one or more sensor device(s) 261*b*. The medical device 102 can be configured to couple to the one or more therapy delivery component(s) 261*a*. In combination, the medical device 102 and the one or more therapy delivery components can provide therapeutic treatment to a patient (e.g., the patient 116 of FIG. 1). In an implementation, the medical device 102 can include or incorporate the therapy delivery component(s) 261*a*. The therapy delivery component(s) 261*a* are configured to deliver therapy to the patient and can be configured to couple to the patient. For example, the therapy delivery component(s) 261*a* can include one or more of electrotherapy electrodes including defibrillation electrodes and/or pacing electrodes, chest compression devices (e.g., one or more belts or a piston), ventilation devices (e.g., a mask and/or tubes), drug delivery devices, etc. The medical device 102 can include the one or more therapy delivery component(s) 261*a* and/or can be configured to couple to the one or more therapy delivery component(s) 261*a* in order to provide medical therapy to the patient. The therapy delivery component(s) 261*a* can be configured to couple to the patient. For example, a healthcare provider (e.g., the healthcare provider 118) may attach the electrodes to the patient, and the medical device 102 (e.g., a defibrillator or defibrillator/patient monitor) may provide electrotherapy to the patient via the defibrillation electrodes. These examples are not limiting of the disclosure as other types of medical devices, therapy delivery components, sensors, and therapy are within the scope of the disclosure.

The medical device 102 can be, for example, a therapeutic medical device capable of delivering a medical therapy. For example, the medical therapy can be electrical therapy (e.g. defibrillation, cardiac pacing, synchronized cardioversion, diaphragmatic or phrenic nerve stimulation) and the medical device 102 can be a defibrillator, a defibrillator/monitor and/or another medical device configured to provide electrotherapy. As another example, the medical therapy can be chest compression therapy for treatment of cardiac arrest and the first medical device 102 can be a mechanical chest compression device such as a belt-based chest compression device or a piston-based chest compression device. As other examples, the medical therapy can be ventilation therapy, therapeutic cooling or other temperature management, invasive hemodynamic support therapy (e.g. Extracorporeal Membrane Oxygenation (ECMO)), etc. and the medical device 102 can be a device configured to provide a respective therapy. In an implementation, the medical device 102 can be a combination of one or more of these examples. The therapeutic medical device can include patient monitoring capabilities via one or more sensors. These types of medical therapy and devices are examples only and not limiting of the disclosure.

The medical device 102 can include, incorporate, and/or be configured to couple to the one or more sensor(s) 261*b* which can be configured to couple to the patient. The sensor(s) 261*b* are configured to provide signals indicative of sensor data to the medical device 102. The sensor(s) 261*b* can be configured to couple to the patient. For example, the sensor(s) 261*b* can include cardiac sensing electrodes, a chest compression sensor, and/or ventilation sensors. The one or more sensors 261*b* can generate signals indicative of physiological parameters of the patient. For example, the physiological parameters can include one or more of at least one vital sign, an ECG, blood pressure, heart rate, pulse oxygen level, respiration rate, heart sounds, lung sounds, respiration sounds, tidal CO2, saturation of muscle oxygen (SMO2), arterial oxygen saturation (SpO2), cerebral blood flow, electroencephalogram (EEG) signals, brain oxygen level, tissue pH, tissue fluid levels, physical parameters as determined via ultrasound images, parameters determined via near-infrared reflectance spectroscopy, pneumography, and/or cardiography, etc. Additionally or alternatively, the one or more sensors 261*b* can generate signals indicative of chest compression parameters, ventilation parameters, drug delivery parameters, fluid delivery parameters, etc.

In addition to delivering therapy to the patient, the therapy delivery component(s) 261*a* can include, be coupled to, and/or function as sensors and provide signals indicative of sensor data (e.g., second sensor data) to the medical device 102. For example, the defibrillation electrodes can be configured as cardiac sensing electrodes as well as electrotherapy delivery devices and can provide signals indicative of transthoracic impedance, electrocardiogram (ECG), heart rate and/or other physiological parameters. As another example, a therapeutic cooling device can be an intravenous cooling device. Such a cooling device can include an intravenous (IV) device as a therapy delivery component configured to deliver cooling therapy and sense the patient's temperature. For example, the IV device can be a catheter that includes saline balloons configured to adjust the patient's temperature via circulation of temperature controlled saline solution. In addition, the catheter can include a temperature probe configured to sense the patient's temperature. As a further example, an IV device can provide therapy via drug delivery and/or fluid management. The IV device can also monitor and/or enabling monitoring of a patient via blood sampling and/or venous pressure monitoring (e.g., central venous pressure (CVP) monitoring).

The medical device 102 can be configured to receive the sensor signals (e.g., from the therapy delivery component(s) 261*a* and/or the sensor(s) 261*b*) and to process the sensor signals to determine and collect the patient data. The patient data can include patient data which can characterize a status and/or condition of the patient (e.g., physiological data such as ECG, heart rate, respiration rate, temperature, pulse oximetry, non-invasive hemoglobin parameters, capnography, oxygen saturation (SpO2), end tidal carbon dioxide (EtCO2), invasive blood pressure (IBP), non-invasive blood pressures (NIBP), tissue pH, tissue oxygenation, Near Infrared Spectroscopy (NIRS) measurements, etc.). Additionally or alternatively, the patient data can characterize the delivery of therapy (e.g., chest compression data such as compression depth, compression rate, etc.) and/or the patient data can characterize a status and/or condition of the medical equipment used to treat the patient (e.g., device data such as shock time, shock duration, attachment of electrodes, power-on, etc.).

The components of 220, 221, 230, 244, 245, and 255 of the medical device 102 are communicatively coupled (directly and/or indirectly) to each other for bi-directional communication.

Although shown as separate entities in FIG. 18, the one or more of the components of the medical device 102 can be combined into one or more discrete components and/or can be part of the processor 220. The processor 220 and the memory 221 can include and/or be coupled to associated circuitry to perform the functions described herein.

In an implementation, the medical device 102 can be a therapeutic medical device configured to deliver medical therapy to the patient. Thus, the medical device 102 can optionally include the therapy delivery control module 255. For example, the therapy delivery control module 255 can be an electrotherapy delivery circuit that includes one or more capacitors configured to store electrical energy for a pacing pulse or a defibrillating pulse. The electrotherapy delivery circuit can further include resistors, additional capacitors, relays and/or switches, electrical bridges such as an H-bridge (e.g., including a plurality of insulated gate bipolar transistors or IGBTs), voltage measuring components, and/or current measuring components. As another example, the therapy delivery control module 255 can be a compression device electro-mechanical controller configured to control a mechanical compression device. As a further example, the therapy delivery control module 255 can be an electro-mechanical controller configured to control drug delivery, temperature management, ventilation, and/or other type of therapy delivery. Alternatively, some examples of the medical device 102 may not be configured to deliver medical therapy to the patient 116 but can be configured to provide patient monitoring and/or diagnostic care. As shown in FIG. 18, in some examples, the therapy delivery control module 255 exchanges messages with the mobile computing device 104 (e.g., the patient mobile computing device) via a communication link 1180. These messages can include patient data descriptive of therapy provided to the patient or other patient data stored on the medical device 102. This patient data can be used by an ePCR application in generating an ePCR documenting a dispatched EMS event. In one embodiment communication link 1180 is implemented using BLUETOOTH and/or near-field communications technology.

In certain implementations the file matching and merging functionalities described herein as being associated with the patient encounter data source integration service 130 are alternatively invoked at the medical device 102 and/or the mobile computing device 104. In such implementations the communication link 1180 between the medical device 102 and the mobile computing device 104 can be used to support this functionality, thus allowing a medical device case file to be integrated with related charting data even when a connection to the server 108 is unavailable. In applications where the communication link 1180 is limited, for example due to limited bandwidth or limited duration, file matching and merging functionality is optionally limited to one or more specified search criteria, such as a search criterion that compares device identifiers. This may be particularly useful in applications where it is desired to throttle bandwidth provided by the communication link 1180 to reserve limited resources for patient treatment and EMS interactions.

The information shared via the communication link 1180 is optionally limited to increase security and/or to protect PHI. This can be accomplished by, for example, configuring the medical device 102 and the mobile computing device 104 to only communicate public information (for example, a device identifier) using the communication link 1180. In implementations where PHI is to be shared between the medical device 102 and the mobile computing device 104, the communications can be routed via a trusted cloud service where stronger authentication can be implemented. In certain embodiments the server(s) 108 provides such a trusted cloud service. Routing communications via the server(s) 108 may be preferred for other reasons as well, such as where the medical device 102 and the mobile computing device 104 produce data in different formats, and/or where one or more of the communicating devices are not configured to communicate in a local network.

The medical device 102 can incorporate and/or be configured to couple to one or more patient interface device(s) 190. The patient interface device(s) 190 can include one or more therapy delivery component(s) 261*a* and one or more sensor(s) 261*b*. The one or more therapy delivery component(s) 261*a* and the one or more sensor(s) 261*b* sensor can provide one or more signals to the medical device 102 via wired and/or wireless connection(s).

The one or more therapy delivery component(s) 261*a* can include electrotherapy electrodes (e.g., the electrotherapy electrodes 266*a*), ventilation device(s) (e.g., the ventilation devices 266*b*), intravenous device(s) (e.g., the intravenous devices 266*c*), compression device(s) (e.g., the compression devices 266*d*), etc. For example, the electrotherapy electrodes can include defibrillation electrodes, pacing electrodes, and/or combinations thereof. The ventilation devices can include a tube, a mask, an abdominal and/or chest compressor (e.g., a belt, a cuirass, etc.), etc. and combinations thereof. The intravenous devices can include drug delivery devices, fluid delivery devices, and combinations thereof. The compression devices can include mechanical compression devices such as abdominal compressors, chest compressors, belts, pistons, and combinations thereof. In various implementation, the therapy delivery component(s) 261*a* can be configured to provide sensor data and/or be coupled to and/or incorporate sensors. For example, the electrotherapy electrodes can provide sensor data such as transthoracic impedance, ECG, heart rate, etc. Further the electrotherapy electrodes can include and or be coupled to a chest compression sensor. As another example, the ventilation devices can be coupled to and/or incorporate flow sensors, gas species sensors (e.g., oxygen sensor, carbon dioxide sensor, etc.), etc. As a further example, the intravenous devices can be coupled to and/or incorporate temperature sensors, flow sensors, blood pressure sensors, etc. As yet another example, the compression devices can be coupled to and/or incorporate chest compression sensors, patient position sensors, etc. The therapy delivery control module 255 can be configured to couple to and control the therapy delivery component(s) 261*a*.

In various implementations, the sensor(s) 261*b* can include one or more sensor devices configured to provide sensor data that includes, for example, but not limited to electrocardiogram (ECG), blood pressure, heart rate, pulse oxygen level, respiration rate, heart sounds, lung sounds, respiration sounds, tidal CO2, saturation of muscle oxygen (SMO2), arterial oxygen saturation (SpO2), cerebral blood flow, electroencephalogram (EEG) signals, brain oxygen level, tissue pH, tissue fluid levels, images and/or videos via ultrasound, laryngoscopy, and/or other medical imaging techniques, near-infrared reflectance spectroscopy, pneumography, cardiography, and/or patient movement. Images and/or videos can be two-dimensional or three-dimensional.

The sensor(s) 261*b* can include sensing electrodes (e.g., the sensing electrodes 262), ventilation sensors (e.g., the ventilation sensors 264), temperature sensors (e.g., the temperature sensor 267), chest compression sensors (e.g., the chest compression sensor 268), etc. For example, the sensing electrodes can include cardiac sensing electrodes. The cardiac sensing electrodes can be conductive and/or capacitive electrodes configured to measure changes in a patient's electrophysiology, for example to measure the patient's ECG information. In an implementation, the sensing electrodes can be configured to measure the transthoracic impedance and/or a heart rate of the patient. The ventilation sensors can include spirometry sensors, flow sensors, pressure sensors, oxygen and/or carbon dioxide sensors such as, for example, one or more of pulse oximetry sensors, oxygenation sensors (e.g., muscle oxygenation/pH), O2 gas sensors and capnography sensors, and combinations thereof. The temperature sensors can include an infrared thermometer, a contact thermometer, a remote thermometer, a liquid crystal thermometer, a thermocouple, a thermistor, etc. and can measure patient temperature internally and/or externally. The chest compression sensor can include one or more motion sensors including, for example, one or more accelerometers, one or more force sensors, one or more magnetic sensors, one or more velocity sensors, one or more displacement sensors, etc. The chest compression sensor can be, for example, but not limited to, a compression puck, a smart phone, a hand-held device, a wearable device, etc. The chest compression sensor can be configured to detect chest motion imparted by a rescuer and/or an automated chest compression device (e.g., a belt system, a piston system, etc.). The chest compression sensor can provide signals indicative of chest compression data including displacement data, velocity data, release velocity data, acceleration data, compression rate data, dwell time data, hold time data, blood flow data, blood pressure data, etc. In an implementation, the sensing electrodes and/or the electrotherapy electrodes can include or be configured to couple to the chest compression sensor.

Continuing with FIG. 18, examples of components of the mobile computing device 104 are shown schematically. In an implementation, the mobile computing device 104 can be configured as a mobile computing device. The mobile computing device 104 can include a processor 420, a memory 421, one or more output devices 430, one or more user input devices 444, and a communications interface 445. FIG. 18 also illustrates schematically examples of components of the remote computing device 106. As shown in FIG. 18, remote the computing device 106 can include a processor 320, a memory 321, one or more output devices 330, one or more user input devices 344, and a communications interface 345. FIG. 18 further illustrates schematically examples of components of the server(s) 108. As shown in FIG. 18, the server(s) 108 can include a processor 520, a memory 521, one or more output devices 530, one or more user input devices 544, and a communications interface 545.

Each of the mobile computing device 104 (e.g., the mobile computing device) and the remote computing device 106 can be a computer system, such as a desktop, notebook, mobile, portable, or other type of computing system. Each of these devices 104 and 106 can include server(s) and/or access server(s) via a monitor and/or other connected user interface device. Although described as server(s), the server(s) 108 can be another type of computing system including for example a desktop, notebook, mobile, portable, or other type of computing system.

As shown in FIG. 18, each of the devices 104 and 106, along with the server(s) 108 and the medical device 102, includes a bus or other interconnection mechanism that communicably couples the processor, memory, output devices, input devices, and communication interface included therein. The bus can include a PCI/PCI-X or SCSI based system bus depending on the storage devices used, for example.

The processors 220, 320, 420, and 520 can each include a processor, such as, but not limited to, an Intel® Itanium® or Itanium 2® processor(s), or AMD® Opteron® or Athlon MP® processor(s), or Motorola® lines of processors. The communication interfaces 245, 345, 445, and 545 can each be any of an RS-232 port for use with a modem-based dialup connection, a 10/100 Ethernet port, or a Gigabit port using copper or fiber, for example. The communication interfaces 245, 345, 445, and 545 may be chosen depending on a network(s) such a Local Area Network (LAN), Wide Area Network (WAN), or any network to which the medical device 102, the mobile computing device 104, the remote computing device 106, and/or the server(s) 108 may connect. The memories 221, 321, 421, and 521 can be Random Access Memory (RAM), Read Only Memory (ROM), Flash memory, and/or another dynamic volatile and/or non-volatile storage device(s). The memories 221, 321, 421, and 521 can be used to store information and instructions. For example, hard disks such as the Adaptec® family of SCSI drives, an optical disc, an array of disks such as RAID (e.g. the Adaptec family of RAID drives), or any other mass storage devices may be used. The components described above are meant to exemplify some types of possibilities. In no way should the aforementioned examples limit the scope of the disclosure. The memories 221, 321, 421, and 521 can further include removable storage media such as external hard-drives, floppy drives, flash drives, IOMEGA® Zip Drives, Compact Disc-Read Only Memory (CD-ROM), Compact Disc-Re-Writable (CD-RW), or Digital Video Disk-Read Only Memory (DVD-ROM), for example.

Continuing with FIG. 18, the server(s) 108 can include, for example, the one or more storage server(s) and one or more application server(s). In some examples, the server(s) 108 are configured to exchange messages 1170 with the remote computing device 106. These messages can include charting and/or case data as described above. In some examples, the server(s) 108 are configured to exchange messages 1160 with the mobile computing device 104 via the ePCR API 128. These messages can include data descriptive of ePCRs generated by the mobile computing device 104. In some examples, the server(s) 108 are configured to exchange messages 1190 with the medical device 102. These messages can include data descriptive of a patient (e.g., the patient 116 of FIG. 1) being treated via by the medical device and/or treatment being delivered by the medical device 102.

Some examples of the present disclosure include various steps, some of which can be performed by hardware components or can be embodied in machine-executable instructions. These machine-executable instructions can be stored on a non-transitory data storage medium and can be used to cause a general-purpose or a special-purpose processor programmed with the instructions to perform the steps. The non-transitory data storage medium can further to store an operating system and the machine-executable instructions can be included within one or more software applications or programs, such as the ePCR application 122. These programs can implement the features disclosed herein and the methods that they execute. Alternatively, the steps can be performed by a combination of hardware, software, and/or firmware, on one device and/or distributed across multiple devices and/or processors. In addition, some examples of the present disclosure can be performed or implemented, at least in part (e.g., one or more modules), on one or more computer systems, mainframes (e.g., IBM mainframes such as the IBM zSeries, Unisys ClearPath Mainframes, HP Integrity NonStop server(s), NEC Express series, and others), or client-server type systems. In addition, specific hardware aspects of examples of the present disclosure can incorporate one or more of these systems, or portions thereof.

Having thus described several aspects of at least one example, it is to be appreciated that various alterations, modifications, and improvements will readily occur to those skilled in the art. For instance, examples disclosed herein can also be used in other contexts. Such alterations, modifications, and improvements are intended to be part of this disclosure and are intended to be within the scope of the examples discussed herein. Accordingly, the foregoing description and drawings are by way of example only.

The invention claimed is:

1. A system for consolidating data generated by multiple medical devices used for treating a patient during a patient encounter, the system comprising:

a plurality of medical devices, each respective medical device of the plurality of medical devices comprising:

a medical device communications interface configured to transmit at least one medical device case file to a server, one or more processors coupled with the medical device communications interface and configured to:

store case data in the at least one medical device case file, wherein the case data comprises at least one of physiological data, treatment data, or performance data captured during patient treatment, and transmit, via the medical device communications interface, the at least one medical device case file to the server, and an identifier for uniquely identifying the respective medical device, wherein at least one medical device of the plurality of medical devices comprises at least one sensor configured to couple with a patient to acquire physiological signals from the patient, wherein the one or more processors of each medical device of the at least one medical device is configured to receive the physiological signals acquired by the at least one sensor, and convert the physiological signals to the physiological data of the case data;

a mobile computing device comprising:

a network interface configured to communicate with the server, a medical device interface configured to record a representation of the identifier of each medical device of the plurality of medical devices by at least one of i) scanning a visible code or identifier or ii) acquiring content of a tag via near field communications (NFC) or radio frequency identification (RFID) connection, and at least one processor coupled with the network interface and the medical device interface, the at least one processor being configured to:

responsive to user input at the mobile computing device, for each respective medical device of the plurality of medical devices, a) record, via the medical device interface while the respective medical device is in range of the medical device interface, a respective representation of the identifier of the respective medical device, and b) generate a respective timestamp indicating when the respective representation was recorded, generate a data structure comprising a plurality of fields, the plurality of fields comprising:

at least one field storing a patient encounter identifier uniquely identifying a patient encounter corresponding to the patient at an emergency medical scene and involving use of the plurality of medical devices, and a plurality of medical device identifier fields comprising, for each respective medical device of the plurality of medical devices, a respective field storing the respective representation of the identifier, and a respective timestamp field storing the respective timestamp indicating when the respective representation was recorded, and transmit, via the network interface, the data structure to the server; and the server, comprising:

a server memory, a server communications interface, and at least one server processor coupled with the server memory and the server communications interface and configured to:

receive, via the server communications interface, the data structure from the mobile computing device, receive, via the server communications interface and separately from the data structure, a plurality of medical device case files comprising the at least one medical device case file from each medical device of the plurality of medical devices, store, to at least one non-transitory computer-readable data store, the plurality of medical device case files, parse the data structure to extract the patient encounter identifier, the representations of the identifiers of the plurality of medical devices, and the respective timestamps, identify a portion of the plurality of medical device case files as being associated with the patient encounter identifier by matching the representation of the identifier of a given medical device of the plurality of medical devices and a given medical device case file, and determining that a time range associated with the given medical device case file includes the respective timestamp indicating when the representation of the identifier of the given medical device was recorded, consolidate the portion of the plurality of medical device case files into an integrated encounter structure corresponding to the patient encounter identifier, the integrated encounter structure comprising information identifying each medical device case file of the portion of the plurality of medical device case files, and as further medical device case files are received from one or more medical devices of the plurality of medical devices, transmit, in real-time, updated consolidated case data to one or more remote computing devices, each remote computing device executing a data collection app configured to issue a notification based on receipt of new data.

2. The system of claim 1, wherein the at least one server processor is further configured to transmit the integrated encounter structure to a receiving computing device.

3. The system of claim 2, wherein the receiving computing device comprises the mobile computing device.

4. The system of claim 3, wherein the at least one processor of the mobile computing device is further configured to visually render at least a portion of the integrated encounter structure via a touch screen of the mobile computing device.

5. The system of claim 2, wherein the receiving computing device comprises at least one medical device of the plurality of medical devices.

6. The system of claim 2, wherein the receiving computing device comprises a computing device within an emergency response center.

7. The system of claim 6, wherein:

the data structure comprises a token to access the integrated encounter structure;

the server is further configured to receive the token from the computing device within the emergency response center; and the at least one server processor is configured to automatically transmit the integrated encounter structure to the computing device in response to reception of the token.

8. The system of claim 7, wherein the mobile computing device is configured to transmit the token to the computing device within the emergency response center.

9. The system of claim 1, wherein to transmit the at least one medical device case file comprises to transmit one or more streams of the case data to the at least one medical device case file.

10. The system of claim 9, wherein the integrated encounter structure comprises information identifying the case data of each stream of the one or more streams of the case data from the at least one medical device case file.

11. The system of claim 1, further comprising a computing device comprising at least one user interface and configured to:

receive the integrated encounter structure; and render at least a portion of the integrated encounter structure via the at least one user interface.

12. The system of claim 1, wherein the plurality of medical devices comprises one or more of: a defibrillator, a patient monitor, an automated external defibrillator, a ventilator, an automated chest compression device, and a wearable defibrillator.

13. The system of claim 1, wherein the data structure comprises patient information.

14. The system of claim 13, wherein the patient information comprises one or more of patient name, patient identifier, age, gender, weight, height, and past medical history.

15. The system of claim 1, wherein the data structure comprises other timestamp information indicating when the at least one medical device case file was created.

16. The system of claim 1, wherein:

the at least one server processor is configured to generate at least one search criterion based at least in part on the respective timestamps; and identifying portion of the plurality of medical device case files comprises using the generated at least one search criterion to match the representation of the identifier of the given medical device of the plurality of medical devices and the given medical device case file, and to determine the time range associated with the given medical device case file includes the respective timestamp indicating when the representation of the identifier of the given medical device was recorded.

17. The system of claim 1, wherein the data structure comprises geolocation information indicating where the mobile computing device was located when each respective representation of the identifier of each medical device was recorded.

18. The system of claim 1, wherein the medical device interface comprises at least one of: a camera, a near-field communication sensor, a radio frequency identification sensor, a universal serial bus connector, an infrared sensor, a personal area network sensor, a proximity detector, a geolocation detector, and a wireless network connector.

19. The system of claim 1, wherein:

the medical device interface of the mobile computing device comprises a camera; and the identifiers of the plurality of medical devices comprise one or more of a QR bar code and a bar code.

20. The system of claim 1, wherein the mobile computing device is further configured to generate one or more log entries.

21. The system of claim 20, wherein the mobile computing device is configured to transmit the one or more log entries to the server for inclusion in the integrated encounter structure.

22. The system of claim 1, wherein the case data of at least one medical device of the plurality of medical devices comprises physiological data comprising one or more of: ECG data, oxygen saturation data, capnographic data, and blood pressure data.

23. The system of claim 1, wherein the case data of at least one medical device of the plurality of medical devices comprises treatment data comprising one or more of: defibrillation data, drug infusion data, chest compression data, and ventilation data.

24. The system of claim 1, wherein the case data of at least one medical device of the plurality of medical devices comprises performance data comprising one or more of: chest compression performance data and ventilation performance data.

25. The system of claim 1, wherein the case data of at least one medical device of the plurality of medical devices comprises protected health information.

26. The system of claim 1, wherein the identifiers of the plurality of medical devices comprise at least one of a quick reference (QR) bar code, a radio frequency identifier (RFID), a serial number, or a transmission control protocol/internet protocol (TCP/IP) address.

27. The system of claim 1, wherein the integrated encounter structure comprises the respective case data from each medical device case file of the portion of the plurality of medical device case files.

* * * * *